(12) United States Patent
Santamore et al.

(10) Patent No.: US 9,381,157 B2
(45) Date of Patent: *Jul. 5, 2016

(54) PREVENTION OF MYOCARDIAL INFARCTION INDUCED VENTRICULAR EXPANSION AND REMODELING

(71) Applicant: Cormend Technologies, LLC, Needham, MA (US)

(72) Inventors: William P. Santamore, Medford, NJ (US); Jeanne M. Lesniak, Natick, MA (US)

(73) Assignee: CORMEND TECHNOLOGIES, LLC, Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/560,588

(22) Filed: Dec. 4, 2014

(65) Prior Publication Data

US 2015/0139911 A1   May 21, 2015

Related U.S. Application Data

(63) Continuation of application No. 13/116,836, filed on May 26, 2011, now Pat. No. 8,936,027, and a continuation of application No. 10/958,063, filed on Oct. 4, 2004, now Pat. No. 7,988,727, and a continuation of application No. 10/131,090, filed on Apr. 25, 2002, now abandoned.

(60) Provisional application No. 60/286,521, filed on Apr. 27, 2001.

(51) Int. Cl.
*A61F 2/24*       (2006.01)
*A61K 9/14*       (2006.01)

(Continued)

(52) U.S. Cl.
CPC ............. *A61K 9/14* (2013.01); *A61B 17/00234* (2013.01); *A61B 17/064* (2013.01); *A61B 17/3468* (2013.01); *A61K 9/0024* (2013.01); *A61K 47/02* (2013.01); *A61K 47/42* (2013.01); *A61K 49/0013* (2013.01); *A61K 49/04* (2013.01); *A61B 17/00491* (2013.01); *A61B 17/068* (2013.01); *A61B 17/0644* (2013.01); *A61B 2017/00243* (2013.01); *A61B 2017/00247* (2013.01); *A61B 2017/00862* (2013.01); *A61B 2017/044* (2013.01); *A61B 2017/0404* (2013.01); *A61B 2017/048* (2013.01); *A61B 2017/0412* (2013.01); *A61B 2017/0422* (2013.01); *A61B 2017/0427* (2013.01);

(Continued)

(58) Field of Classification Search
CPC .................................. A61F 25/01; A61K 9/14
USPC .................................................... 623/2.1, 904
See application file for complete search history.

(56) References Cited

U.S. PATENT DOCUMENTS

| 5,116,615 A |   | 5/1992 | Gokcen et al. |
| 5,142,621 A | * | 8/1992 | Guttag ................... G06F 9/345 345/561 |

(Continued)

*Primary Examiner* — Suzette J Gherbi
(74) *Attorney, Agent, or Firm* — Mannava & Kang, P.C.; Carol L. Bunner

(57) ABSTRACT

A method for direct therapeutic treatment of myocardial tissue in a localized region of a heart having a pathological condition. The method includes identifying a target region of the myocardium and applying material directly and substantially only to at least a portion of the myocardial tissue of the target region. The material applied results in a physically modification the mechanical properties, including stiffness, of said tissue. Various devices and modes of practicing the method are disclosed for stiffening, restraining and constraining myocardial tissue for the treatment of conditions including myocardial infarction or mitral valve regurgitation.

18 Claims, 48 Drawing Sheets

(51) Int. Cl.
*A61B 17/00* (2006.01)
*A61B 17/064* (2006.01)
*A61B 17/34* (2006.01)
*A61K 9/00* (2006.01)
*A61K 47/02* (2006.01)
*A61K 47/42* (2006.01)
*A61K 49/00* (2006.01)
*A61K 49/04* (2006.01)
*A61B 17/068* (2006.01)
*A61B 17/04* (2006.01)
*A61B 18/00* (2006.01)

(52) U.S. Cl.
CPC ...... *A61B 2017/0437* (2013.01); *A61B 2017/0443* (2013.01); *A61B 2017/0464* (2013.01); *A61B 2017/0641* (2013.01); *A61B 2017/0647* (2013.01); *A61B 2017/0649* (2013.01); *A61B 2018/00392* (2013.01); *A61F 2/2451* (2013.01); *A61F 2/2493* (2013.01); *A61F 2002/249* (2013.01); *Y10S 623/904* (2013.01)

(56) References Cited

U.S. PATENT DOCUMENTS

| | | | | |
|---|---|---|---|---|
| 5,211,952 | A | 5/1993 | Spicer et al. | |
| 5,498,613 | A * | 3/1996 | Rodgers | A61K 31/519 424/450 |
| 5,665,383 | A * | 9/1997 | Grinstaff | A23L 1/296 424/450 |
| 5,722,403 | A * | 3/1998 | McGee | A61N 1/44 600/373 |
| 5,740,808 | A * | 4/1998 | Panescu | A61B 5/0066 600/424 |
| 5,993,855 | A * | 11/1999 | Yoshimoto | A61K 9/0085 424/457 |
| 6,416,510 | B1 | 7/2002 | Altman et al. | |
| 7,311,731 | B2 * | 12/2007 | Lesniak | A61B 17/00234 424/489 |
| 7,988,727 | B2 * | 8/2011 | Santamore | A61B 17/00234 606/16 |
| 8,936,027 | B2 * | 1/2015 | Santamore | A61B 17/00234 128/898 |
| 2001/0002399 | A1* | 5/2001 | MacLaughlan | A61K 31/585 514/310 |
| 2002/0049155 | A1* | 4/2002 | Hogenkamp | A61K 47/48023 424/1.69 |
| 2002/0056461 | A1* | 5/2002 | Jayaraman | A61B 17/00234 128/898 |
| 2002/0169360 | A1* | 11/2002 | Taylor | A61B 17/00234 600/37 |
| 2003/0135113 | A1* | 7/2003 | Altman | A61B 18/1492 600/431 |
| 2003/0236323 | A1* | 12/2003 | Ratner | C08F 8/14 524/27 |
| 2012/0109044 | A1* | 5/2012 | Santamore | A61B 17/00234 604/22 |

* cited by examiner

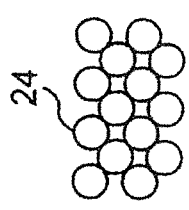
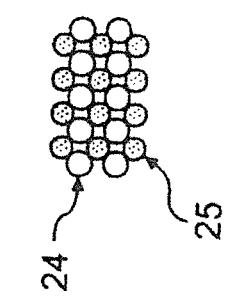
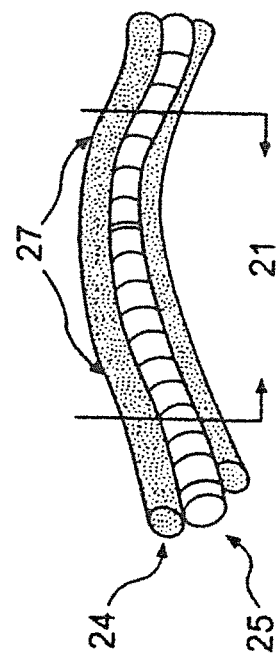
FIG. 3B
FIG. 3C
FIG. 3D
FIG. 3E

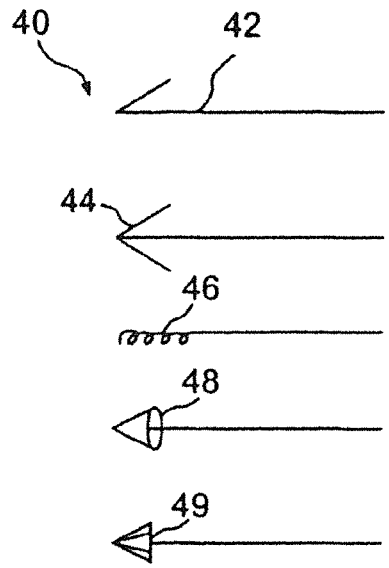
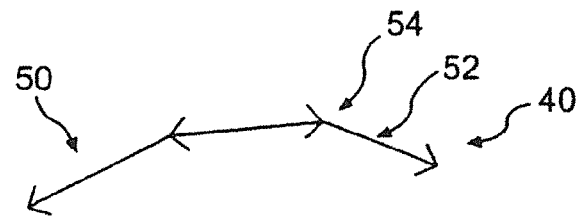
FIG. 5B
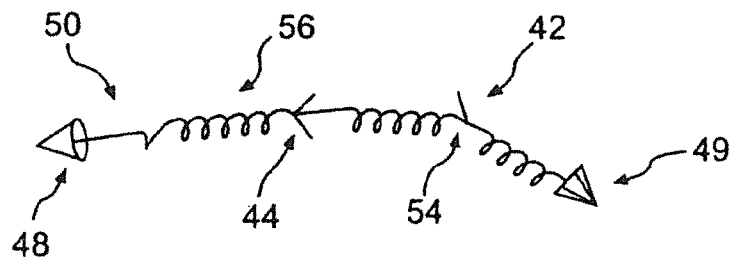
FIG. 5A
FIG. 5C
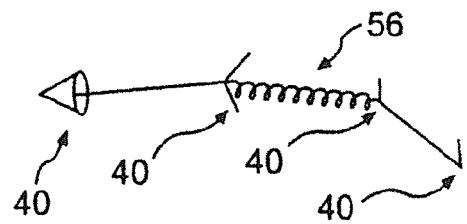
FIG. 5D

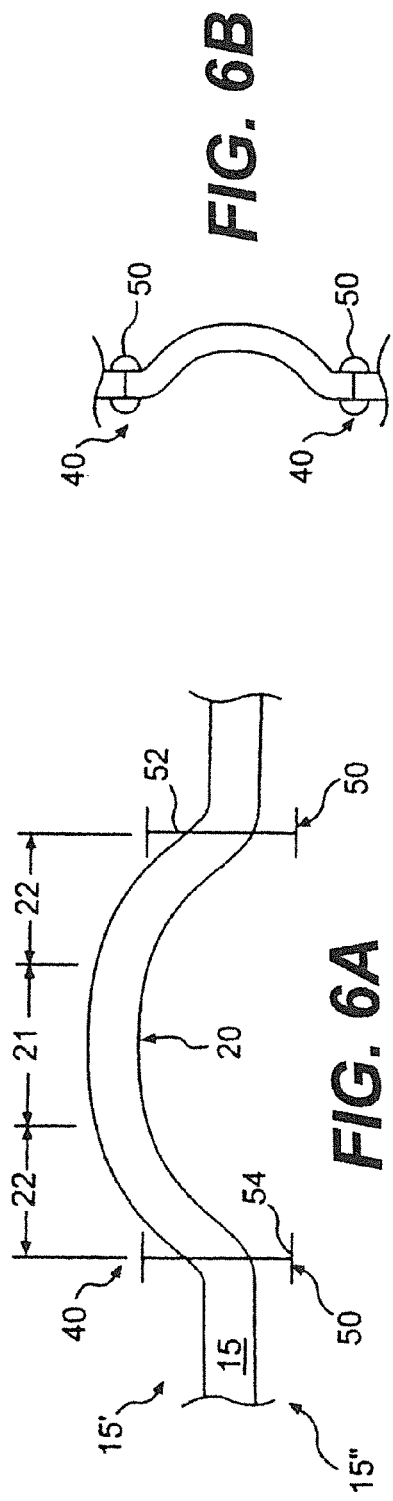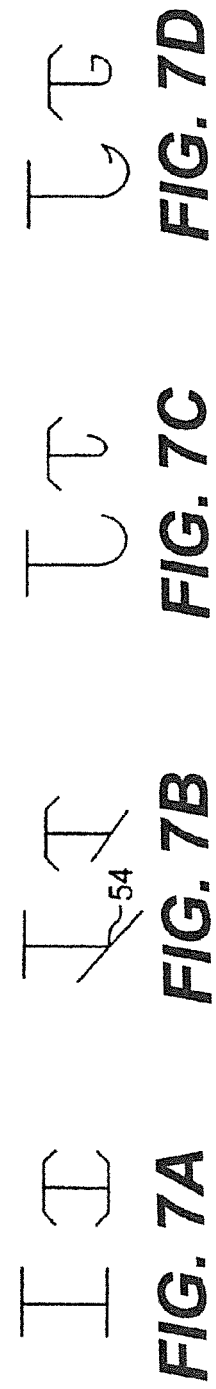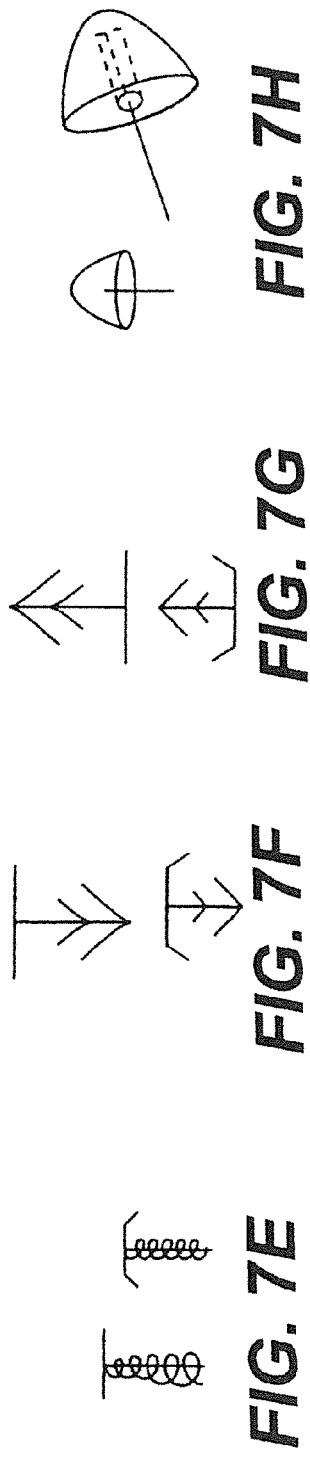

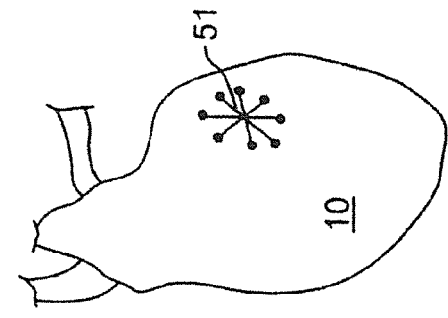
FIG. 8
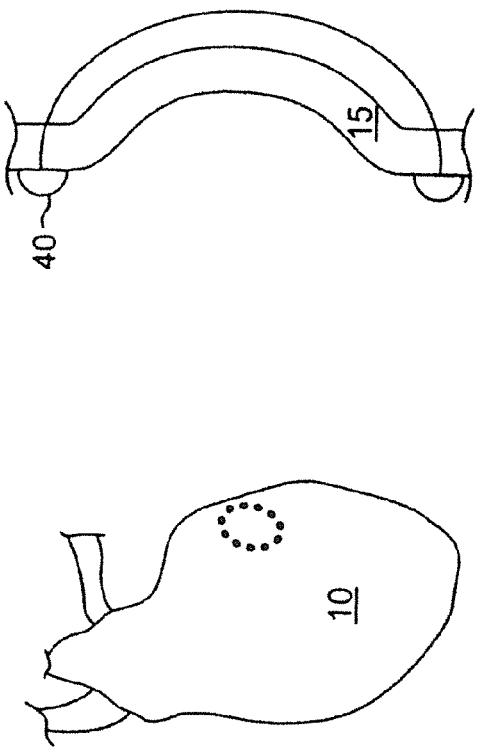
FIG. 9A
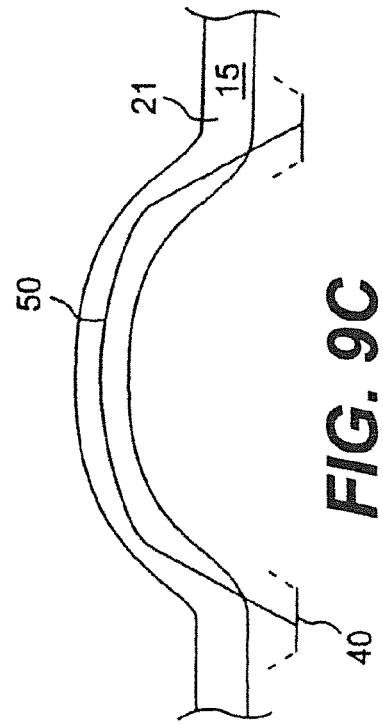
FIG. 9D
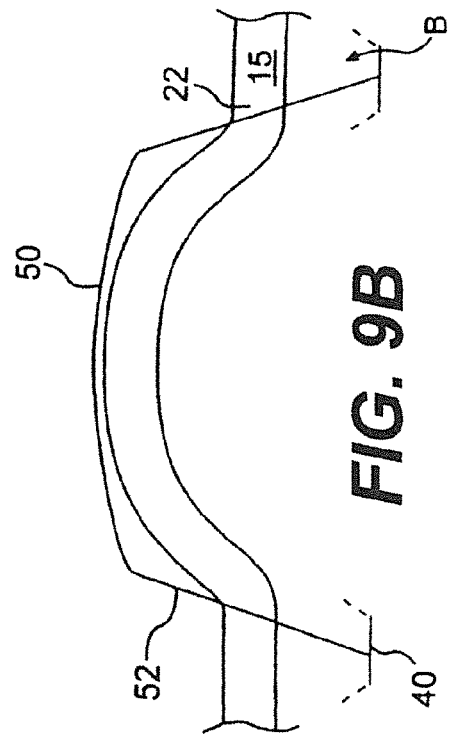
FIG. 9B
FIG. 9C

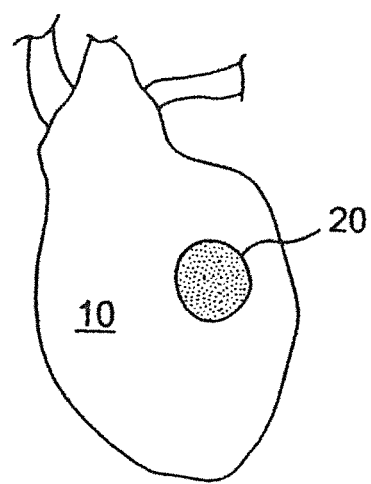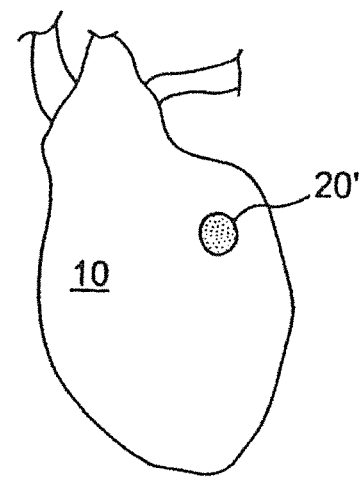
*FIG. 16E*  *FIG. 16F*
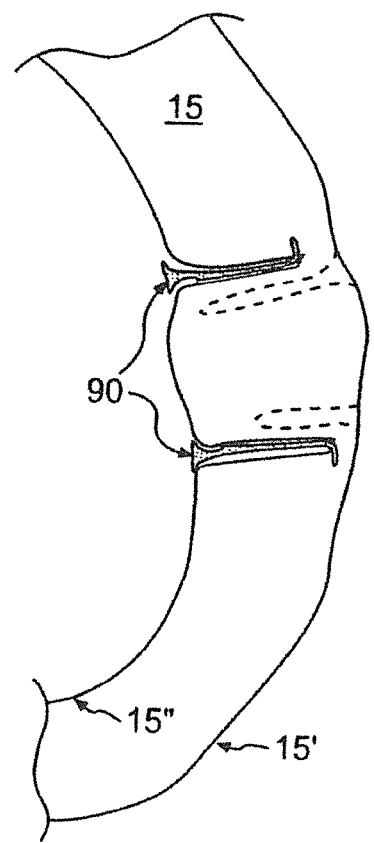
*FIG. 17*

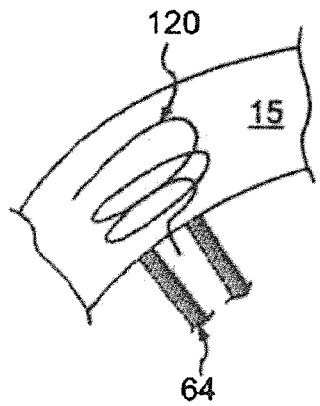
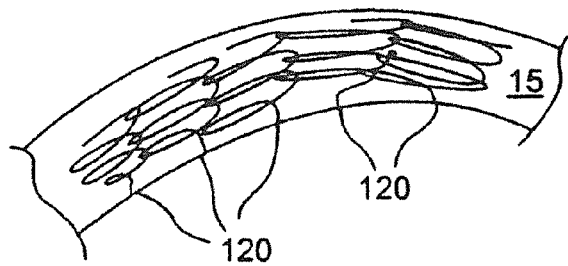
*FIG. 35A*  *FIG. 35B*
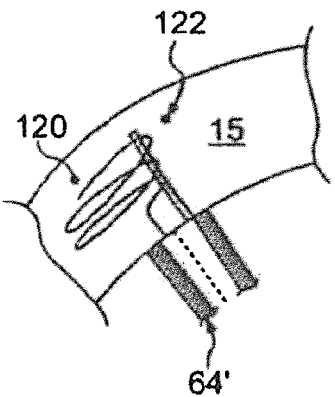
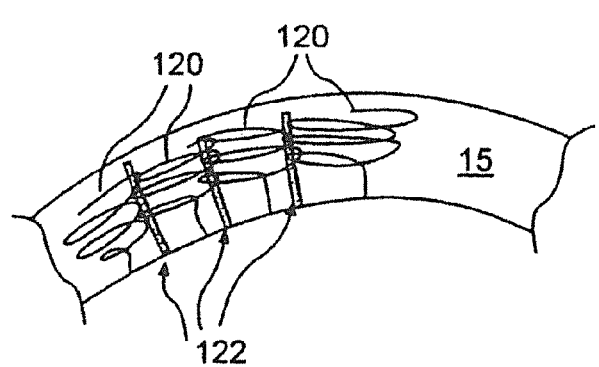
*FIG. 35C*  *FIG. 35D*
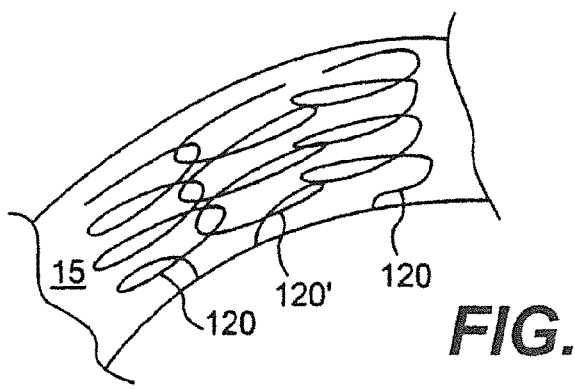
*FIG. 35E*

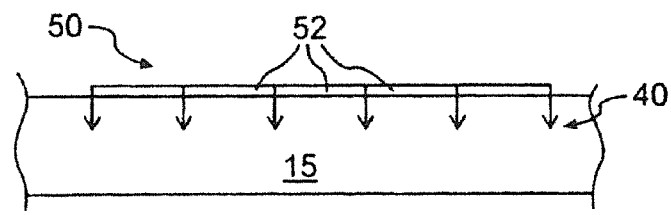
FIG. 37A
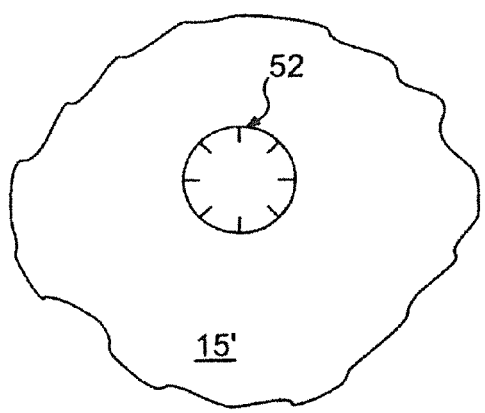 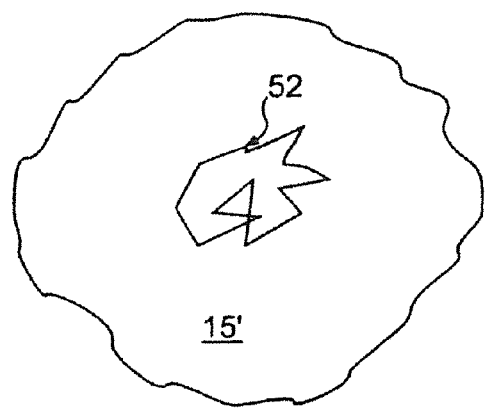
FIG. 37B         FIG. 37C
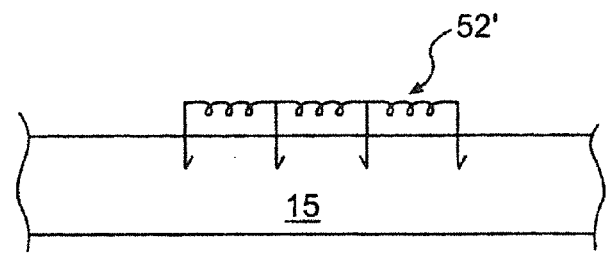
FIG. 37D

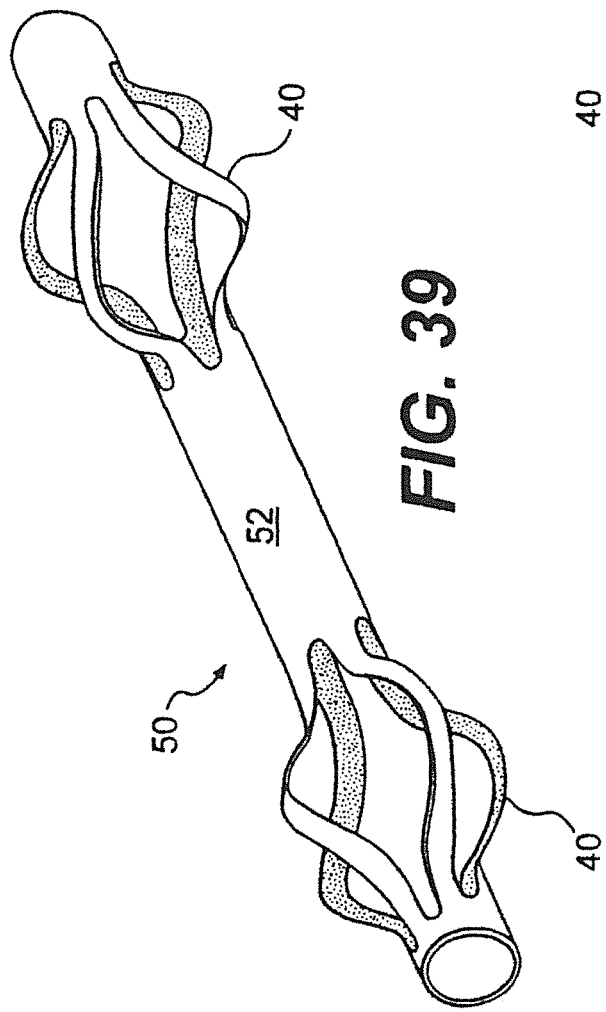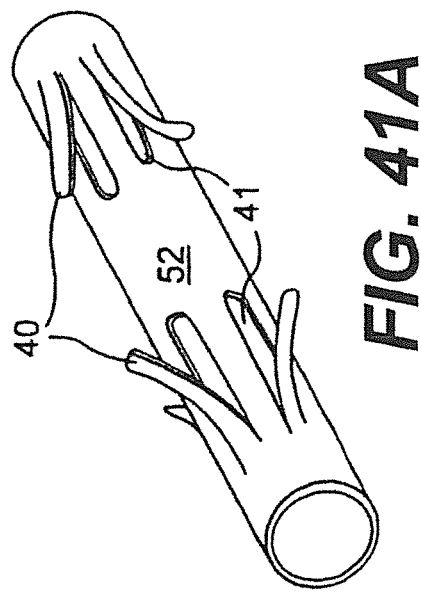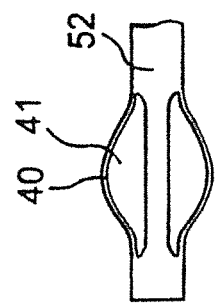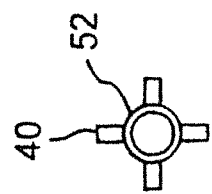

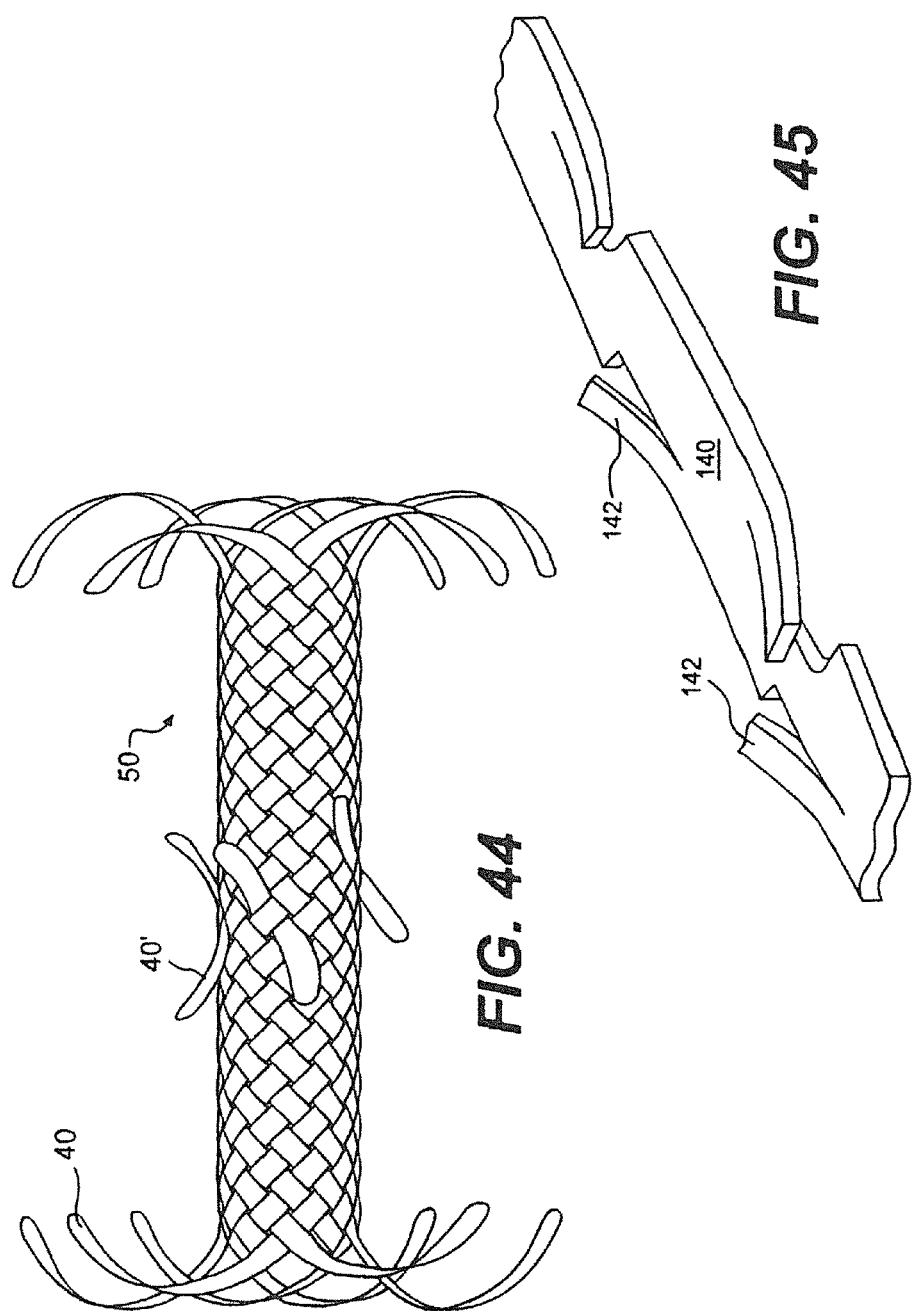

PREVENTION OF MYOCARDIAL INFARCTION INDUCED VENTRICULAR EXPANSION AND REMODELING

PRIORITY APPLICATIONS

This application claims priority to U.S. application Ser. No. 13/116,836, filed May 26, 2011 (allowed), which is a continuation of U.S. Pat. No. 7,988,727, filed Oct. 4, 2004, which is a continuation of U.S. application Ser. No. 10/131, 090, which claims priority to U.S. Provisional Application No. 60/286,521. filed Apr. 27, 2001, the contents of which are incorporated by reference herein in their entirety.

FIELD OF THE INVENTION

The invention relates generally to medical devices and therapeutic methods for their use in the field of interventional cardiology and cardiac surgery, and more specifically to a catheter-based. mini-thoracotomy, or open chest systems to stiffen a myocardial infarction area, to shrink the myocardial infarct region, and/or to reduce wall motion in a peri-infarct and/or infarct region of a heart. The invention also has application in the treatment of mitral valve regurgitation and diastolic dysfunction.

BACKGROUND OF THE INVENTION

Each year over 1.1 million Americans have a myocardial infarction, usually as a result of a heart attack. These myocardial infarctions result in an immediate depression in ventricular function and all of these infarctions are very likely to expand, provoking a cascading sequence of myocellular events known as ventricular remodeling. In many cases, this progressive myocardial infarct expansion and ventricular remodeling leads to deterioration in ventricular function and heart failure.

Post myocardial infarct drug therapy may attenuate many factors that accelerate this remodeling. More recently, medical devices have been developed which provide surgeons with limited tools to support modest intervention with respect to this remodeling situation. However, cardiologists and interventional cardiologists and cardiac surgeons presently lack any devices or procedures for directly attacking this remodeling problem.

A myocardial infarction (MI) occurs when a coronary artery becomes occluded and can no longer supply blood to the myocardial tissue. When a myocardial infarction occurs, the myocardial tissue that is no longer receiving adequate blood flow dies and is replaced with scar tissue. Within seconds of a myocardial infarction, the under-perfused myocardial cells no longer contract, leading to abnormal wall motion, high wall stresses within and surrounding the infarct, and depressed ventricular function. The infarct expansion and ventricular remodeling are caused by these high stresses at the junction between the infarcted tissue and the normal myocardium. These high stresses eventually kill or severely depress function in the still viable myocardial cells. This results in a wave of dysfunctional tissue spreading out from the original myocardial infarct region.

According to the American Heart Association, in the year 2000 approximately 1,100,000 new myocardial infarctions occurred in the United States. For 650,000 patients this was their first myocardial infarction, while for the other 450,000 patients this was a recurrent event. Two hundred-twenty thousand people suffering MI die before reaching the hospital. Within one year of the myocardial infarction, 25% of men and 38% of women die. Within 6 years, 22% of Men and 46% of women develop chronic heart failure, of which 67% are disabled.

The consequences of MI are often severe and disabling. In addition to immediate hemodynamic effects, the infarcted tissue and the myocardium or cardiac tissue undergo three major processes: Infarct Expansion, Infarct Extension, and Ventricular Remodeling. All myocardial infarctions undergo these processes. However, the magnitude of the responses and the clinical Significance is related to the size and location of the myocardial infarction (Weisman H F, Healy B. "Myocardial Infarct Expansion, Infarct Extension, and Reinfarction: Pathophysiological Concepts," Progress in Cardiovascular Disease 1987; 30:73-110; Kelley 8T et al., "Restraining Infarct Expansion Preserves left Ventricular Geometry and Function After Acute Anteroapical Infarction," Circulation 1999, 99: 135-142). Myocardial infarctions that destroy a higher percentage of the normal myocardium and myocardial infarctions that are located anteriorly on the heart are more likely to become clinically significant.

Infarct expansion is a fixed, permanent, disproportionate regional thinning and dilatation of the infarct zone. Infarct expansion occurs early after a myocardial infarction. The mechanism is slippage of the tissue layers.

Infarct extension is additional myocardial necrosis following myocardial infarction. Infarct extension results in an increase in total mass of infarcted tissue. Infarct extension occurs days after a myocardial infarction. The mechanism for infarct extension appears to be an imbalance in the blood supply to the peri-infarct tissue versus the increased oxygen demands on the tissue.

When a myocardial infarction occurs, the myocardial tissue that is no longer receiving adequate blood flow dies and is replaced with scar tissue. This infarcted tissue cannot contract during systole, and may actually undergo lengthening in systole and leads to an immediate depression in ventricular function. This abnormal motion of the infarcted tissue can cause delayed conduction of electrical activity to the still surviving peri-infarct tissue and also places extra mechanical stress on the peri-infarct tissue. These factors individually and in combination contribute to the eventual myocardial dysfunction observed in the myocardial tissue remote from the site of the infarction.

The processes associated with infarct expansion and ventricular remodeling are believed to be the result of high stresses exerted at the junction between the infarcted tissue and the normal myocardium (i.e., the peri-infarct region). In the absence of intervention, these high stresses will eventually kill or severely depress function in the adjacent myocardial cells. As a result, the peri-infarct region will therefore grow outwardly from the original infarct site over time. This resulting wave of dysfunctional tissue spreading out from the original myocardial infarct region greatly exacerbates the nature of the disease and can often progress into advanced stages of congestive heart failure (CHF).

Ventricular remodeling is progressive enlargement of the ventricle with depression of ventricular function. Myocyte function in the myocardium remote from the initial myocardial infarction becomes depressed. Ventricular remodeling usually occurs weeks to years after myocardial infarction. There are many potential mechanisms for ventricular remodeling, but it is generally believed that the high stress on peri-infarct tissue plays an important role. Due to altered geometry, wall stresses are much higher than normal in the myocardial tissue surrounding the infarction. This is depicted in FIG. 2, which illustrates an infarcted region bulging outward from the free waif as compared to the normal heart depicted in FIG. 1. Such bulging is most likely to occur during systole.

Theoretical analysis has shown very high stress levels in the myocardial border with the infarcted tissue (Bogen D. K. et al., "An Analysis Of The Mechanical Disadvantage Of Myocardial Infarction In The Canine Left Ventricle," Circulation Research 1980; 47:728-741). Stress was shown to range 3 to 4 times higher than normal in the peri-infarct region, and the level of stress increase was fairly independent of infarct size, but diminished with increasing infarct stiffness. Three-dimensional reconstructions of the left ventricle were made from short axis fast cine-angiographic computed tomography slices obtained from patients. This analysis showed a higher than normal stress index in the myocardium adjacent to the infarcted tissue (Lessick J. et al., "Regional Three-Dimensional Geometry And Function Of Left Ventricles With Fibrous Aneurysms: A Cine-Computed Tomography Study," Circulation 1991; 84: 1072-1086).

High wall stress can directly damage myocytes. While there are other potential mechanisms, the inventors of the present invention have recognized that the skeletal muscle literature suggested that the high wall stress can lead to cellular dysfunction and damage. This mechanism, as proposed by the inventors as applied to myocytes, is discussed in more detail herein below.

Exertion-induced muscle injury is a well-described phenomenon in skeletal muscle. Prolonged activities that include eccentric contractions or require high stress are more likely to cause injuries. In humans, stretching skeletal muscles during contraction (eccentric contraction) leads to a long lasting muscle weakness (McHugh M P, et ai, "Electromyographic Analysis Of Exercise Resulting In Symptoms Of Muscle Damage." Journal of Sports Sciences 2000; 18:163-72). Muscle biopsies from humans that had performed a step test involving concentric contractions showed muscle damage. This damage was present immediately after exercise, and becomes more noticeable at 1 to 2 days (Newham O J et al, "Ultrastructural Changes after Concentric and Eccentric Contractions of Human Muscle," J. Neurological Sciences 1983; 61:109-122). The 'cellular theory' predicts that the initial muscle damage is the result of irreversible sarcomere strain during high stress contractions. Sarcomere lengths are highly non-uniform during eccentric contractions, with some sarcomeres stretched beyond extremes causing myofilaments to overlap. Loss of contractile integrity results in sarcomere strain and is seen as the initial stage of damage (McHugh M P, et al. "Exercise-Induced Muscle Damage And Potential Mechanisms For The Repeated Bout Effect," Sports Medicine 1999; 27:157-70). Sarcomere abnormalities include disrupted sarcomeres, wavy Z-lines, and sarcomeres with no overlap between myofilaments (Fielding R A, et al, "Effects Of Prior Exercise On Eccentric Exercise-Induced Neutrophilia And Enzyme Release," Medicine and Science in Sports and Exercise 2000; 32:359-64). Myofibrillar disorganization is often focal, with adjacent normally appearing regions (Newham O J, et ai, "Ultrastructural Changes after Concentric and Eccentric Contractions of Human Muscle," J Neurological Sciences 1983; 61:109-122). The longest sarcomeres before high stress contractions are more likely to be damaged (Lieber R L and Friden J, "Mechanisms Of Muscle Injury After Eccentric Contractions," Journal of Science and Medicine in Sport 1999; 2:253-65).

Not only are the muscles damaged, peak force is also decreased. This disease in force occurs immediately after exercise and can persist for several days (Lepers R. et al. "The Effects of Prolonged Running Exercise on Strength Characteristics," International Journal of Sports Medicine 2000; 21:275-80). In one study, peak force was reduced 46% to 58% immediately after high stress-induced injury (Warren G L, et al, "Strength Loss after Eccentric Contractions is Unaffected by Creatine Supplementation," Journal of Applied Physiology 2000; 89:557-62). In mice, after exercise-induced injury, peak force was immediately reduced by 49% partially recovered between 3 and 5 days, but was still depressed at 14 days (−24%) (Ingalls C P, et al, "Dissociation of Force Production from MHC and Actin Contents in Muscles Injured by Eccentric Contractions," Journal Muscle Research Cellular Motility 1998; 19:215-24).

The skeletal muscle literature suggests that muscle tissue can be acutely injured by high stress. The present inventors have realized that stress-induced injury can also occur in cardiac muscle subjected to repeated high stress contractions which occur along the progressive boundaries of an initially-infarcted tissue site. High stresses in the peri-infarct region results in the death or dysfunction of otherwise viable tissue, resulting in a progressive increase in the size of damaged tissue. As new tissue is continuously subjected to high stresses the tissue adjacent to it dies or becomes dysfunctional and results in a new, enlarged peri-infarct region.

DESCRIPTION OF RELATED ART

The treatments for myocardial infarction in the prior art are varied, and generally unsatisfactory. Immediately after a myocardial infarction, preventing and treating ventricular fibrillation and stabilizing the hemodynamics are well-established therapies. Newer approaches include more aggressive efforts to restore patency to occluded vessels. This is accomplished through thrombolytic therapy or angioplasty and stents. Reopening the occluded artery within hours of initial occlusion can decrease tissue death, and thereby decrease the total magnitude of infarct expansion, extension, and ventricular remodeling.

Chronic treatments include surgical approaches to exclude, isolate, or remove the infarct region (such as the Dor procedure). Other potential surgical approaches, requiring the chest to be opened, include the application of heat to shrink the infarcted, scarred tissue, followed by the suturing of a patch onto the infarcted region. Other treatments envision surrounding the heart, or a significant portion thereof, with a jacket. One study (Kelley S T, Malekan R, Gorman J H 3rd, Jackson B M, Gorman R C, Suzuki Y, Plappert T, Bogen O K, Sutton M G, Edmunds L H Jr. "Restraining infarct expansion preserves LV geometry and function after acute anteroapical infarction," Circulation. 1999; 99:135-142) tested the hypothesis that restraining expansion of an acute infarction preserves LV geometry and resting function. In 23 sheep, snares were placed around the distal left anterior descending and second diagonal coronary arteries. In 12 sheep, infarct deformation was prevented by Marlex mesh placed over the anticipated myocardial infarct. Snared arteries were occluded 10 to 14 days later. In sheep with mesh, circulatory hemodynamics. stroke work, and end-systolic elastance return to preinfarction values 1 week after infarction and do not change subsequently. Ventricular volumes and EF do not change after the first week postinfarction. Control animals develop large anteroapical ventricular aneurysms, increasing LV dilatation, and progressive deterioration in circulatory hemodynamics and ventricular function. At week 8, differences in LV end-diastolic pressure, cardiac output. end-diastolic and end-systolic volumes, EF, stroke work, and end-systolic elastance are significant ($P<0.01$) between groups. Prophylactically preventing expansion of acute myocardial infarctions at least has bee~ shown, therefore. to preserve LV geometry and function.

Chronic treatments also include pharmaceuticals such as ACE inhibitors, beta blockers, diuretics, and Ca++ antagonists (Cohn J. N. et al. "Cardiac Remodeling—Concepts And Clinical Implications: A Consensus Paper From An International Forum On Cardiac Remodeling," J. Am Coli Cardiol 2000; 35:569-82). These agents have multiple effects, but share in the ability to reduce aortic pressure, and thereby cause a slight decease in wall stress. These agents have been shown to slow the ventricular remodeling process (St John Sutton M, Pfeffer M A, Moye L, Plappert T, Rouleau J L, Lamas G, Rouleau J, Parker J O, Arnold M O, Sussex B, Braunwald E, "Cardiovascular Death And Left Ventricular Remodeling Two Years After Myocardial Infarction: Baseline Predictors And Impact Of Long-Term Use Of Captopril: Information From The Survival And Ventricular Enlargement (SAVE) Trial," Circulation 1997; 96:3294-9). However, drug compliance is far from optimal. Significant variances exist between published guidelines and actual practice. For example, in treating hyperlipidemia in patients with known coronary artery disease, physician adherence is only 8 to 39% (American Journal of Cardiology 83:1303).

Chronic treatment includes surgical approaches to exclude, to isolate, or to remove the infarct region (such as the Dor procedure). Another potential surgical approach, requiring the chest to be opened, includes the CARDIOCAP made by Acorn Cardiovascular Inc. of St. Paul, Minn. The CARDIOCAP device, a textile girdle or so-called "cardiac wrap," is wrapped around both the left and right ventricles, thereby preventing further enlargement of the heart.

Despite these improvements in therapy, the total number and incidence of heart failure continues to rise with over 400,000 new cases each year. Approximately 85% of these new cases are due to ischemic cardiomyopathy.

Cellular transplantation, introduction of cells into terminally injured heart, can mediate over several weeks islands of viable cells in the myocardium. Several different cell types, ranging from embryonic stem cells, smooth muscle cells, bone marrow cells, cardiomyocytes to autologous skeletal myoblasts, have been successfully propagated within damaged heart and shown to improve myocardial performance (Hutcheson K A. Atkins B Z. Hueman M T. Hopkins M B, Glower D O, Taylor D A. "Comparison Of Benefits On Myocardial Performance Of Cellular Cardiomyoplasty With Skeletal Myoblasts And Fibroblasts," Cell Transplant 2000; 9:359-68; Tomita S, Li R K, Weisel R D, Mickle D A, Kim E J, Sakai T, Jia za, "Autologous Transplantation Of Bone Marrow Cells Improves Damaged Heart Function," Circulation 1999; 100:11247-56; Li R K, Weisel R D, Mickle D A, Jia za, Kim E J, Sakai T, Tomita S, Schwartz L, Iwanochko M, Husain M, Cusimano R J, Bums R J, Yau T M, "Autologous Porcine Heart Cell Transplantation Improved Heart Function After A Myocardial Infarction," J Thorac. Cardiovasc. Surg. 2000; 119:62-8; Scorsin M, Hagege A, Vilquin J T, Fiszman M. Marotte F, Samuel J L, Rappaport L, Schwartz K, Menasche P, "Comparison Of The Effects Of Fetal Cardiomyocyte And Skeletal Myoblast Transplantation On Postinfarction LV Function," J Thorac. Cardiovasc. Surg. 2000; 119:1169•75; Pouzet S, Ghostine S, Vilquin J T, Garcin I, Scorsin M, Hagege A A, Duboc O, Schwartz K, Menasche P, "Is Skeletal Myoblast Transplantation Clinically Relevant In The Era Of Angiotensin-Converting Enzyme Inhibitors?" Circulation 2001; 104:1223-8). Thus, multiple cell lines can be used. While most studies show improvement in left ventricular (LV) function, ejection fraction (EF), decreased end diastolic volume (EDV) and end systolic volume (ESV), the mechanism for these improvements is unknown.

Interestingly, most studies show increased wall thickness in scar and a stiffer LV. Transplanted smooth muscle cells limited LV dilatation and improved heart function. These results are consistent with the transplanted smooth muscle cells limiting scar expansion, preventing ventricular dilatation, and over-stretching of the cardiomyocytes during systole (Li R K, Jia Z Q, Weisel R D, Merante F, Mickle D A, "Smooth Muscle Cell Transplantation Into Myocardial Scar Tissue Improves Heart Function," J. Mol. Cell Cardiol. 1999; 31:513-22).

To quote the study by Etzion and colleagues, "The mechanism behind these encouraging effects remains speculative. Direct contribution of the transplanted myocytes to contractility is unlikely based on our histological findings. Benefits may be associated with enhanced angiogenesis, attenuation of infarct expansion by virtue of the elastic properties of the engrafted cardiomyocytes. It is possible that the beneficial effect of the engrafted cells is due to increasing ventricular wall thickness, which, according to Laplace's law, will reduce LV wall stress and should prevent infarct expansion, LV dilatation and deterioration of function." (Etzion S, Batler A, Barbash 1M, Cagnano E, Zarin P, Granot Y, Kedes L H, Kloner R A, Leor J, "Influence Of Embryonic Cardiomyocyte Transplantation On The Progression Of Heart Failure In A Rat Model Of Extensive Myocardial Infarction," J. Mol. Cell Cardiol. 2001; 33:1321-30).

Since multiple cell lines and even non-contracting cells can improve LV function, and since increased scar thickness is consistently observed, the mechanism for improved function with cell transplantation may be due to increased stiffness of the infarcted tissue. From previous theoretical analysis, this increased stiffness should decrease myocardial wall stress.

The present inventors have also recognized that certain results obtained from patients with left ventricular assist devices (L VADs) indicate the importance of high stress in the etiology of the myocyte dysfunction secondarily to myocardial infarctions. The observations from patients with L VADs support an argument for the importance of high stress in the etiology of global and myocyte dysfunction secondary to myocardial infarctions. In heart failure, not only is global function severely depressed, the individual myocytes are also depressed with altered gene expression and receptor regulation. Patients, awaiting heart transplantation, have received LVAD support. At the time of heart transplantation, cells have been isolated from the diseased hearts. With LVAD support, the myocyte cell function, gene expression, and receptor regulation tend to return towards normal. The LVAD reduces the wall stress on the myocardial cells. The implication is that high wall stress plays a central role in inducing cell failure or conversely decreasing wall stress leads to improved cell function.

The catheter-based approach for the introduction of devices or agents into the cardiac space can take advantage of current techniques to identify the ischemic myocardium, to position catheters within the left ventricular cavity, to insert devices onto or into the myocardium, and/or to inject material into a coronary artery or vein.

With percutaneous transmyocardial revascularization (TMR) and gene therapy, systems have been developed to assess and to distinguish normal, ischemic and non-viable, and ischemic but viable myocardial tissue.

The main focus of TMR is to increase perfusion in myocardial tissue that is ischemic, but still viable, and not to create channels in normal myocardial tissue. In gene therapy to increase revascularization, a similar need to identify ischemic, viable myocardial tissue exists. While in cell transplantation, the intent is to seed the ischemic, non-viable myocardial tissue with new cells.

Multiple technologies and approaches are available today for the clinician to assess normal, ischemic-non-viable, and ischemic-viable myocardial tissue. These include, but are limited to, localized blood flow determinations, local electrical and mechanical activity, nuclear cardiology, echocardiographic stress test, coronary angiography and ventriculography.

Localized blood flow determinations: Researchers in medical science have known that the rate of blood flow within a tissue can be measured by a process of heating a device. such as a probe, which is in contact with the tissue being examined, and then recording the temperature changes by a thermocouple positioned in or near the probe. The recorded temperature changes are representative of the blood flow in the tissue. The heated device and thermocouple effectively act as a flow meter for determining the blood flow as a function of the rate at which heat is carried away from the tissue.

Heated probes and thermocouples used for the determination of blood flow were first introduced by F. A. Gibbs in 1933 for the purpose of measuring flow in blood vessels. Gibbs' experiment is described in Proc. Soc. Exptl. Biol. Med. 31; 141-147, 1933, entitled, "A Thermoelectric Blood Flow Recorder In The Form Of A Needle." Heated probes and thermocouples were later used as flow meters by C. F. Schmidt and J. C. Pierson for measuring blood flow in solid organs. Schmidt's and Pierson's efforts are described in the Am. J. Physio!., 108; 241, 1934, entitled, "The intrinsic regulation of the blood flow of medulla oblongata." Further investigation by J. Grayson and his colleagues described in Nature 215: 767-768, 1967, entitled. "Thermal Conductivity of Normal and Infarcted Heart Muscle," demonstrated that a heated probe with a thermocouple could be used in accordance with a certain relation, known as Carslaw's equation, to measure the thermal conductivity (k) of any solid, semisolid, or liquid in which the heated probe and thermocouple were inserted. Carslaw's equation is discussed in detail in the Journal of Applied Physiology, Vol. 30, No. 2, February 1971, in an article entitled, "Internal calorimetry Assessment of Myocardial Blood Flow and Heat Production."

A heated coil about a thermistor may also by used as an effective flow meter as described in a Technical Note entitled, "Thermal Transcutaneous Flowmeter," by D. C. Harding, et al., published in Med. & Biol. Eng., Vol. 5, 623-626, Pergamon Press, 1967.

"Heated" thermocouples or thermistors used in flow meters, function to provide heat essentially by conduction to the tissue in immediate contact with the heating device, and measure the temperature of that tissue. Determination of fluid (blood) perfusion heretofore was limited by the heating of tissue essentially in contact with a heated device.

U.S. Pat. No. 4,228,805 issued to Rosen and Santamore describes irradiating tissue with a microwave signal having a predetermined repetition rate, amplitude and frequency, to elevate the temperature of a volume of the tissue to a predetermined temperature and measuring the rate of decay of the temperature of tissue, which decay is indicative of thermal conductivity of the volume of tissue and thus the fluid perfusion of the volume of tissue.

U.S. Pat. No. 6,277,082 issued to Gambale describes an ischemia detection system by temporarily altering the temperature of the tissue and then monitoring the thermal profile of the tissue as it returns to normal temperature. Tissue areas of slower response time correspond to areas of reduced blood flow (ischemia).

Electrical and Mechanical Activity: This approach uses three external reference points generating low-magnetic field energy to locate the position of a catheter in the body. The tip of the catheter is positioned against the left ventricular endocardial surface. Based on the motion of the tip of the catheter throughout the cardiac cycle, regional wall motion is assessed: greater motion indicating normal regions and lesser wall motion indicating ischemic regions. Local myocardial electrical activity, either unipolar or bipolar, measured at the catheter tip indicate normal (higher peak-to-peak QRS voltage) or ischemic (lower peak-to-peak QRS voltage) myocardium. Myocardial tissue with high wall motion scores and high electrical potentials is considered to be normal tissue. Myocardial tissue with low wall motion scores, but moderate electrical potentials is considered to be ischemic, but viable tissue. Myocardial tissue with low wall motion scores and low electrical potentials is considered to be ischemic, non-viable tissue.

For myocardial perfusion imaging with the single photon emission tomography, or SPECT, technique, dual-isotope imaging is generally performed with 201T1 (Thallium 201) for rest and $^{99m}T_c$ sestamibi for stress imaging. Under resting conditions, 201T1 is administered intravenously. Patients are positioned in a standard SPECT camera in the supine position, and rest imaging is performed beginning 15 minutes after thallium injection. After completion of acquisition of the rest images, subsequent imaging is performed using pharmacological (i.e., adenosine administration) stress. $^{99m}T_c$ sestamibi is administered at peak vasodilator effect. Stress imaging is performed beginning 60 minutes after sestamibi injection. In patients with a suspected or objectively determined irreversible perfusion defect, who might have reduced perfusion at rest to viable tissue, redistribution images of the rest thallium data are performed. This is achieved by a second acquisition of thallium data at 3 to 4 hours to represent redistribution activity. After the rest-redistribution thallium study, the patient undergoes stress imaging as indicated above.

Typically, short-axis image slices are selected for interpretation, representing basilar, midventricular, and apical levels of the LV. The mid and basilar short-axis slices are subdivided into 4 segments representing the anterior, anteroseptal, inferoposterior, and lateral regions, similar to the subdivision obtained by the LV electromechanical mapping. A qualitative assessment for these 9 segments (normal, reversible defect, fixed defect) is performed for both the rest thallium and stress sestamibi data sets.

Echocardiograph provides real-time single, two-dimensional, and soon three-dimensional views of the heart. From these visual images, regional ventricular wall motion is determined. Myocardial infarction causes abnormalities in regional wall motion, which can be assessed by echocardiography. Additionally, echocardiographic contrast agents are available, which can be used to assess regional blood flow.

In the cardiac catheterization laboratory, the lesion responsible for the myocardial infarction can be identified together with the abnormal wall. Via an artery (commonly the femoral artery), a catheter is positioned by the—left main coronary artery. Contrast material is injected into the coronary arteries and the lesion responsible for the myocardial infarction identified; i.e., the lesion that is causing the obstruction to flow.

It is accordingly a primary object of the invention to provide therapeutic devices and methods for the mechanical treatment of myocardial infarction.

The present invention contemplates an intervention being taken to prevent further deterioration of cardiac tissue surrounding an infarction, preferably such intervention being taken immediately following an MI event. This is achieved by mechanically supporting an infarct and/or peri-infarct region to prevent processes associated with infarct expansion and ventricular remodeling as the result of high stresses exerted at the junction between the infarcted tissue and the normal myocardium. In the absence of intervention, these high stresses will eventually kill or severely depress function in the myocardial cells. This resulting wave of dysfunctional tissue spreading out from the original myocardial infarct region greatly exacerbates the nature of the disease.

At present, there are no simple mechanical procedures available to treat myocardial extension, and no catheter-based or mini-thoracotomy procedures to treat myocardial extension and ventricular remodeling.

SUMMARY OF THE INVENTION

In accordance with the invention, devices and methods are provided for an effective intervention to interrupt the propagation of dysfunctional tissue in the. myocardium. This therapy can be used to prevent a variety of heart pathologies.

Disclosed are devices and methods for direct, localized, therapeutic treatment of myocardial tissue in heart having a pathological condition including identifying a target region of the myocardium; and followed by applying material directly and substantially only to at least a portion of the myocardial tissue of the target region substantially identified to physically modify the mechanical properties of said tissue.

A further object of the invention is to reduce the abnormal geometry and wall stress placed on the infarct and peri-infarct tissue. This is achieved in several ways, as will be set forth herein below. Motion in the peri-infarct region is limited through application of aspects of the present invention. The infarct region is made stiffer, thereby altering the geometry and wall stress on the peri-infarct tissue through the application of aspects of the present invention. Stiffening of the infarct region, among other benefits, limits systolic elongation of the infarcted tissue preventing local enlargement of the left ventricle, thereby improving cardiac function. Lastly, the infarct region is effectively excluded or shrunk through application of aspects of the present invention.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIGS. 5A through 5D depict alternative embodiments according to one aspect of the invention.

FIGS. 6A and 6B depict the placement of illustrative embodiments according to one aspect of the invention in the myocardium.

FIGS. 7A through 7H depict alternative embodiments according to one aspect of the invention.

FIG. 8 depicts representative placement of embodiments of the invention surrounding an infarcted region of a heart.

FIGS. 16A through 16F depict a heart including an infarcted region in response to the embodiment of the present invention depicted in FIGS. 15A and 15B.

FIG. 17 depicts a still further aspect of the present invention where embodiments are introduced into the endocardium.

FIGS. 35A through 35E show a further exemplary embodiment of the present invention including a method for insertion involving a coil.

FIGS. 37A through 37D show a further exemplary embodiment of the present invention.

FIG. 39 shows a further exemplary embodiment of the present invention.

FIGS. 40A and 40B show end configuration views for an alternative device as depicted in FIG. 39.

FIGS. 41A through 41F show configurations for an alternative device similar to the embodiment depicted in FIG. 39.

FIG. 44 shows a modification of the embodiment depicted in FIG. 43 having barbs on a midsection of the body.

FIG. 45 is a magnified view of an illustrative wire material used to make the braided devices of FIGS. 43 and 44 including barb features along its length.

DESCRIPTION OF ILLUSTRATIVE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The present invention serves to reduce the abnormal geometry and wall stress placed on the peri-infarct and/or infarct tissue. This is achieved in several ways, which will be described with reference to illustrative embodiments.

As a general proposition, the present invention limits motion in the peri-infarct and/or infarct region. Thereby, the infarct region is made stiffer, thereby altering the geometry and wall stress on the peri-infarct tissue. Thereby, the infarct region is effectively excluded or shrunk.

Figure 1:
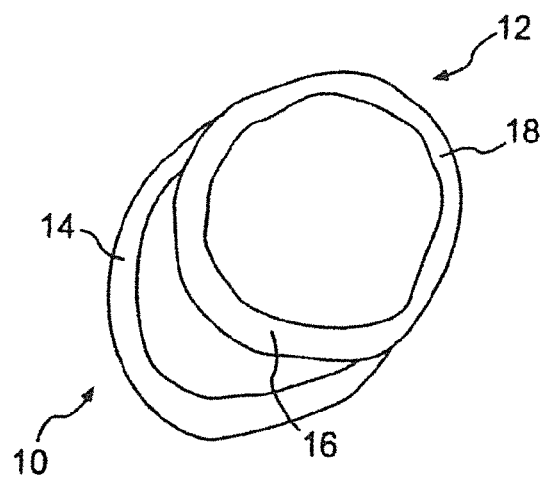
FIG. 1 is a cross sectional depiction of a normal heart.
Figure 2:
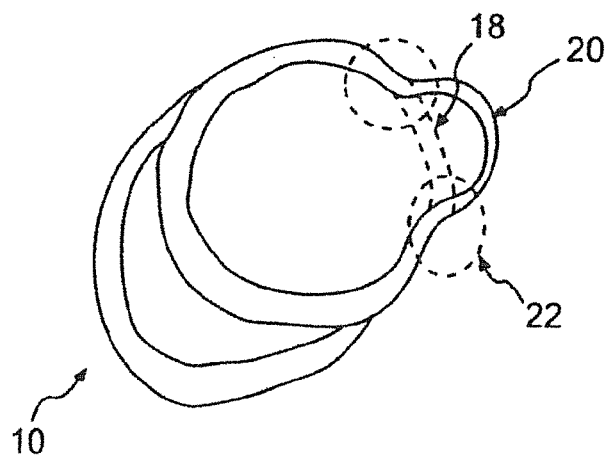
FIG. 2 is cross sectional depiction of a heart showing an infarcted region on the free wall of the left ventricle.

As discussed hereinabove, within seconds of a myocardial infarction. Underperfused myocardial cells no longer contract, and actually lengthen during systole leading to abnormal wall motion, high wall stresses within and surrounding the infarct, and bulging in the ischemic regions. FIG. 1 schematically shows a heart 10 having a left ventricle 12 and right ventricle 14, the ventricles separated by septal wall 16. The contraction of the normal heart occurs with the ventricular walls moving towards the center, resulting in the ejection of blood from the left ventricle. The left ventricular free wall 18 is shown in FIG. 1 having a normal configuration. When a myocardial infarction occurs, the infarcted tissue of free wall 18, shown in broken lines to represent its normal configuration, tends to extend outwardly to form a bulge 20, as schematically depicted in FIG. 2. This is especially true during systole. This results in an abnormal geometry at the peri-infarct region, which in turn causes higher than normal wall stresses in the peri-infarct regions 22. These high stresses together with delayed electrical activation of the tissue lead to abnormal wall motion. and even lengthening of the myocytes in the peri-infarct region during systole. As stated above, these high wall stresses, altered geometry, and eccentric contractions lead to myocyte dysfunction.

The present invention has as one of its objects to restrict motion in the periinfarct and/or tissue; i.e., to eliminate or limit expansion of the peri-infarct tissue during systole. Otherwise, the still-viable myocardial cells must shorten more than normal to compensate for this wasted, abnormal wall motion in the infarct region, and further, such extra shortening occurs against a higher wall stresses.

Figure 3A:
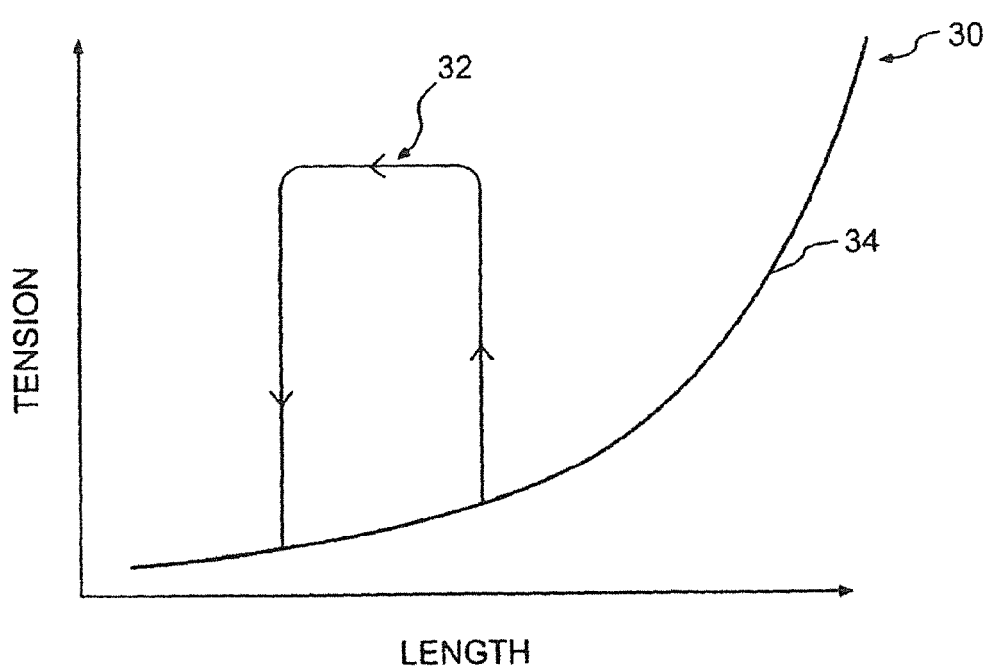
FIG. 3A graphically depicts the relationship between tension and myocardial tissue length during systole and diastole and FIGS. 3B through 3e propose a physiological model.

The abnormality of infarct tissue wall motion will be appreciated by reference to FIG. 3, which graphically depicts the relationship between tension and tissue length for normal and myocardial infarct tissue. In its passive or diastolic phase 30, normal myocardial tissue has an exponential relationship between tension and tissue length. As the tension on the tissue increases, the length of the tissue increases. In normal myocardial tissue during active contraction (systole), tension in the tissue increases, while the length of the tissue decreases. This active contraction results in a tension-length loop 32. In myocardial infarct tissue, the cardiac myocytes no longer actively shorten during systole. Instead, the tissue primarily behaves passively and lengthens in systole as the left ventricular pressure and wall stress increase as shown by line 34, which closely approximates the trace of passive line 30.

The inventors propose that the cellular stretch of myocardial tissue under stress causes the eventual bending in the infarct region, which leads to the cascading physiological degradation of cardiac function following infarction. FIG. 3b depicts normal myocytes 24 in relation to capillaries 25.

Under stress, the myocytes lengthen and expand as shown in FIG. 3c, collapsing the capillaries and therefore obstructing the flow of blood to the myocytes. As shown in FIG. 3d, the eventual formation. of fibrous tissue between the myocytes as a long-term response to stress causes myocellular rearrangement, and fewer myocytes per unit volume of wall tissue. FIG. 3e shows that bending at points 27 resulting from the cellular stretching. This is a direct result of the myocellular increase in length and diameter as a response to stress at the border zone of the infarct region 21.

Figure 4A:
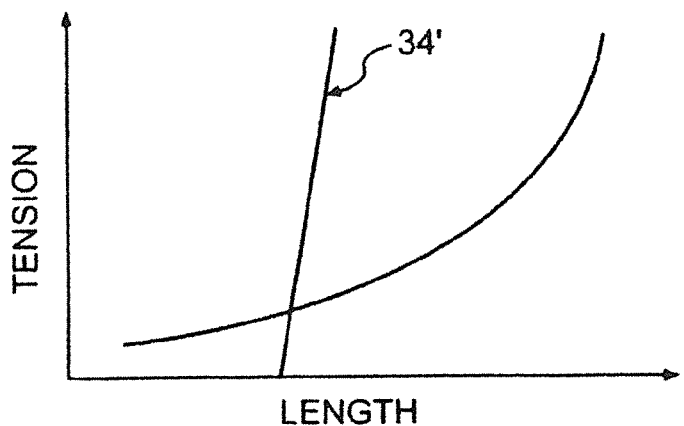
FIGS. 4A, 4B and 4C graphically depict the relationship between tension and myocardial tissue length according to aspects of the present invention.
Figure 4B:
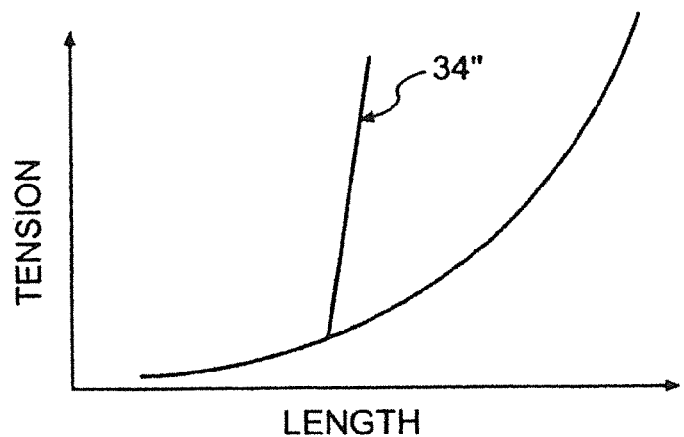
Figure 4C:
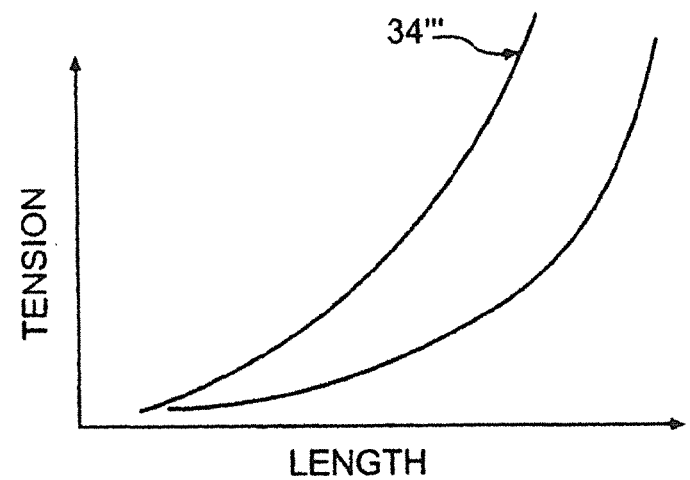

According to the present invention, regional passive tissue characteristics can be altered, for example, by three approaches that will be discussed herein; stiffening, restraining, or constraining. FIG. 4a shows an example of stiffening the tissue. Here the normal exponential relationship between tension and length is converted into almost a straight line 34' in very stiff tissue. The length of the tissue changes little, if at all, over a very wide range of tension; i.e., the length is almost independent of the pressure in the ventricle. FIG. 4b shows an example of restraining the tissue. Here the normal exponential relationship between tension and length exists until the tissue reaches an upper length limit. At this length, any further lengthening of the tissue is prevented and the tension-length relationship becomes almost a straight line 34". The length of the tissue changes little, if at all, above this length. FIG. 4c shows an example of constraining the tissue. Here the normal exponential relationship between tension and length is shifted to the left as shown by line 34'''. At every length, a higher tension is required to stretch the tissue to that length.

In practice, the devices disclosed herein to stiffen, restrain, or constrain tissue will not have the ideal characteristics depicted in FIGS. 4a, 4b, and 4c, and can have a combination of effects. For example, the tissue will encapsulate a restraining device. This encapsulation will stiffen the tissue. The anchoring points on the devices will further add to this encapsulation, and thus stiffening of the tissue. Thus, the devices described below can be combinations of stiffening, restraining, and constraining components.

Devices that stiffen, restrain, or constrain the tissue have two main components, anchors and a body. Additionally, the devices can have a bend point. As described later, these bend points allow the devices to restrain or constrain the tissue, while not forcing the tissue into a straight structure.

FIG. 5a shows multiple exemplary anchors for devices according to the present invention. These exemplary anchors 40 hold the device in position within the tissue. The anchors depicted are in the shapes of a fishhook 42, a cone 48, an umbrella 49, barbs 44, or screws 46. Other anchor types would know to those familiar with the art. To add to the holding strength, multiple anchors are used alone the length of a device 50, as depicted in FIG. 5b, which includes at least one body 52, an anchor 40 and may also have a bend 54. The anchors can be made of shape memory material. As shown in the illustrative constraining device of FIG. 5c and the illustrative combination device of FIG. 5d, multiple anchor types can be used in the same device, and the body may take the form of a spring 56.

As above, multiple anchor types can be used in the same device. The body 52 can be spring-like in structure, and is made from polymers or medal material. This spring-like structure pulls the anchor points closer together: the greater the distance between the anchor points. the greater the force on the anchor points from the spring-like body structure. The bend points enable the direction between anchor points to change slightly. This enables the tissue to be constrained while still maintaining an arc shape.

FIG. 5d shows a combination device within the myocardial tissue. This device consists of multiple anchors, body parts, and bend points. The anchors and part of the device can be placed in normal non-infarcted myocardial tissue. Multiple anchor types are used in this device. Some body parts primarily restrain the tissue and are made from suture, polymers, or medal wire material. Other spring-like body parts primarily constrain the tissue, and are made from polymers or medal material. The bend points enable the direction between anchor points to change slightly. This enables the tissue to be restrained and/or constrained, while still maintaining an arc shape. Obviously. many combinations of anchors and body parts are achievable to those familiar in the arts.

Turning now to FIGS. 6a and 6b. there is depicted the myocardium 15 showing the epicardium 15' superiorly and the endocardium 15" inferiorly. A bulge 20 manifests an infarct region 21, surrounded by a peri-infarct region 22. Devices 50 are placed through the myocardium 15, thereby restricting motion in the peri-infarct 22 or infarct 21 regions. Devices 50 may be referred to as "buttons" or "clamshells" according to an illustrative embodiment depicted here, but any device 50 can be deployed as shown. Similar to the previously described embodiments. devices 50 comprise multiple anchors 40, a body 52, and bend points 54. The anchors and part of the device can be placed in normal non-infarcted myocardial tissue. Since the devices do not restrain normal diastolic length and since the devices do not inhibit shortening, the devices have minimal. if any, effect on function in normal tissue. The body 52 can be made from suture, polymers, or medal wire material. The material allows the anchor points to move closer together, but restricts the maximal distance between the anchor points. The bend points enable the direction between anchor points to change slightly. This enables the tissue to be restrained, while still maintaining an arc shape.

FIG. 7 depicts various illustrative embodiments of restraining devices in the form of clamshells or button type devices. Clamshells or buttons can be deployed from one side or from both sides of the myocardium (i.e., endocardium and epicardium). When deployed in the peri-infarct region as shown in FIGS. 6a and 6b, these devices with their inherent stiffness restrict motion of the tissue in the peri-infarct region. Also, adhesions between the devices and the surrounding tissue promote stiffness as well. Several of these devices, as shown in FIGS. 7a through 7g can be placed around the infarcted tissue as shown in FIG. 8. FIG. 7b shows the tilting bend 54 and FIG. 7e depicts a spring-loaded embodiment. In one embodiment. the device is similar to prior art clamshell like devices that are used to close atrial and ventricular septal defects, such as the button device depicted in FIG. 7h.

In practice, these devices are placed either during a percutaneous, minithoracotomy, or during an open chest approach. In the percutaneous approach, a catheter is introduced into a blood vessel, such as the left or right femoral artery, and advanced into the heart, for example the left ventricle. An exemplary device which could be adapted in the practice of the present invention is disclosed in U.S. Pat. No. 6,071,292 to Makower, specifically in FIGS. 7 through 14 thereof. The entirety of the Makower patent is incorporated herein by reference.

The infarcted tissue must be identified and located on the heart. There are many clinical means known in the art to identify and locate infarcted heart tissue. The occluded coronary artery that caused the myocardial infarction is also identified using known methods. The occluded artery, the region of the heart perfused by this artery, and thus the infarcted tissue, are naturally related.

Further, infarcted heart tissue has unique characteristics: no or minimal electrical activity, different electrical impedance properties, abnormal wall motion, and abnormal metabolic activity. Each of these is used individually or in combination to identify the infarcted tissue. In one approach, a catheter(s) deployed in the left ventricle has electrodes at its tip. By positioning the catheter(s) against the left ventricular endocardial border and recording the local electrical activity, infarcted tissue is recognized (i.e., through observing very low electrical potentials) (Callans, D. J. et al., "Electroanatomic Left Ventricular Mapping In The Porcine Model Of Healed Anterior Myocardial Infarction: Correlation With Intracardiac Echocardiography And Pathological Analysis," Circulation 1999; 100:1744-1750). In another approach, the catheter has several small electrodes by its tip. These electrodes measure the local electrical impedance of the tissue by the catheter's tip. Infarcted myocardial tissue impedance is significantly lower than the impedance of normal myocardial tissue (Schwartzman D. et al., "Electrical Impedance Properties Of Normal And Chronically Infarcted Left Ventricular Myocardium," J. Intl. Cardiac Electrophys. 1999; 3:213-224; Cinca J. et al., "Passive Transmission Of Ischemic ST Segment Changes In Low Electrical Resistance Myocardial Infarct Scar In The Pig," Cardiovascular Research 1998; 40:103-112). Again, these approaches can be combined: the same electrodes that measure local electrical activity also measure local electrical impedance. The contents of these publications are incorporated herein by reference.

Once the infarcted tissue is identified, a catheter can be positioned by the border between the infarcted and normal tissue. The catheter can then be directed to the desired endocardial surface. As illustrated in FIG. 7b, the button or clamshell in its collapsed position is similar to an umbrella for deployment. The collapsed device is then pushed through the myocardium. Once fully positioned and released from the catheter, the device is expanded to its full open position. A tether wire (not shown) attached to the device can be used to pull the button or clamshell against the epicardial surface or to otherwise position the device in situ. A second button or clamp shell can be similarly deployed on the endocardial border. The wire body between the two buttons or clamp shells keeps the devices in contact with the epicardial and endocardial borders. The device can be dimensioned to restrain the cardiac wall under tension for stiffening. Once positioned, the catheter releases and is removed.

In another embodiment, the device is placed by a mini-thoracotomy approach. Mini-thoracotomy or minimally invasive surgery uses very small incisions or access ports. For example, three or four ports provide access to the chest, including one for a video camera, one for light, and one or two for instruments. The instrument port allows multiple instruments to be used. Known prior art instruments can be used to access the epicardial surface of the heart, and identify the infarcted tissue. A deployment instrument can then be placed in the chest. The infarcted region is identified as previously described. The device is positioned at the border of the infarcted tissue, and the device(s) deployed.

In another embodiment. the device can also be deployed during open chest surgery. This is either as a sole therapy or in conjunction with other procedures, such as coronary artery bypass surgery.

Figure 9F:
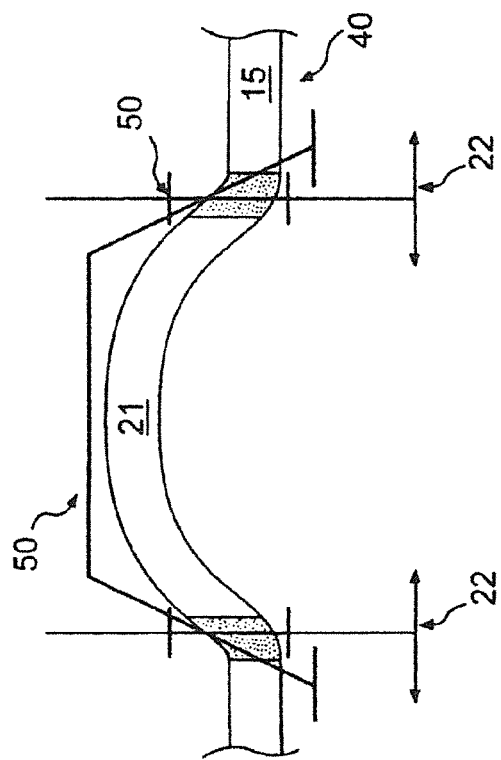
FIGS. 9A through 9C depict alternative embodiments according to another aspect of the invention.
FIG. 9D depicts representative placement of embodiments of the invention surrounding an infarcted region of a heart and FIGS. 9E through 9G further illustrates alternative embodiments of the invention and their representative placement.

FIGS. 9a through 9g presents another means to restrict motion in the infarct and peri-infarct region. Clamshells or button-like devices 50 are placed on the endocardial border. A wire or other body portion 52, connected to one anchor 40, passes through the myocardium 15 in the infarct 21 or peri-infarct 22 region as shown in FIGS. 9c and 9b, respectively.

Figure 9G:
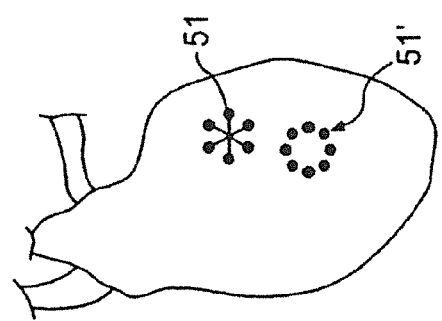
Figure 9E:
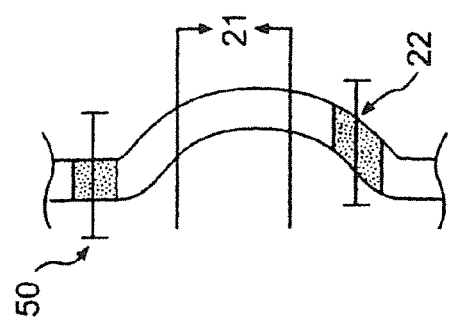

As shown in FIGS. 9a and 9b, the body portion 52 can cross over or through part of the infarcted tissue and then pass through the myocardium and connect with another anchor. The inherent stiffness of the wire body together with adhesions with the surrounding tissue limit motion in the infarct region and the peri-infarct region. As depicted in FIG. 9c, the wire can pass through the myocardium. In one embodiment. this stiffening wire body 52 is positioned within the infarcted and myocardial tissue, and never exits the tissue on the epicardial surface. Further, while FIG. 9a shows the anchor 40 in direct contact with the endocardium. FIGS. 9b and 9c show that indirect contact is also possible, leaving a space B as indicated in FIG. 9b. A plurality of such devices can be placed around an infarct in a cluster 51 as shown in FIG. 9d. FIG. 9e depicts devices 50 placed through the peri-infarct region 22 only. FIG. 9f shows an embodiment of FIG. 6a in the myocardium 15 with an embodiment of FIG. 9b. Such coplacement allows, for example, the restraining motion of the peri-infarct tissue, while stabilizing the infarct entire region. As with all embodiments according to the invention, these can be used singularly, in plurality, or in combination with other embodiments. FIG. 9g illustrates a cluster 51 as depicted in FIG. 9d alongside a cluster 51' of devices which are not attached as depicted in FIG. 9b.

These devices are placed either through a percutaneous, mini-thoracotomy, or open-chest approach. The infarcted tissue is located, as previously described.

Figure 10B:
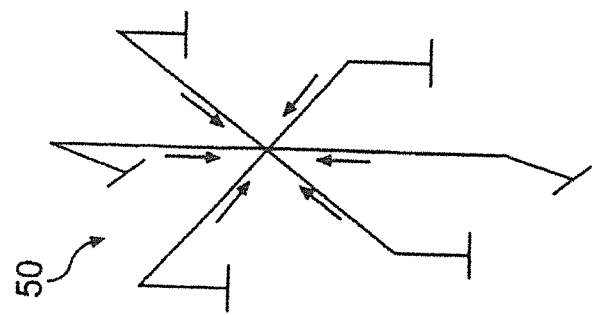
FIGS. 10A and 10B depict alternative embodiments according to one aspect of the invention.
Figure 10C:
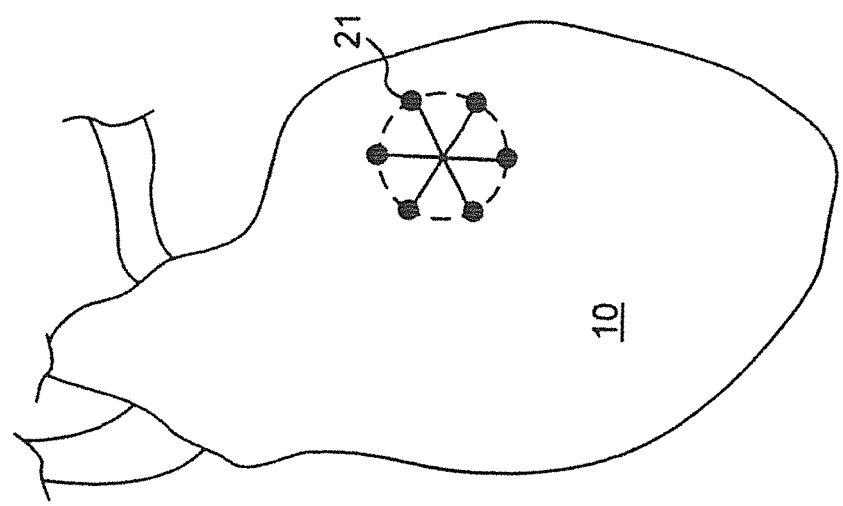
FIG. 10C depicts representative placement of embodiments of the invention surrounding an infarcted region of a heart.
Figure 10A:
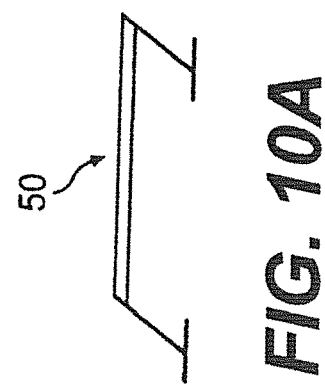

FIGS. 10a and 10b show variants of the devices illustrated in FIGS. 9a and 9b. In FIG. 10c, the device 50' as depicted in FIG. 10b is shown placed in the heart 10 surrounding an infarct region 21.

Figure 11A:
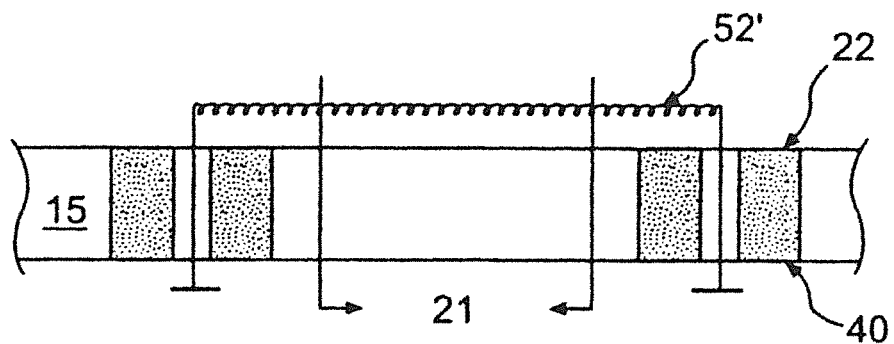
FIGS. 11A and 11B illustrate alternative embodiments of the invention and their representative placement.
Figure 11B:
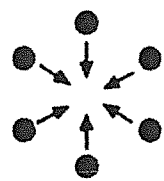

Turning now to FIG. 11a, device 50 is depicted having a spring tensioned body 52', or retaining member, connecting two anchors 40. As shown in FIG. 11 b, the use of spring-loaded members singularly or in a cluster as shown. will stabilize the peri-infarct zone 22 and may shrink tissue toward the center of the infarct region 21, or it may prevent expansion. The retaining member can be passive or made to return toward a less-expanded state, through the use of shape memory materials for example, thereby shrinking the infarct region.

Figure 12A:
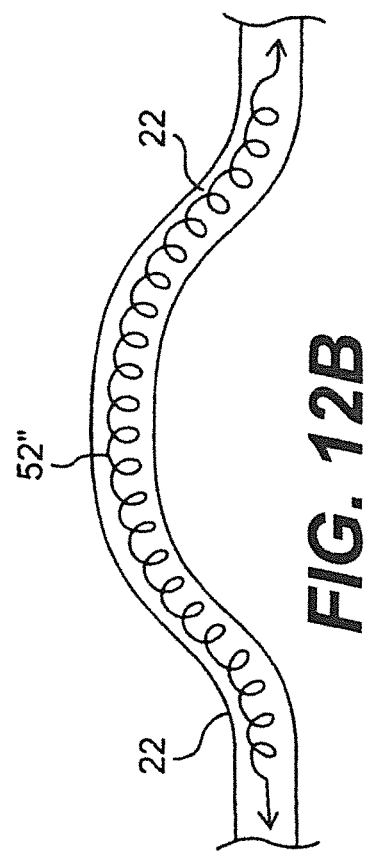
FIG. 12A depicts an alternative embodiments according to another aspect of the invention.
Figure 12B:
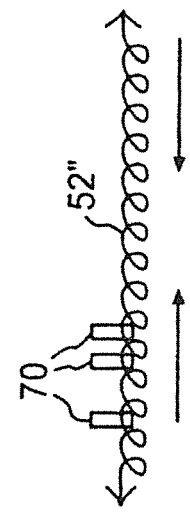
FIGS. 12B and 12C depict representative placement of these embodiments of the invention in the heart.
Figure 12C:
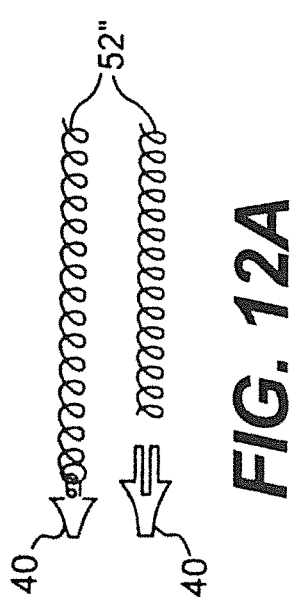
Figure 12D:
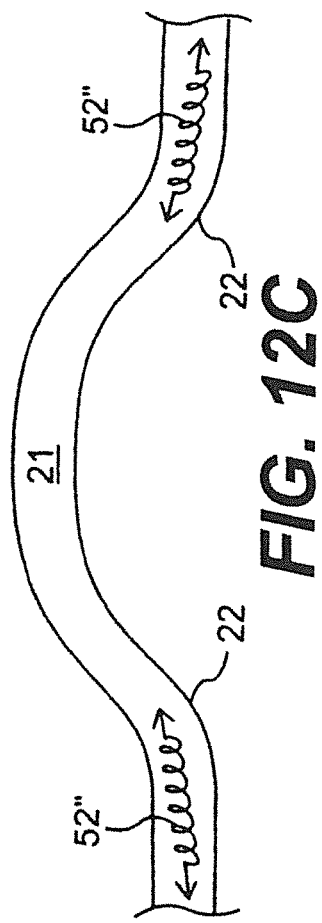
FIG. 12D depicts a modification using spacers.

Turning now to FIG. 12a, a device 50 is shown having yet another means to restrict motion in the infarct and peri-infarct region. A device having a spring-like body 52" attached to an anchor 40, or a detachable anchor 40', is placed from the normal myocardial tissue 15 across the peri-infarct 22 region and into the infarcted tissue 21 as shown in FIGS. 12b and 12c. Buttons, cones, or similar anchor structures 40, 40' at either end of the spring 52" grab the surrounding tissue. The spring is deployed in a relaxed or in a pre-stretched condition. In its relaxed state, the spring-like device resists extension in this region. For the pre-stretched condition, the spring can be kept in a biased state by a stiff wire member in the center of the spring. Once deployed, this wire is cut or removed allowing the spring to shorten. In another exemplary embodiment shown in FIG. 12d, the spring 52" is kept in this pre-stretched condition by spacers 70, which can be formed from bio-absorbable material, placed between the coils. Over time, the material dissolves and is absorbed and the spring is allowed to shorten under its bias in the direction of arrow A as shown in FIG. 12c. Once allowed to shorten, the device not only resists extension, but also resiliently pulls the tissue together throughout the cardiac cycle. The spring 52 with the bio-absorbable material 70 in one embodiment resembles a standard clinical guidewire in appearance, as seen for example in FIG. 12d. The bio-absorbable material can have different absorption rates. Several of these spring devices are placed into the infarct tissue to reduce the infarct size. These springs may be made of fibers that have mechanical characteristics that pull the ends closer together, thereby shrinking the infarct tissue. This pulling together can occur rapidly (seconds to hours) and/or gradually over days to months. This pulling together shrinks the infarct size and decreases wall stress in the peri-infarct tissue. Metals exhibiting shape memory and/or martensitic-austenitic transitions at body temperature can also be employed.

These devices can also be placed either through a percutaneous, minithoracotomy, or open-chest approach. The infarcted tissue is located as previously described. For the percutaneous approach, a catheter is positioned in the left ventricle, placed against the endocardial surface, and the infarct tissue identified. The spring-like device is inserted into the myocardium. For the pre-stretched condition, the wire is removed, thereby allowing the spring to pull the tissue together. Once properly deployed, the catheter is removed. Several of these spring-like devices are placed in the peri-infarct and/or tissue. For the mini-thoracotomy or open-chest approaches, the devices are placed through similar techniques.

Figure 13:
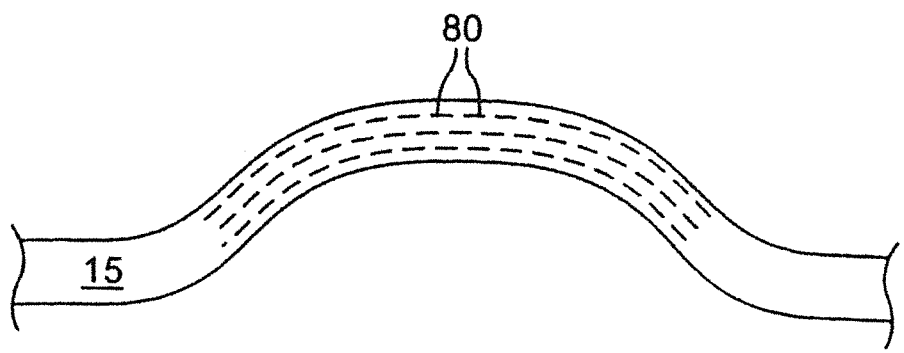
FIG. 13 depicts an alternative embodiment according to another aspect of the invention and representative placement of embodiments of the invention in an infarcted region of a heart.

FIGS. 13 through 16 depict still further embodiment of the invention. FIGS. 13 and 15a depict a cross section of the myocardium 15, in which particles or rods 80 have been injected into the infarcted tissue either alone as in FIG. 13 or in a matrix 82 of biocompatible material as shown in FIG. 15a. These particles by their inherent mechanical properties and by becoming encapsulated stiffen the tissue. By stiffening the tissue, the altered geometry and high wall stress in the peri-infarct region is reduced. The stiffened tissue resists outward bulging in systole, which in turn, reduces or prevents altered geometry by the peri-infarct zone.

Figure 14:
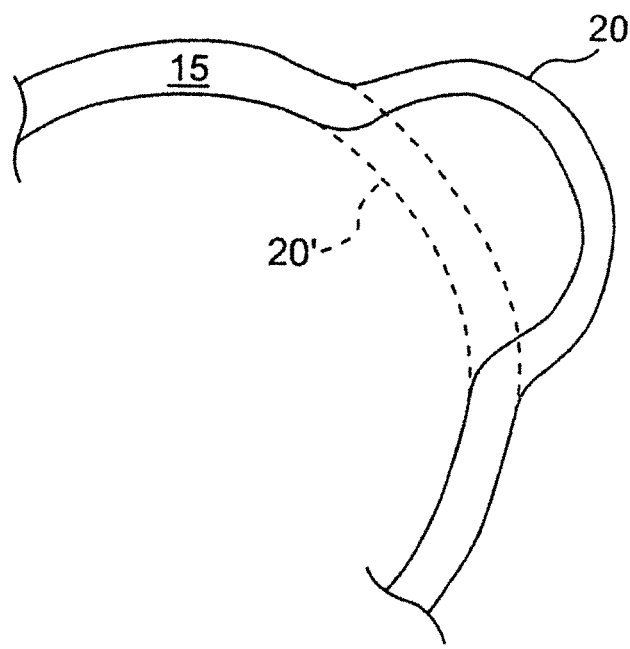
FIG. 14 depicts a heart including an infarcted region in response to the present invention.
Figure 15A:
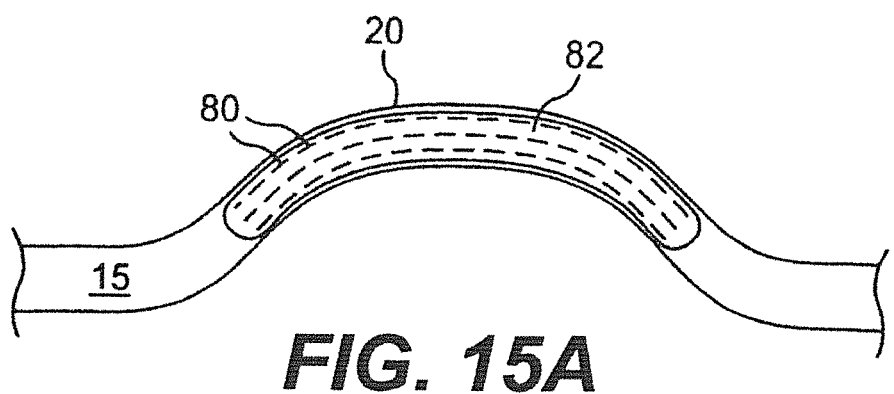
FIG. 15A depicts an alternative embodiment according to still another aspect of the invention and representative placement of embodiments of the invention in an infarcted region of a heart.
Figure 15B:
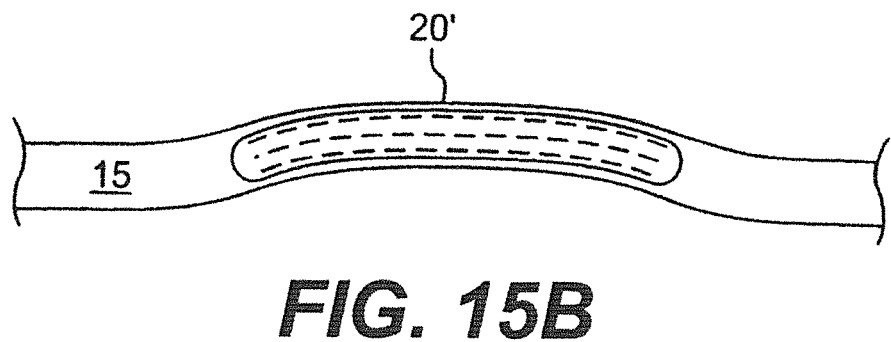
FIG. 15B depicts a heart including an infarcted region in response to the present invention.
Figure 16A:
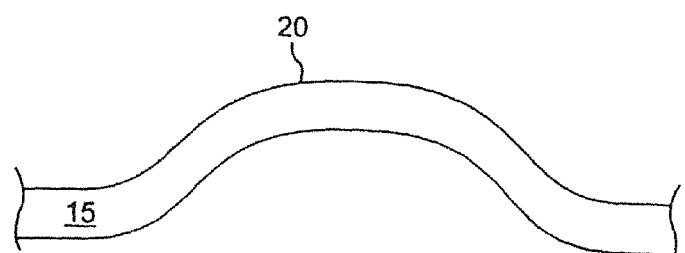
Figure 16B:
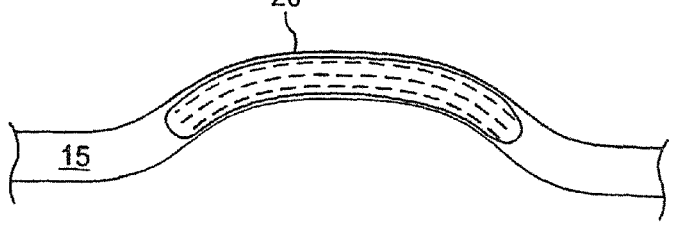
Figure 16C:
Figure 16D:
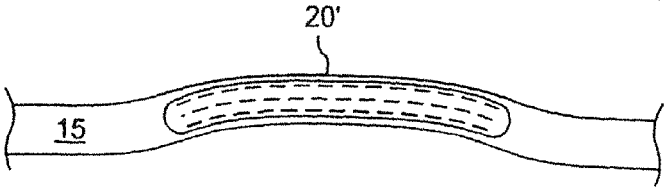

Some experimental research show improved ventricular function following cell transplantation into the infarct region (Scarsin. M. et a/. "Does Transplantation Of Cardiomyocytes Improve Function Of Infarcted Myocardium?": Circulation 1997; 96:11188-93; Leor J. et al., "Gene Transfer And Cell Transplant: An Experimental Approach To Repair A Broken Heart,". Cardiovascular Research 1997; 35:431-41). The present inventors believe there is evidence that such implantation may actually work by this mechanism. It has been observed that many different cell types when implanted into infarcted tissue result in improved ventricular function. While the actual function of these cells may be the reason for the improved ventricular function, the present inventors recognized that these cell-implants lead to increased stiffness and increased wall thickness in the infarcted region. As a result of this stiffening, bulge 20 is reduced to bulge 20' as depicted in FIGS. 14 and 15b. A gradual shrinking is depicted in FIGS. 16a through 16d, and from FIG. 16e to FIG. 16f. FIG. 16a shows the bulge 20 prior to application, FIG. 16b shows the same bulge 20 after application, FIG. 16c depicts the bulge as fibers shrink, and FIG. 16d depicts the decreased bulge 20'.

As with previous embodiments, these devices can be placed either through a percutaneous, mini-thoracotomy, or open-chest approach. The infarcted tissue is located as previously described, and the devices are deployed as previously described.

FIG. 17 presents a still further embodiment of the invention to stiffen myocardial tissue. Implants 90, made of material such as metal particles in a viscous biocompatible gel matrix, are injected into the infarcted tissue. The infarct tissue stiffens due to the properties of the material injected and also due to encapsulation of the material by the body. Additionally, these encapsulated areas tend biologically to link together, further stiffening the myocardium.

The material is placed either through a percutaneous, mini-thoracotomy, or open chest approach. The material is directly injected into the infarct tissue, or is injected into the coronary artery or vein. The infarct region is located as previously described. For the percutaneous approach, a catheter is placed in the left ventricle and positioned against the endocardial border. In one embodiment, a guidewire with side holes and a lumen is advanced into the infarcted tissue. Once within the infarcted tissue, the material is injected. These injections are repeated in multiple regions of the infarct. Percutaneous delivery for endocardial placement can also be practiced for the placement of rods, capsules, clamshells, buttons, or any other embodiment of the present invention.

For an open chest approach, a small needle can be inserted into the infarct tissue and the material is injected. A similar procedure is used for a mini-thoracotomy approach.

In another delivery approach, the material is injected into a coronary vein to reach the infarcted tissue. In this approach, a guide catheter is positioned in the coronary sinus via a vein, such as the right or left femoral vein. The guide catheter is advanced into the great cardiac vein, and a smaller catheter positioned in the coronary vein in the infarct region. A guidewire is used to assist this placement. In one approach, this catheter is similar to a balloon occlusion catheter; the catheter has a central lumen and an external balloon that is inflated thereby occluding the coronary vein. Once occluded, the material is injected retrograde into the coronary vein. The material has barbs, shapes, or coatings that facilitate embedding or entrapment in the small veins and capillaries. This leaves the material in the infarct tissue region.

In a further embodiment, the implants 90 can be made from a material comprised of two or more precursors, such as biocompatible polymer precursors, such as hydrogels, which when mixed increase in viscosity and/or stiffness, which when injected in the infarcted region, serve to stiffen it. The precursors can be mixed prior to injection, or mixed in situ. The injected or perfused precursors can contain additional particulates for stiffening, or be injected without. The injected material can also include luminescent, radiopaque or other contrast agents to enhance visualization.

The material itself can be non-absorbable. Such material is biocompatible, but is not absorbable to the extent that injection or perfusion of the material into the infarcted region leads to encapsulation. Many materials can be used, such as metal filings. In another embodiment, non-metallic materials are used, including various plastics. Materials that readily absorb different types of energy such as ultrasound and/or microwaves can also be used. As described later in this patent application, by this approach, the material not only stiffens the infarct tissue, but also facilitates the absorption of energy to heat this tissue and thereby shrink the tissue. Representative materials include metals (e.g., Stainless Steel, Titanium, Nitinol), nonmetals and polymers (e.g., Carbon, including Pyrolytic Carbon, Teflon, Polymers, Silicone, Polyurethane, Latex, Polypropylene, Epoxy, Acrylic, Polycarbonate, Polysulfone, PVC), fibrous materials (e.g., Polyester, ePTFE, Teflon Felt), and natural substances (e.g., Starch, Cat Gut]. Of course, this list is merely exemplary and any biocompatible material can be used.

In another embodiment, liquid plastic materials are used. The liquid plastic material is injected into the coronary vein draining the infarct tissue. The material solidifies, thereby stiffening the infarct tissue.

Figure 18A:
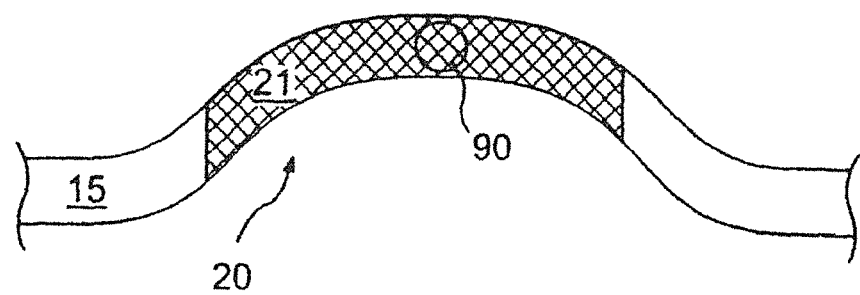
FIGS. 18A and 18B depict a still further aspect of the present invention where a material that bonds to dead cells or specific proteins is injected into the infarct region.
Figure 18B:
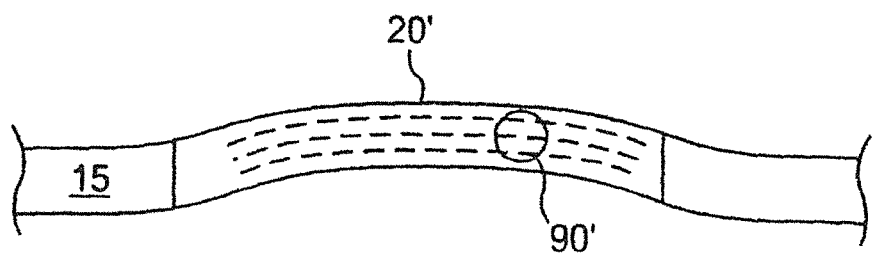

As shown in FIG. 18a, a material that bonds only to dead cells is injected into the infarct region. Within the infarct region 21, dying myocytes with internal cellular elements are exposed to interstitial fluids as necrosis progresses. Implants or material 90' known in the art that bonds to and fixes only to dead cells or other elements associated with cell necrosis can be introduced. In this approach, a guide catheter is positioned by the left or right coronary artery. A smaller catheter is advanced into the coronary artery responsible for the myocardial infarction. Once by the site of coronary occlusion, the material is injected directly into the coronary artery. The material flows down the coronary artery to reach the infarct tissue. The material recognizes the dead cells by proteins or other elements that are not normally present or not normally exposed to the surrounding tissue; i.e., internal cellular elements. The material bonds to these proteins or elements and develops links between the dead cells or other elements, thereby fixing this tissue. This stiffens the infarct tissue, and also prevents such processes as myocardial infarct expansion as shown in FIG. 18b.

In clinical practice, this approach to fix the dead cells is applied shortly after the infarct-related artery is re-opened either by angioplasty, by thrombolytic therapy, or by natural means. Vessel patency is confirmed by standard coronary angiography. A simple approach is used to momentarily decrease the left ventricular size. This is achieved through afterload reducing agents or by partially inflating a balloon catheter in the inferior vena cava. These decrease left ventricular size, and thus the size to the infarct. During these maneuvers, the material is injected into the artery, fixes the dead tissue, and prevents ventricular remodeling by preventing the initial infarct expansion. Fixing the tissue especially at reduced left ventricular volume also results in immediate improvements in left ventricular systolic function; the infarct tissue is stiffer and its relative and absolute size decreased.

The fixed tissue may eventually be reabsorbed, but other approaches described in this patent application are used to prevent ventricular remodeling.

In another embodiment, the material is injected intravenously, travels through the circulation to the infarct tissue, and fixes this tissue.

FIGS. 19a through 19f present another method to stiffen the infarct tissue. Via a percutaneous approach, a catheter is placed in the left ventricular cavity. The catheter is positioned against the left ventricular wall. The infarcted tissue is detected based on several possible criteria: wall motion, local electrical potential, or local electrical impedance. Other techniques can also be used. Capsule like devices 92, which may have retaining prongs 96 are inserted into the myocardial tissue 15. The prongs or other shapes on these devices prevent migration of these devices out of the infarct tissue. Once inserted, these devices increase the stiffness by their mechanical properties and by adhesions to the surrounding tissue. Multiple devices can inserted into the infarct and peri-infarct tissue. In other approaches, the devices are placed either through a mini-thoracotomy, or open chest approach. The devices can be inserted using devices similar to staplers. and placed using a needle tip. The capsules can be biosorbable, contain implantable biocompatible materials such as silicone, polyurethane, PTFE. etc. or contain stiffening particles as earlier discussed or drugs, either alone or in a matrix. Other devices described herein can be deployed in a similar manner. Additionally, material can be injected into the myocardium in conjunction with a mechanical device inserted previously, or subsequently.

Figure 19C:
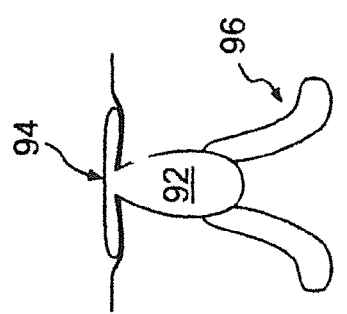
FIGS. 19A through 19F depict still further alternative embodiments according to still another aspect of the invention.
Figure 19B:
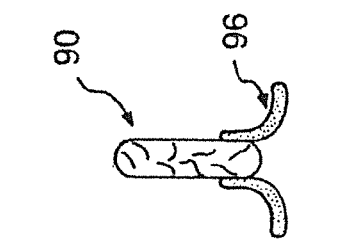
Figure 19A:
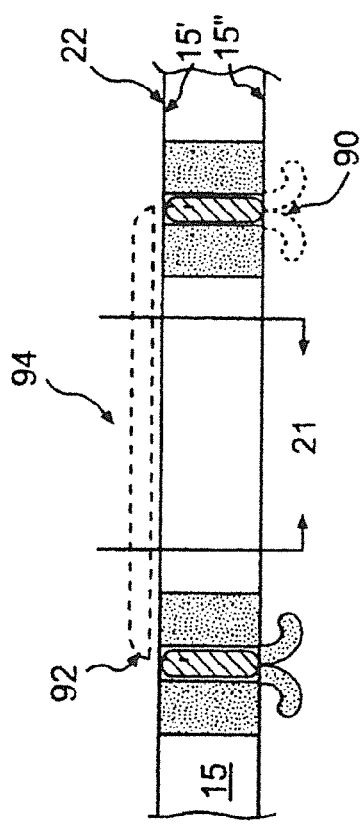
Figure 19F:
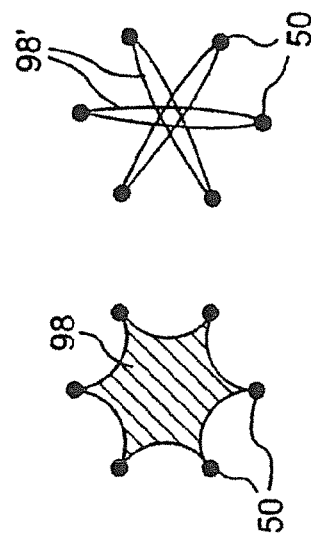
Figure 19E:
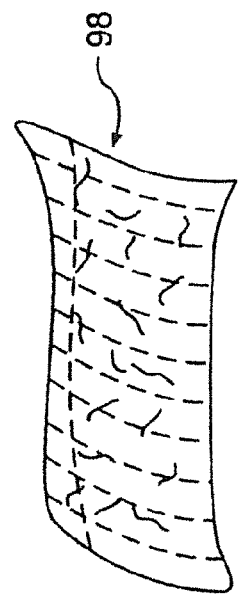
Figure 19D:
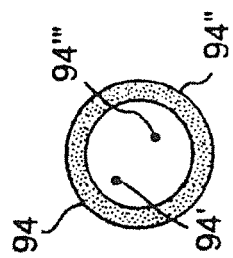

Prongs 96 can be spring loaded for quick insertion using delivery devices similar to a surgical stapler. The prongs 96 can additionally be made of biosorbable material, or shape memory material such as nitinol. The capsules 92 can further have a cap 94 to aid in securement. As shown in FIG. 19d the cap 94 has a silicone pad 94' surrounded by a Dacron mesh 94" by way of example. Suture holes 94''' can also be on the cap. FIG. 1ge shows a sheet of cap mesh 98, which can be employed to connect multiple devices described hereinabove. As shown in FIG. 19f, mesh 98 is shown connecting a plurality of devices 50 to form a cluster. The mesh material can inherently shrink due to, e.g., noninvasive application of microwave energy, exposure to in vivo conditions such as heat or moisture. Dissolvable or biosorbable bridging material can also be used, either as a matrix or a substrate material, such that after it dissolves, the mesh contracts. FIG. 19f also shows strands 98' of similar material connecting multiple devices 50. Of course a unitary device can be made having multiple anchors connected by the materials discussed here.

Figure 20:
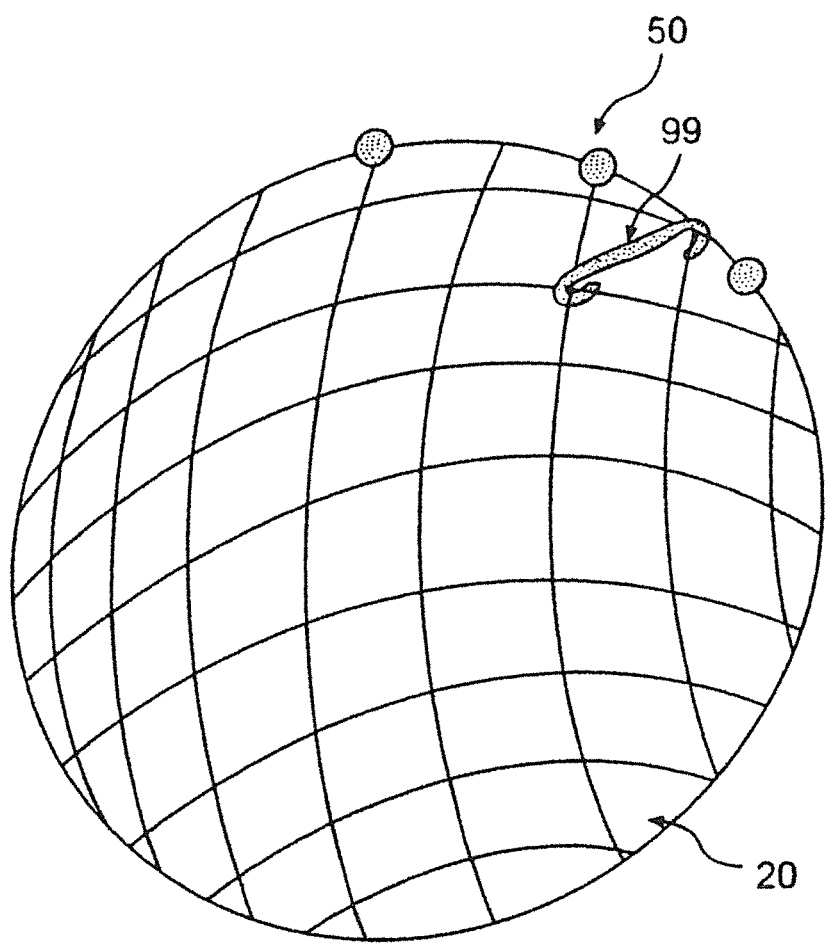
FIG. 20 depicts further alternative embodiments according to still 'another aspect of the invention.

FIG. 20 shows another approach to shrink the infarct size. In this approach, a pre-stretched wire mesh 98 is placed over the infarct tissue from the epicardial surface 15'. This wire mesh 98 can be anchored to the border of the infarcted tissue by devices 50, and can also include coil type electrodes. These coils and/or mesh can be used for various therapeutic treatments, such as pacing to re-synchronize ventricular contraction or the mesh and/or electrodes can be used for defibrillation. Other anchoring means can also be used. The wire mesh is preferably biased to contract inwardly either axially or radially, and is maintained in a pre-stretched condition by bio-absorbable material spacers 99 placed between the wires as shown in FIG. 20. The connectors, or spacers, placed on mesh material that is pre-expanded. As the spacer 99 dissolves, mesh material 98 shrinks pulling the myocardial tissue towards the central portion of the mesh 98. This device is placed either through a minithoracotomy or an open chest approach.

While the above paragraphs describe the use of bio-absorbable material between the coils of a spring or the weave of a wire mesh, these devices can also be employed without the bio-absorbable material. The fiber, spring, or mesh is placed in a stretched condition. This can immediately shrink the tissue, and with time lead to even further shrinking of the infarct tissue area.

By stiffening the infarct tissue, the abnormal geometry and wall stress by the peri-infarct region are partially corrected.

Figure 21A:
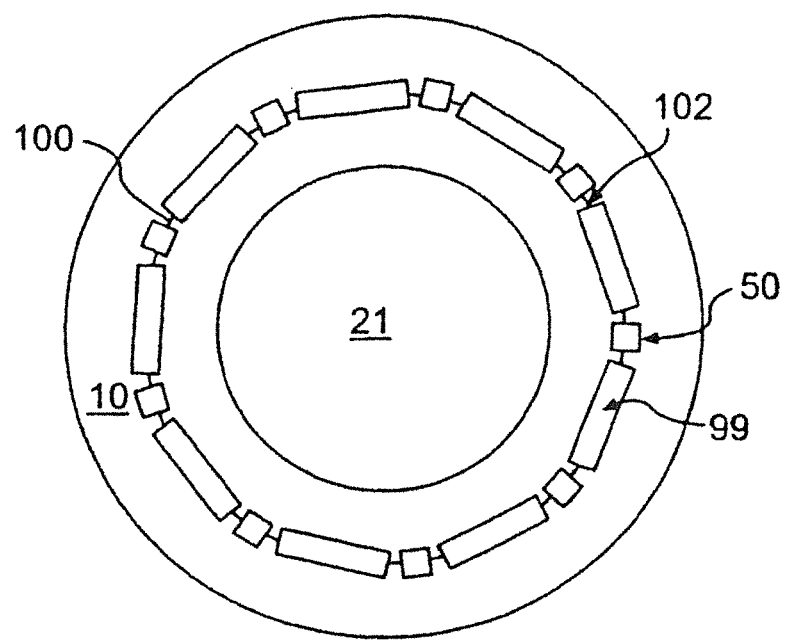
FIG. 21A depicts an alternative embodiment according to still another aspect of the invention and representative placement of embodiments of the invention in an infarcted region of a heart.
Figure 21B:
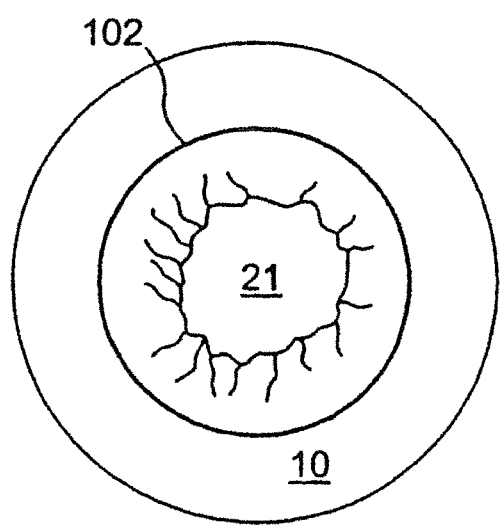
FIG. 21B depicts a heart including an infarcted region in response to an embodiment of the present invention.

In a still further embodiment of the present invention, FIG. 21a shows a system to mechanically isolate the infarcted tissue. Devices 50 are placed on the epicardial side of the heart 10 by the infarcted tissue 21. The devices are connected by a wire 100, forming a loop 102, which is tightened to pull the devices 50 together. Several of these devices 50 can be placed, such that the tightening of the wire 100 results in a cinching effect of the loop 102 about the infarcted tissue 21, mechanically excluding it. The wire 100 can exhibit elastic or shape-memory characteristics, such that the spacers 99, which can be dissolvable over time, result in a gradual tightening of the loop 102 and the cinching effect. Alternatively, the wire 100 can be tightened incrementally over time mechanically, additionally, for example, using a transthoracic or percutaneous or transcutaneous tightening tool. FIG. 21b shows the cinching effect about an infarcted region 21.

These devices are placed either through a percutaneous, mini-thoracotomy, or open-chest approach. The infarct is identified and the device deployed.

In another embodiment, the systems described above are used with other technologies to decrease infarct size. For example, heat shrinks myocardial infarct size (Ratcliffe, M. B. et al., "Radio Frequency Heating Of Chronic Ovine Infarct Leads To Sustained Infarct Area And Ventricular: Volume Reduction," J. Thoracic And Cardiovascular Surgery 2000; 119:1194-204; see a/so U.S. Pat. No. 6,106,520). Once the heat has decreased the infarct size, the devices described above are used to stabilize the infarct and to prevent re-expansion of the infarcted tissue. Note that in some embodiments described above, the material used to stiffen the infarcted tissue can also increase the heat absorption. For example, when the heat source is a microwave generator and metal material or devices are used, this material rapidly absorbs microwave energy. The microwave applicator is applied to the external surface of the heart or through the chest and radiates the energy to the heart. Also note that infarcted tissue has a much lower than normal blood flow rate. The infarcted tissue by having these metal particles imbedded in it and by the low blood flow levels develop a higher temperature increase compared to normal myocardial tissue. This heat causes the scarred, infarcted tissue to shrink. Given the ease of externally applying the microwave energy, multiple applications are used. These applications may be weekly, daily, etc. [at various time points]. In other embodiments, other energy sources are used.

Another simple approach is to momentarily decrease the left ventricular size. This is conventionally achieved through afterload reducing agents or by partially inflating a balloon catheter in the inferior vena cava. These procedures decrease left ventricular size, and thus the size to the infarct. The spring devices, etc. can advantageously be placed during these maneuvers.

Previous efforts have used heat to denature the collagen fibers in the infarcted tissue to shrink the size of the myocardial infarction. However, the denatured fibers are much weaker, and a patch had to be sutured over the infarct tissue to prevent re-expansion (Ratcliffe 2000). The present invention dispenses with these drawbacks by using the devices described herein in combination with heat. First, the springs or fibers by themselves shrink the tissue. Applying heat also shrinks the infarct tissue. The springs are appropriately biased to resist re-expansion.

FIG. 18 shows a system to shrink the size of the infarct tissue. A fiber or material is placed into the infarct tissue. This fiber has several expansions along its length that form firm adhesions to the surrounding tissue. The fiber between these nodal points gradually shrinks over time; i.e., days to weeks. As the fiber shrinks, the fiber pulls the nodal points together, thereby shrinking the infarct tissue and decreasing the size of the infarct.

The fiber is placed either through a percutaneous, mini-thoracotomy, or open chest approach. Once the infarct tissue is recognized by the approaches previously described, several fibers are placed in the infarct region to decrease the size of the infarct.

In other embodiments, the systems described above are used with other technologies to decrease infarct size. For example, heat can shrink myocardial infarct size. Once the heat has decreased the infarct size, the device described above is used to stabilize the infarct and/or to further shrink the size of the infarct.

Figure 22A:
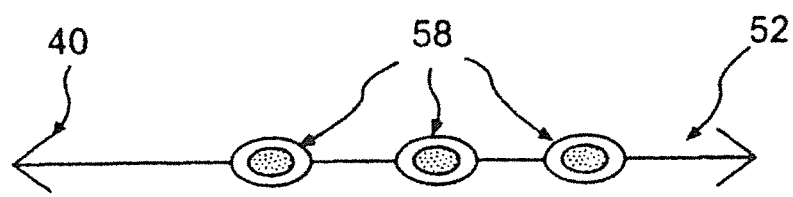
FIGS. 22A through 22C show an exemplary embodiment of a further aspect of the invention that becomes shorter over several weeks.
Figure 22B:
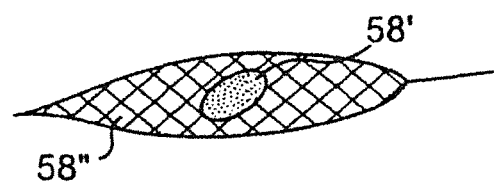
Figure 22C:
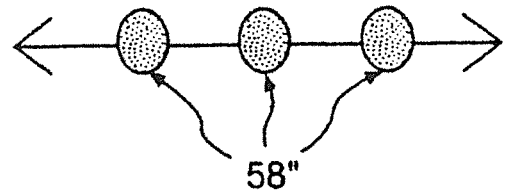

It may be desirable to have devices that become shorter over several weeks. FIGS. 22a through 22c show an example of such a device 50. The device has multiple enclosures 58 within which expandable material 58' is contained. The body 52 is made of wire or polymers that do not stretch. Before expansion, the enclosures can be oval in shape as shown in FIG. 22b. The material for example can absorb water, and thereby expand over several weeks, or any selected period of time. As this material expands, the enclosures go from an initial shape, in this case a narrow oval-like shape, to a more compact shape, in this case a circular or spherical shape. The length of each enclosure shortens, thereby shortening the overall length of the device, as shown in FIG. 22c.

Figure 23:
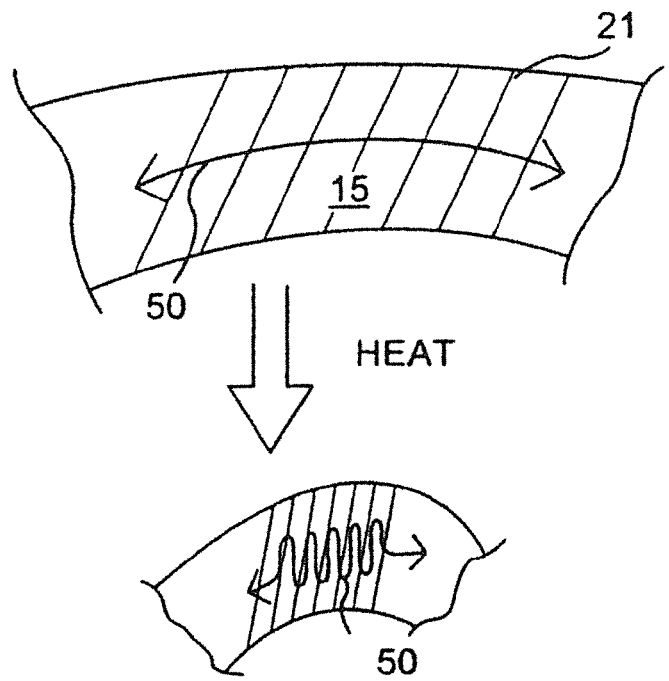
FIG. 23 shows a further exemplary embodiment over a gradually shortening device.

FIG. 23 shows a restraining device within the myocardial tissue. The body of the device is made of nitinol. The device 50 is forced into a straight pattern. The device is inserted into the myocardium 15 in this straight shape. After several weeks, the device is heated to its critical temperature (420 C, for example). This temperature increase can be achieved through several means, such as using microwave energy: The metal quickly absorbs the microwave energy. Further, the low blood flow in the infarct region allows for a rapid temperature increase within this infarct region. Other energy sources can also be used. Once the device is heated to its critical temperature, the device reverts back to its predetermined shape. This change in shape shortens the overall length of the device, decreases the surface area of the infarct region 21, and increases wall thickness.

Figure 24:
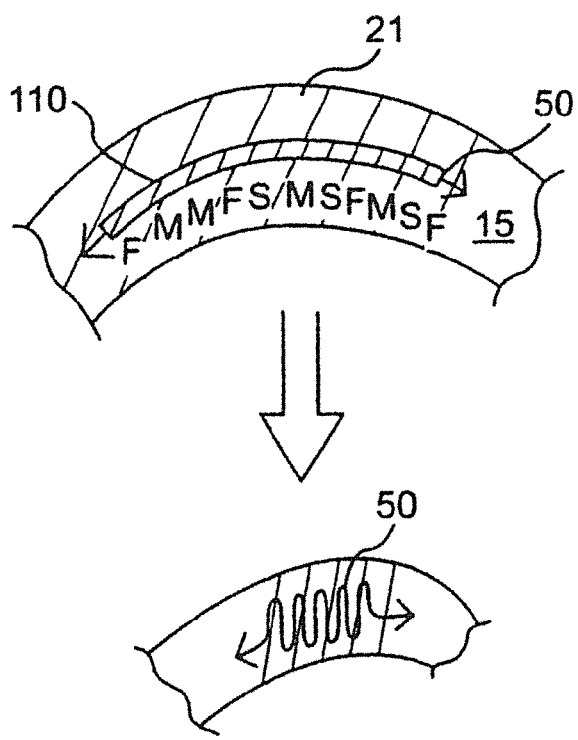
FIG. 24 shows a still further exemplary embodiment over a gradually shortening device.

FIG. 24 shows another approach. The body of the device is made of nitinol. The device is forced into a straight pattern, and maintained in this shape by enclosing within a tube 110. The device 50 is inserted into the myocardium in this straight shape. The tube 110 is made from bio-absorbable material. The tube can have regions that have different absorption rates from slow to fast (S, M, F). After several weeks, the tube is reabsorbed, and the nitinol reverts back to its normal shape. This change in shape shortens the overall length of the device 50.

One of the advantages of the present invention in regionally effecting myocardial wall properties is the ability to not only restrain the motion of the infarcted area but to constrain it, causing the damaged area to shrink over time. It is also possible for devices according to the present invention to apply tension to the wall immediately after application of the device, or for the tension to be delayed for some time. In either case it may be necessary for the device to be in one state during deployment and a second state to apply tension. There are several avenues that could be employed for delaying the time when tension becomes employed.

First, devices can be produced from materials that remain in one state upon deployment and have the ability to change to a second state when activated. Nickel-titanium alloys are well known for displaying this two-state property. The ability to change states is the result of the material undergoing a phase transformation between a weaker form at low temperature (Austenite) and stronger form at higher temperature (Martensite). By varying the mix of the alloy, the temperature range under which the materials undergo the transformation can be tailored to be just above body temperature. The device, a mesh for example, is formed (deformed) into the desired shape at below the transformation temperature. The device is applied. At some time post application, the device can be heated slightly causing the device to recover to its preformed shape (slightly tighter mesh) and apply tension to the myocardial tissue.

Polymers can also be used, and have the added advantage of being more easily formed as a mesh or fiber that can be sewn or attached over damaged tissue and then activated. Polymers including polyurethane-types and Polynorbomene are materials that exhibit a sharp glass to rubber phase with glass transition temperature (Tg) just above room temperature. They are deformed above Tg then cooled (while being restrained). When heated above Tg, they quickly try to revert to their previous form. As above, a mesh or fibers can be attached over the infarcted area. Once deployed, it can be activated causing the mesh to apply tension and shrink the tissue.

Other devices according to the invention can be inherently under tension, such as springs discussed hereinabove, but restrained from applying the tension by some mechanism. For a device that is to be put under tension immediately upon application, restraining the device can be achieved by designing the constraining mechanism into the delivery system. A spring for example can be held in an elongated position by some portion of the delivery system. Once inserted into the myocardium, the restraining portion is removed allowing the spring to be under tension thus constraining the tissue.

It is also possible to deploy the device in an elongated fashion but not allow it to apply tension until some delayed time, this can be achieved with bio-absorbable polymers as discussed hereinabove. The polymer can be placed in the interstices of spring coils or a stretched mesh keeping it in an elongated form. As the polymer is absorbed, the spring will slowly be placed under tension putting the tissue under tension. There are several families of bio-absorbable materials that can be explored for this application. The majority of these materials are derived from glycolic acid, lactic acid, trimethylene carbonate, polydioanone and caprolactone. Different mechanical and biodegradation properties can be achieved by varying monomer content, processing conditions, additives, etc. Another promising family of materials is polyhydroxyalkanoates or PHA polymers. These are naturally occurring biopolymers being developed my Tepha, Inc. in Cambridge, Mass. They have thermo elastic properties, unlike other biopolymers, and are melt processable.

Other variants are envisioned, for example, a fiber may be implanted within the myocardium that shrinks over time. A series of such may be placed acutely to stiffen and shrink infarct size over time. The fiber further may have features such as knots, anchors, and other stabilization and fixation mechanisms.

Figure 25A:
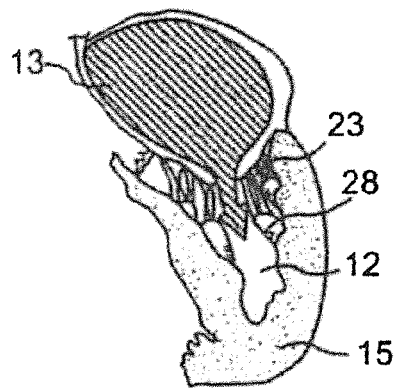
FIGS. 25A through 25D depict a still further aspect of the present invention applied to effect additionally the papillary muscles for treatment of mitral valve regurgitation.
Figure 25B:
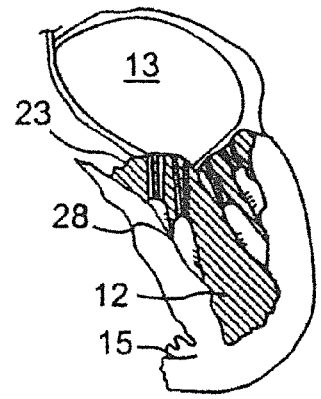
Figure 25C:
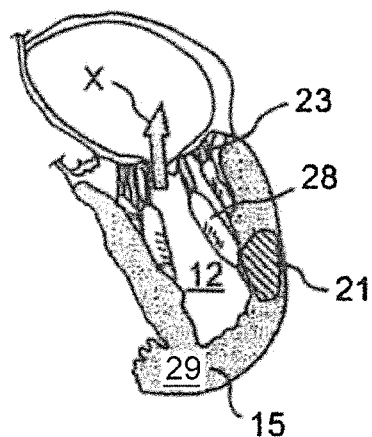

The systems described above have other advantages or actions, and these actions can be the main therapeutic reason for their application. For instance, as shown in FIGS. 25a through 25d, after myocardial infarct 21 the ventricle remodels and becomes larger. FIG. 25a depicts normal mitral valve action during left ventricular filling from the left atrium 13. The mitral valve is controlled by papillary muscles 28 expanding and contracting, and are connected to the valve by the chordae tendinae 23. FIG. 25b depicts the heart after filling of the left ventricle 12, where the valve is closed. The enlargement of infarct region 21 as shown in FIG. 25c however, together with other infarcts in the region of the papillary muscles 28 can cause the base of the papillary muscle to descend and move away from the mitral valve plane.

Figure 25D:
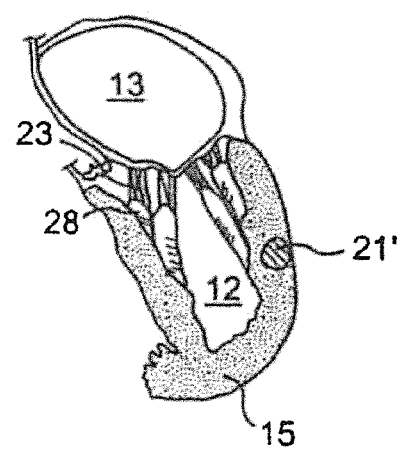

In systole, the increased pressure in the heart further pushes the base of the papillary muscles away from the valve plane. The papillary muscles 28, by way of their attachment to the cordae tendinae and thus the mitral valve leaflets, pull on the leaflets preventing the leaflets from closing. This can lead to an event known as mitral valvular regurgitation, where blood is ejected from the ventricle back into the atrium as shown by arrow X in FIG. 25c. Once mitral valvular regurgitation occurs, the process tends to lead to further dilatation of the left ventricle, which in turns leads to further mitral valvular regurgitation. Cascading events of this type, without intervention, will potentially contribute to dilated cardiomyopathy and decreased cardiac output. By application of the present invention, infarct region 21 can be stiffened and/or diminished in overall size, as shown in FIG. 25d, promoting a decrease in distension of the papillary base, and therefore decreased tugging on the chordae tendinae 23 and improved sealing of the mitral valve. As mentioned hereinabove, practicing the invention at the apical base 29 can advantageously provide better support to the papillary muscles in the treatment of mitral valve regurgitation.

The afore-described methods and apparatus, by stiffening the infarcted tissue, limits the movement of the base of the papillary muscles. thereby preventing mitral valve regurgitation as depicted in FIG. 25c. By shrinking the infarct region to smaller region 21'. papillary muscle expansion is reversed to the direction shown by arrow D. and chordae tension decreased. Also. during systole, the pressure within the left ventricle increases. This increased pressure places higher stresses on the infarct tissue. Now however. the increased stiffness of the infarct tissue prevents or at least decreases the bulging outward from the center of the left ventricle and downward from the mitral valve plane of the infarct tissue. By decreasing this motion, the magnitude of mitral valvular regurgitation is decreased. which in turn leads to a reverse remodeling of the left ventricle; i.e., the left ventricle becomes smaller, leading to less mitral regurgitation. Further, practicing the invention herein at the papillary base near the apical region 29 causes a stiffening. therefore therapeutically addressing the lengthening of the papillaries, and even causing a shortening in the direction of arrow E, causing a decrease in mitral regurgitation.

One further approach according to the present invention to stiffen the infarct tissue is to inject into the myocardium material, which will stiffen the myocardium and will sensitize the myocardium for subsequent treatment. Key elements are to inject material that will not occlude important perfusion vessels and will be encapsulated within the myocardial tissue. One such approach is to inject metal microspheres into the infarcted myocardium. By selecting microspheres large enough to lodge in the myocardium (>10 μM). but not large enough <25 μM) to occlude larger vessels (and thus cause ischemia by themselves), the infarcted myocardium is seeded with microspheres. These microspheres by their mechanical integrity stiffen the myocardium. The small vessel in which the microspheres are initially trapped quickly breakdown (since the vessel no longer provide perfusion) leaving the microspheres in the infarcted tissue. The microspheres become encapsulated by scar tissue, further stiffening the tissue. These microspheres sensitize the infarcted myocardium to subsequent exposure to heat sources, such as microwaves. This heating of infarcted tissue leads to shrinkage of this tissue.

U.S. Pat. No. 4,709,703 issued to Lazarow and Sove on Dec. 1, 1987 describes the use of radiopaque (metal) microspheres for evaluation of organ tissue perfusion. Radiopaque microspheres are administered to organ tissue, which is then scanned using a computerized tomography (CT) scanner which provides a visual CT image and/or statistical report providing an indication and/or measurement of organ tissue perfusion.

Delivery of the metal microspheres (preferred 15 to 18 μM) is achieved with current clinical catheters. Many patients will have an angioplasty procedure performed after a myocardial infarction. Via an artery, commonly the femoral artery, a catheter is introduced into the arterial system and then under X-ray is positioned by the left or right coronary artery. Radiodense contrast material is injected to identify the location of the coronary obstruction that caused the myocardial infarction. A guidewire is advanced into the culprit artery and passed the coronary obstruction. An angioplasty catheter is advanced over the guidewire passed the coronary obstruction. The guidewire is removed. At this point in the procedure, the metal microspheres are directly injected through the distal lumen of the angioplasty catheter into the culprit artery. Thus. the microspheres go almost exclusively to infarcted tissue. Alternatively, the guidewire can be used to introduce the microspheres rather than the central lumen of a catheter, for example a PTCA catheter, so that the catheter does not need to cross the coronary obstruction or lesion. The remaining clinical procedure is routine care, generally either angioplasty, angioplasty with stent deployment, or stent deployment alone.

While the above has described metal microspheres, other types of microparticles can be used. For example. micro-rods maybe injected. These micro-rods have the same diameter of the microspheres (about 15 to 18 µM). However, their longer length enables a greater volume of material to be injected. Additionally, the micro-particles can be coated with material to induce other effects, such as the further stiffening of the scar tissue. contraction of the scar tissue, or other beneficial effects. Such agents might include, but are not limited to, Transforming Growth Factor (TGF) Beta 1. 2. or 3. colligin, or matrix metalloprotease inhibitors. The micro-particles can be made of material that gradually absorbs water, thereby increasing their volume and effectiveness.

Note that over the first two-month post-myocardial infarction, the scar tissue tends to contract and shrink. This natural process increases the density of the microspheres in the infarct region. This increase in density increases the stiffness caused by the microspheres. Also, note that some microspheres are lost to the general circulation. This microsphere lost is reduced by using microspheres >10 µM. The lost microspheres become lodged in other organs and in the lymph nodes. By using microspheres smaller than 25 µM, ischemic damage in other organs is prevented.

Another means to inject particles into the myocardial infarct tissue is through the coronary venous system. The advantage to this approach is that larger particles can be injected into the venous system without effecting coronary blood flow. Throughout the body, arteries and veins are in close proximity. The heart, and especially the left ventricle are no exception. Coronary veins run in close proximity to the major coronary arteries (Fitzgerald P J, Yock C. Yock P G. "Orientation Of Intracoronary Ultrasonography: Looking Beyond The Artery," J Am Soc Echocardiogr. 1998; 11:13-19).

Similar to LV angiograms and angioplasty, there are three main elements to this approach: a guide catheter to position in the coronary venous sinus, a steerable guidewire, and a flexible catheter that can be advanced over the guidewire and into the target vein. Current, clinically available catheters and guidewires can be used. Indeed, this coronary venous approach has been used for drug therapy (Corday E, Meerbaum S, Drury J K. "The Coronary Sinus: An Alternate Channel For Administration Of Arterial Blood And Pharmacologic Agents For Protection And Treatment Of Acute Cardiac Ischemia," J Am Coli Cardiol 1986; 7:711-714).

The coronary sinus and its tributaries have been safely cannulated during electrophysiological mapping of reentrant pathways and ventricular tachycardia (De Paola A A. Melo W D, Tavora M Z, Martinez E E, "Angiographic And Electrophysiological Substrates For Ventricular Tachycardia Mapping Through The Coronary Veins," Heart 1998; 79:59-63.)

In a study by Herity (Herity N A, Lo S T, Oei F, Lee D P, Ward M R, Filardo S O, Hassan A, Suzuki T, Rezaee M, Carter A J, Yock P G, Yeung A C, Fitzgerald P J, "Selective Regional Myocardial Infiltration By The Percutaneous Coronary Venous Route: A Novel Technique For Local Drug Delivery," Catheterization and Cardiovascular Interventions 2000; 51:358-363), an Amplatz, Amplatz right modified, or Hockey stick coronary guiding catheter (Cordis, Miami, Fla.) was advanced to the right atrium, slowly withdrawn, and rotated posteromedially to engage the coronary sinus ostium. An exchange-length extra support guidewire (0.035", Terumo Corporation, Tokyo, Japan) was advanced via the great cardiac vein (GCV) to the anterior interventricular vein (AIV), which parallels the left anterior descending artery (LAD) in the anterior interventricular sulcus. Alternatively, the guidewire was directed into the middle cardiac vein (MCV), which runs in the posterior interventricular sulcus to access the posterolateral wall of the left ventricle. The guiding catheter was replaced over-the-wire by a balloon-tipped Swan-Ganz catheter, which was then advanced to the AIV or MCV and the guidewire was withdrawn.

Additional systems have recently been developed or are under development for biventricular or left ventricular pacing. One such pacing system and leads is the EASYTRACK system described below.

The EASYTRACK system (models 4510.4511, and 4512, Guidant, St. Paul. Minn.) is a transvenous, coronary venous, steroid-eluting, unipolar pace/sense lead for left ventricular stimulation. [Purerfellner H, Nesser H J. Winter S, Schwierz T, Homell H, Maertens S. "Transvenous Left Ventricular Lead Implantation With The EASYTRACK Lead System: The European Experience," Am J Cardiol 2000; 86 {suppl}: 157K-164K.] The lead is delivered through a guiding catheter with a specific design to facilitate access to the ostium of the coronary sinus. This catheter provides torquability using an internal braided-wire design. The distal end of the catheter features a soft tip to prevent damaging of the right atrium or the coronary sinus. The EASYTRACK lead has a 6 Fr outer diameter and an open-lumen inner conductor coil that tracks over a standard 0.014-inch percutaneous transluminal coronary angioplasty guidewire. The distal end of the electrode consists of a flexible silicone rubber tip designed to be atraumatic to vessels during lead advancement.

Thus, many clinical catheters and delivery systems are available to position a small (3 Fr) perfusion catheter into a coronary vein. Once positioned in the coronary vein close to the culprit lesion in the adjacent coronary artery, the metal particles are injected into the vein. As mentioned above with this approach, larger particles can be injected. Additionally, these particles can be rod shaped, thereby increasing the total volume of the particles injected, and/or the particles can be made of materials that absorb water. In another version, the infusion catheter can have a balloon occlude like a Swan-Ganz catheter. The balloon is inflated to occlude the coronary vein and then the particles are injected into the vein distal to the site of occlusion.

Most of the particles injected are lodged or trapped in the small venous vessels (Sloorzano J. Taitelbaum G. Chiu R C. "Retrograde Coronary Sinus Perfusion For Myocardial Protection During Cardiopulmonary Bypass, Ann Thorac Surg 1978; 25:201-8.). A filter can be placed in the coronary sinus to collect any particles that dislodge during the procedure.

Similar to the intracoronary approach. the metal particles stiffen the infarct tissue by their mechanical integrity and by being encapsulated with scar tissue. The bigger size of these particles adds to the stiffening of the infarct tissue.

Once the ischemic tissue is identified, devices or material can be placed directly into the left ventricular myocardium. The devices described herein can be placed during openheart surgery, through minimally invasive approaches or by a percutaneous approach.

For the percutaneous approach three main elements facilitate this approach: a steerable catheter positioned in the left ventricular cavity. a steerable guidewire and a flexible catheter that can be advanced over the guidewire and into the myocardium. Current. Clinically available catheters and guidewires can be used.

Over twenty years ago using a percutaneous approach, radiopaque tantalum coils were placed into the left ventricular myocardium. In these experimental studies (Santamore W P. Carey R A. Goodrick D. Bove A A. "Measurement Of Left And Right Ventricular Volume From Implanted Radiopaque Markers.". Am J Physiol 1981 t 240:H896-H900) the radiopaque coils were placed in multiple locations throughout the left ventricle. Under X-ray, the position of each radiopaque marker was determined. In turn. this positional information was used to assess global and regional left ventricular function. Via the carotid or femoral artery, a clinically available steerable catheter (Biliary stone removal catheter) was positioned under X-ray into the left ventricular cavity. Using the steerable attributes of the catheter, the distal tip of the catheter was pressed against the endocardial wall at the desired left ventricular location (anterior, posterior, free wall, septum, base, apex, etc.). A modified commercially available guidewire with tantalum coil attached was inserted into the central lumen of the steerable catheter. The guidewire end was modified to have a stiff center wire and a shoulder. The stiff point helped to engage the left ventricular myocardial and to hold the tantalum coil. The shoulder enabled the coil to be screwed into the left ventricle by turning the guidewire. Once the catheter was in the desired position, the guidewire was pushed out and turned to screw the tantalum coil into the myocardial. The guidewire was removed leaving the tantalum coil in the myocardium.

Since this time, many steerable catheters have been developed, for example those described in U.S. Pat. No. 5,190,050 to Nitzsche, U.S. Pat. No. 5,358,479 to Wilson, U.S. Pat. No. 5,855,577 to Murphy-Chutorian, U.S. Pat. No. 5,876,373 to Giba, and U.S. Pat. No. 6,179,809 to Khairkhahan, the disclosures of all of which are incorporated herein by reference.

In addition to a steerable catheter, the guidewire may also have a preferred shape. U.S. Pat. No. 5,769,796 issued to Palenno describes a super-elastic composite guidewire. This is a composite guidewire for use in a catheter and is used for accessing a targeted site in a patient's body. The guidewire core or guidewire section may be of a stainless steel or a high elasticity metal alloy, preferably a Ni—Ti alloy, also preferably having specified physical parameters. The composite guidewire assembly is especially useful for accessing peripheral or soft, tissue targets. Variations include multi-section guidewire assemblies having (at least) super-elastic distal portions and super-elastic braided reinforcements along the mid or distal sections.

Figure 26A:
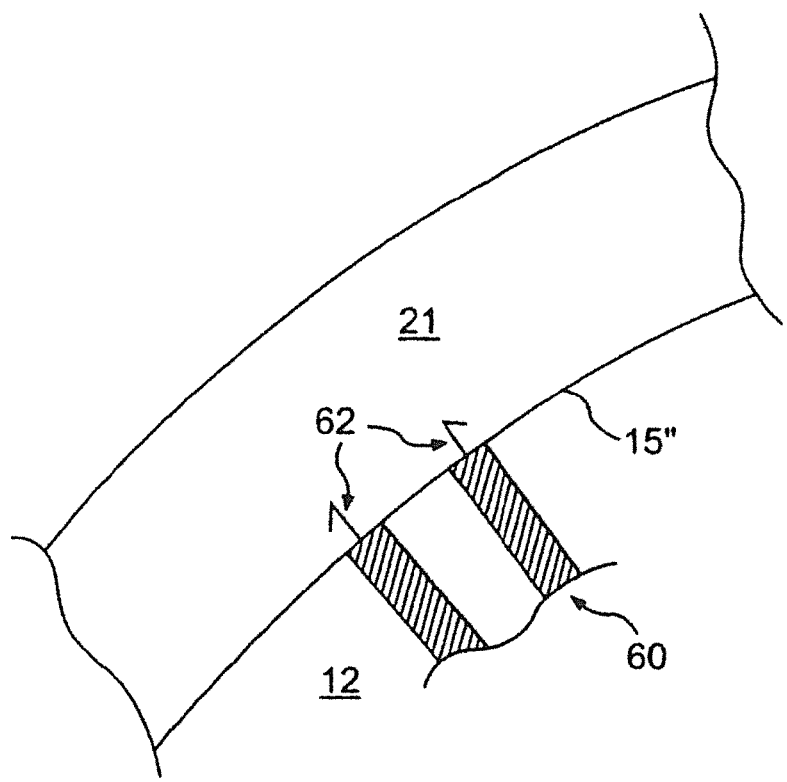
FIGS. 26A through 26C show a further exemplary embodiment of the present invention including a method for insertion.
Figure 26B:
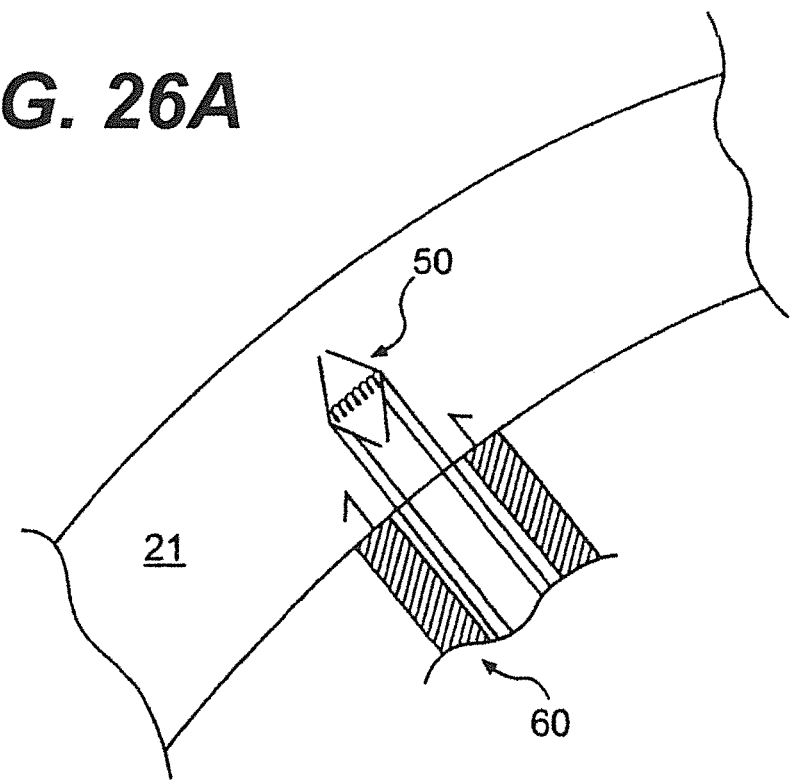
Figure 26C:
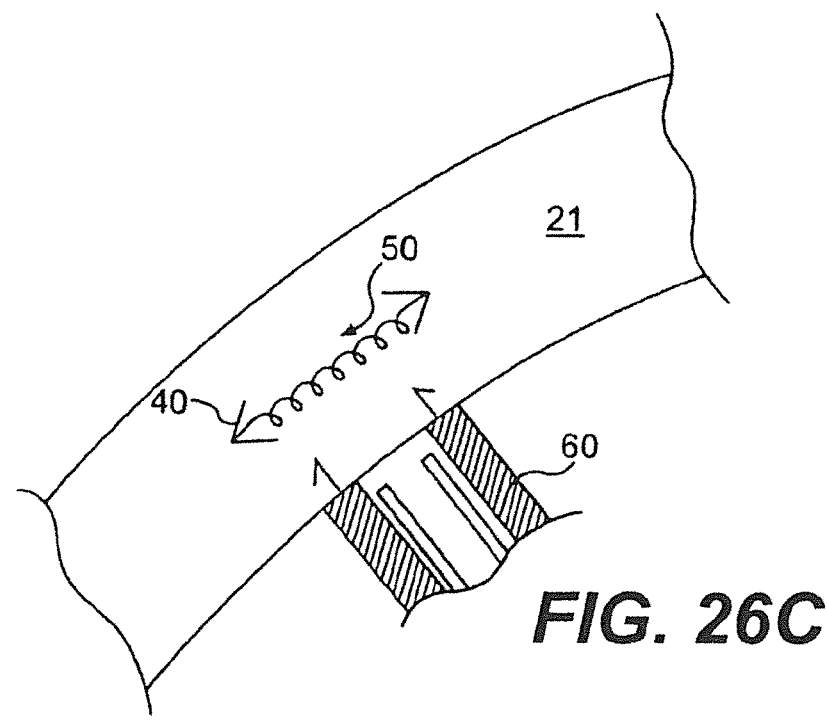

Turning now to FIGS. 26a through 26c show one example of endocardial placement. The area of myocardial infarction 21 is identified by one of the previously mentioned methods. Via an artery such as the femoral artery. the steerable catheter 60 such as described in U.S. Pat. No. 5,876,373 is positioned in the left ventricle 12. The tip of the catheter is positioned against the endocardial surface 15". The anchors 62 are deployed to hold the catheter tip against the endocardium 15". A delivery catheter (inside the steerable catheter) with an exemplary "compressed-spring" loaded device 50 is advanced into the infarct tissue 21. Once in position, the delivery catheter is withdrawn. The compressed spring device 50 is released. pushing the device with its anchors 40 apart shown in FIG. 26c. The spring device 50 is now embedded in the infarct tissue 21. The steerable catheter 60 is detached from the endocardium. and re-positioned. if needed. to place another device. To further the constraining effect of these devices. the device can be placed while the left ventricular volume has been temporarily decreased by different means such as inflating a balloon in the inferior vena cava.

Various versions of devices 50 can be embedded in the infarct tissue by this approach. Devices that are combinations of springs with restraining members can be embedded with this approach. "Fish-hook" type of devices to stiffen the infarct tissue can be embedded with this approach.

Figure 27A:
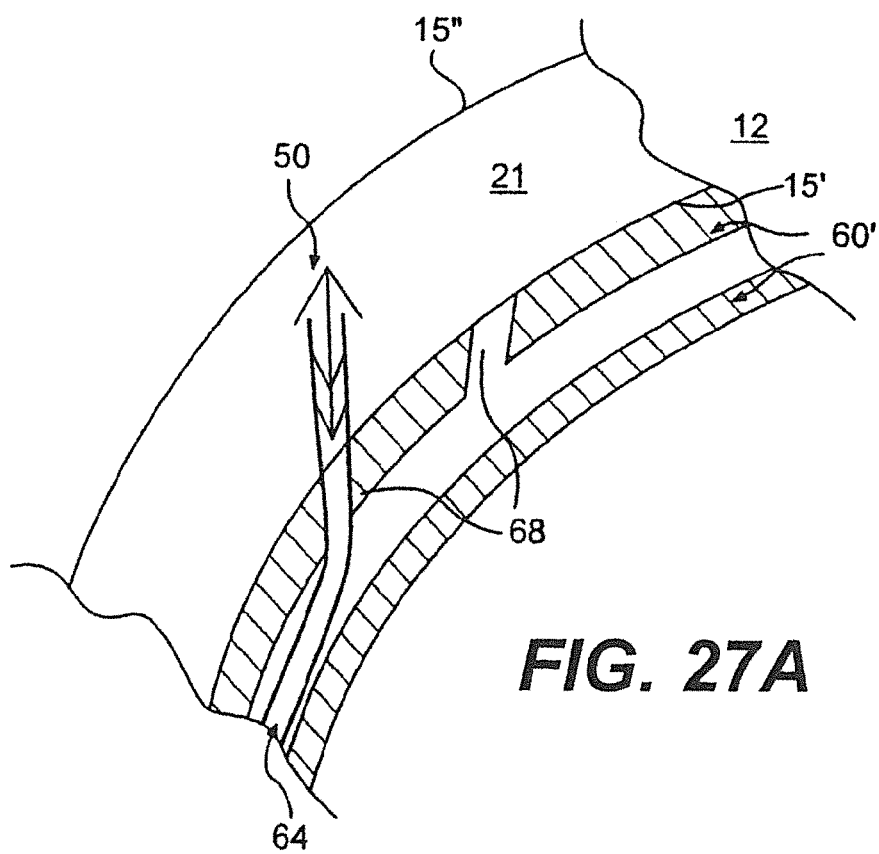
FIGS. 27A and 27B show a further exemplary embodiment of the present invention including a method for insertion.
Figure 27B:
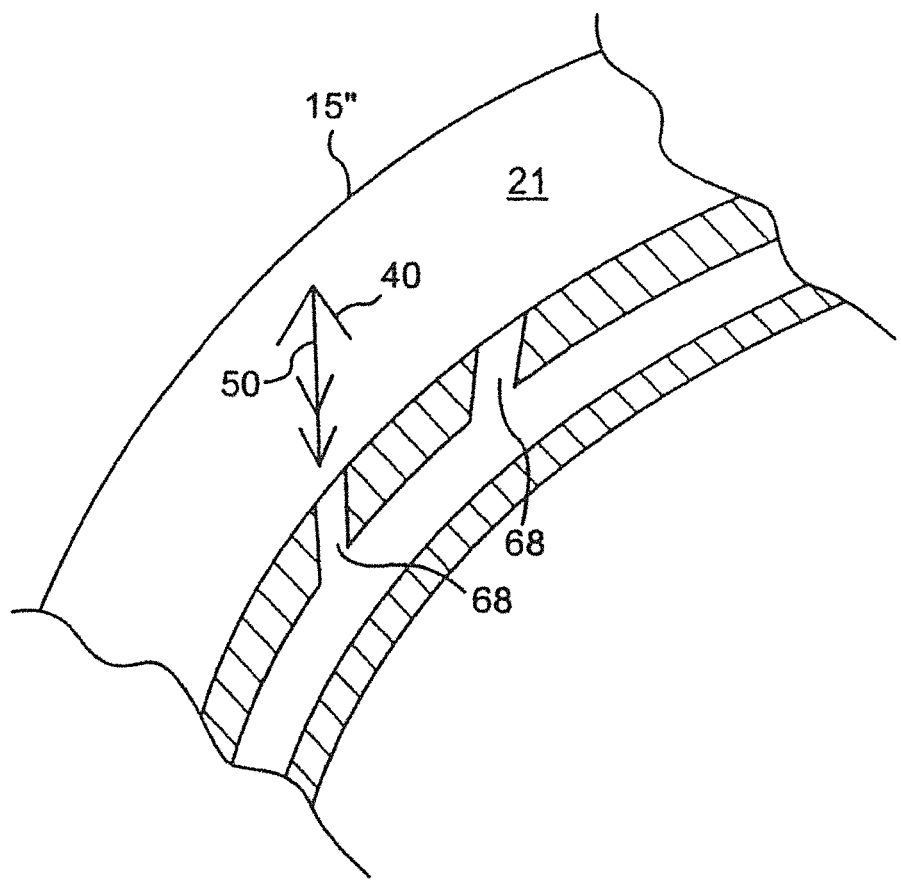

FIGS. 27a and 27b show a further illustrative means to implant a restraining device within infarct tissue. The area of myocardial infarction 21 is identified by one of the approaches discussed hereinabove. Via an artery such as the femoral artery, the steerable bow-shaped catheter 60' such as described in U.S. Pat. No. 5,855,577 is positioned in the left ventricle 12. The curvilinear shape serves to securely position the distal tip against the endocardial surface 15' of the left ventricle 12. The outer sidewall of the distal end of the catheter 60' has at least one guide hole. This hole is at an acute angle to the endocardial surface. This allows the device to be inserted into the left ventricular myocardium at an angle. A delivery catheter 64 situated inside the steerable bow-shaped catheter 60 can deliver a restraining device 50 into the infarct tissue. Once the device 50 is placed in position, the delivery catheter 64 is withdrawn. The restraining device 50 is released as the delivery catheter 64 is withdrawn. The restraining device 50 is now embedded in the infarct tissue 21. A second or third device can be similarly embedded in the infarct tissue through the guide holes 68 in the catheter. The steerable catheter is re-positioned, if needed, to place additional devices.

Various versions of stiffening, restraining, constraining, or combination devices can be embedded in the infarct tissue by this approach. Note that by using the bow-shaped catheter with multiple side-holes, the devices are placed in one direction or line.

Figure 28A:
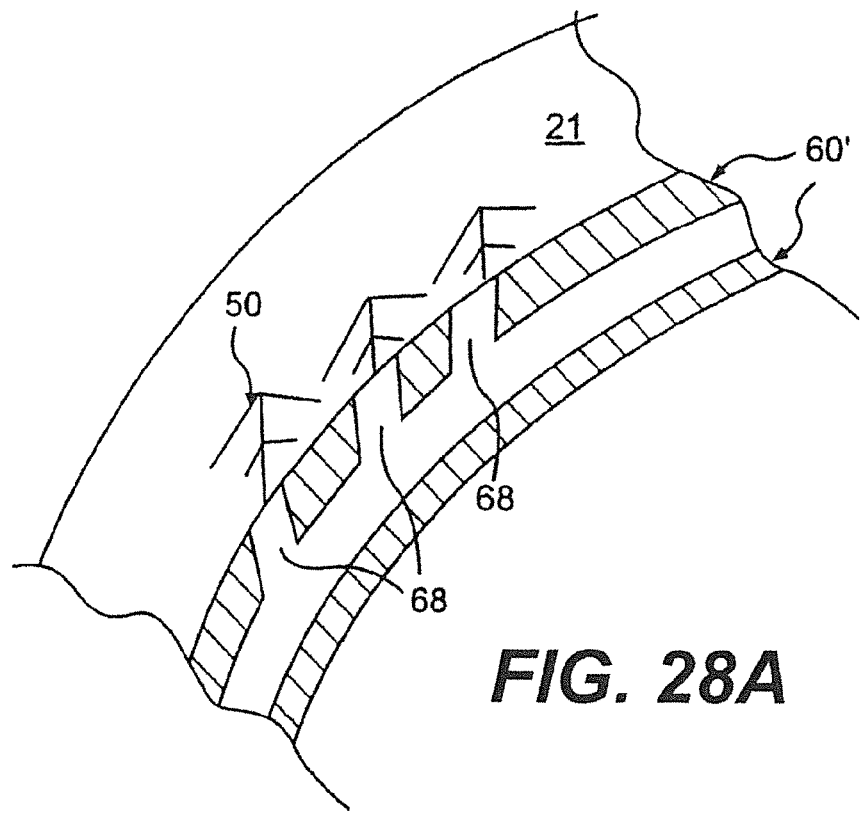
FIGS. 28A and 28B show a further exemplary embodiment of the present invention including a method for insertion.
Figure 28B:
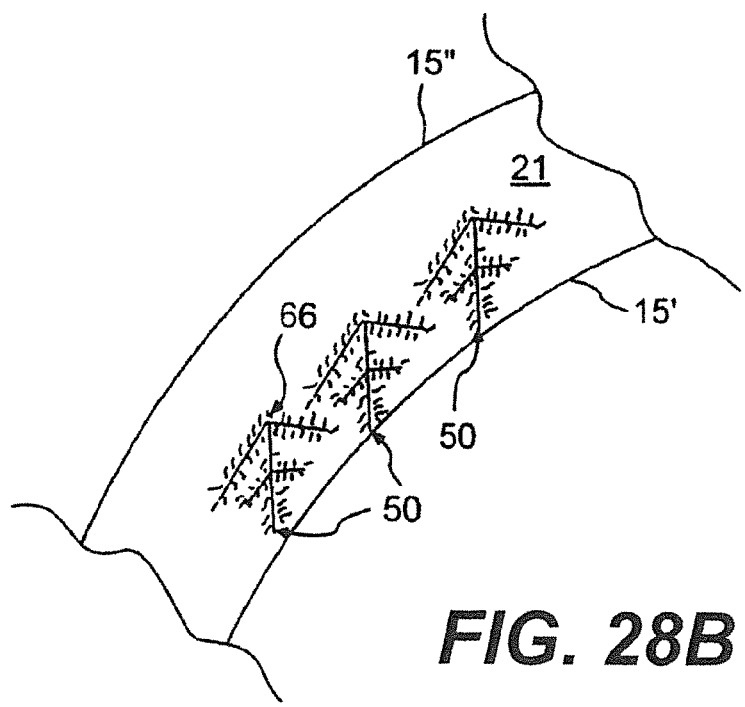

Using the approach illustratively depicted in FIGS. 28a and 28b, multiple "fishhook" or "tree" like devices 50 to stiffen the myocardium can be placed along one line or direction. The shape and size of the "fish-hook" like devices are matched to the space between the side holes 68 in the bow-shaped steerable catheter 60'. Once embedded in the infarct tissue 21, the devices 50 touch, or almost touch, each other. This close proximity further increases the stiffness of the infarct tissue. Over time, the devices 50 are encapsulated by scar tissue 66. The scar tissue 66 forms links between the individual devices.

Figure 29A:
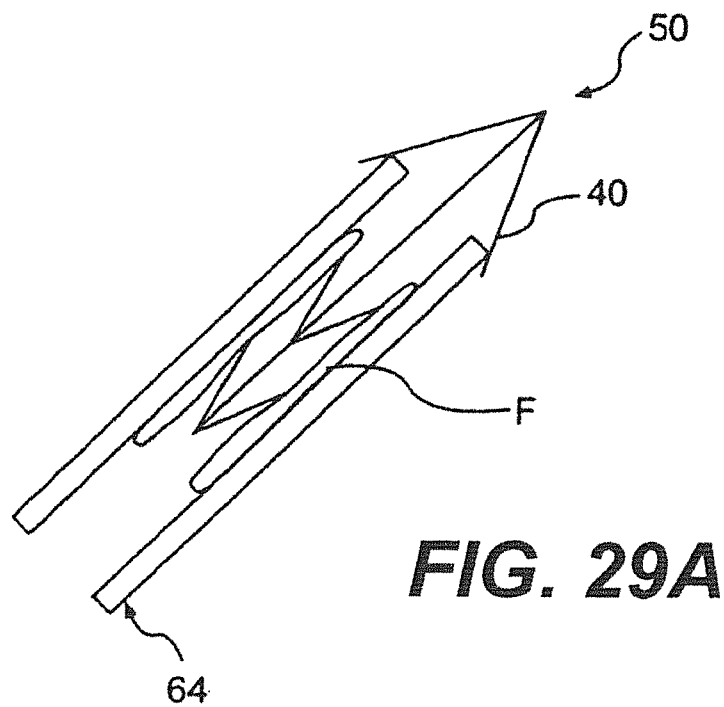
FIGS. 29A and 29B show a further exemplary embodiment of the present invention including a method for insertion.
Figure 29B:
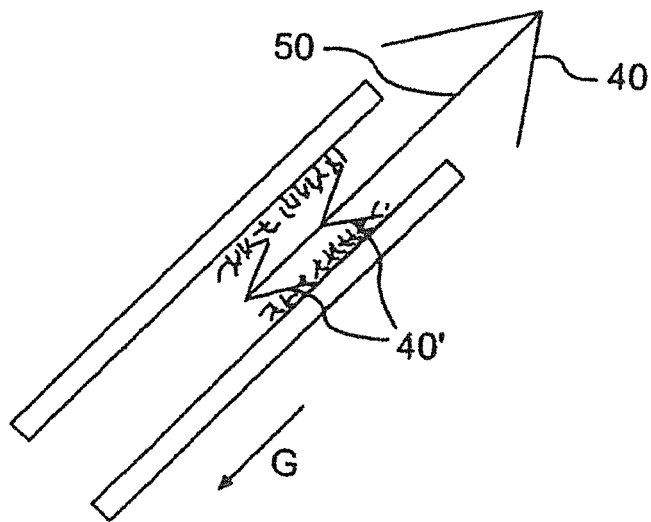

FIGS. 29a and 29b show that by having resistance in the deployment catheter• 64, or a similar de-coupler mechanism, the restraining device 50 can constrict the infarct tissue 21 between the two anchors 40. As previously described, the deployment catheter 64 can be pushed into the infarct tissue 21. Once in position, the deployment catheter 64 is gradually withdrawn. The distal anchor 40 on the restraining device is released and embedded in the surrounding tissue 21. As the deployment catheter 64 is further withdrawn, friction or resistance within the deployment catheter retards the release of the device SO. Thus, the distal anchor 40 is pulled towards the deployment catheter 64, thereby bringing the surrounding tissue 21 towards the deployment catheter 64. The proximal anchor(s) 40' is finally released, shortening the length of infarct tissue between the two anchors, decreasing the surface area of the infarct tissue 21, and increasing the wall thickness.

Figure 30:
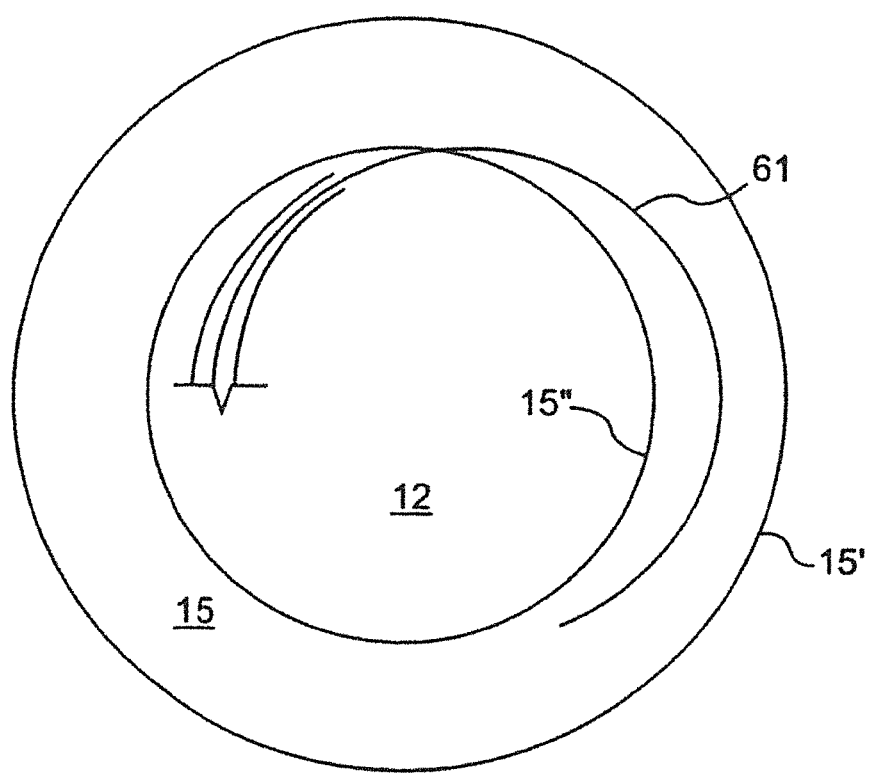
FIG. 30 is a schematic depiction of a guidewire inserted into the myocardium according to one aspect of the present invention.
Figure 31A:
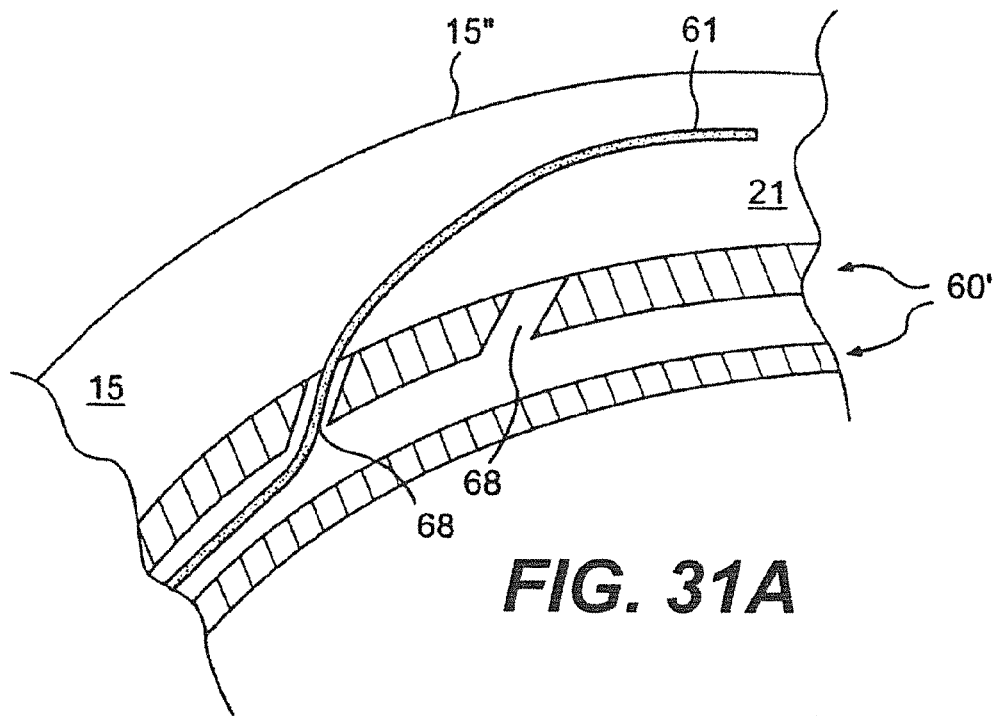
FIGS. 31A through 31D show a further exemplary embodiment of the present invention including a method for insertion involving a guidewire.
Figure 31B:
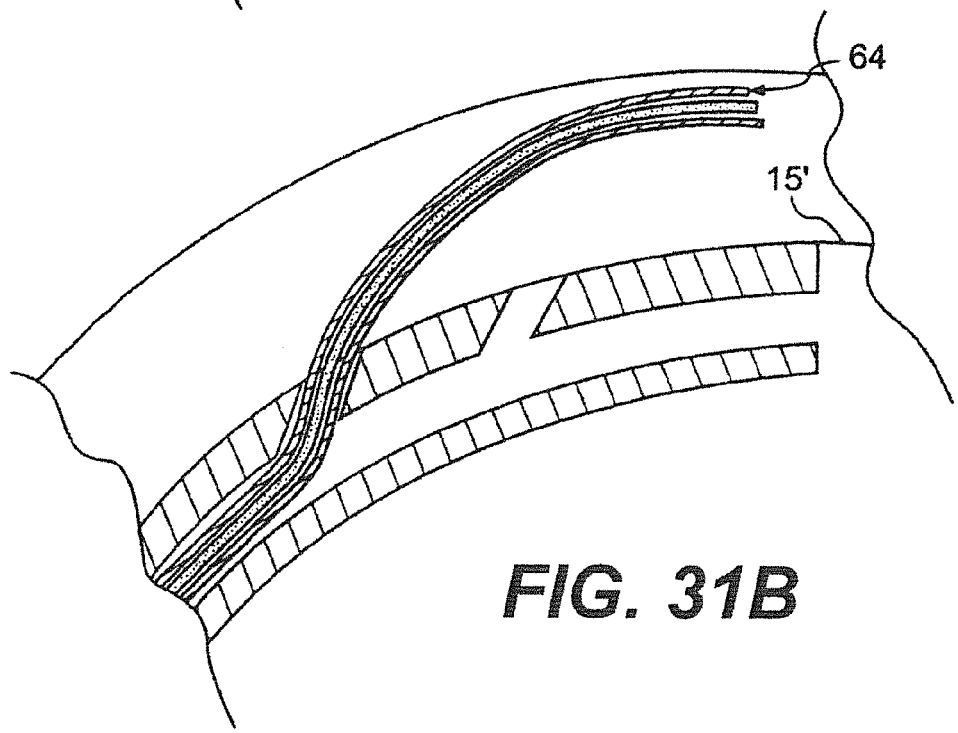
Figure 31C:
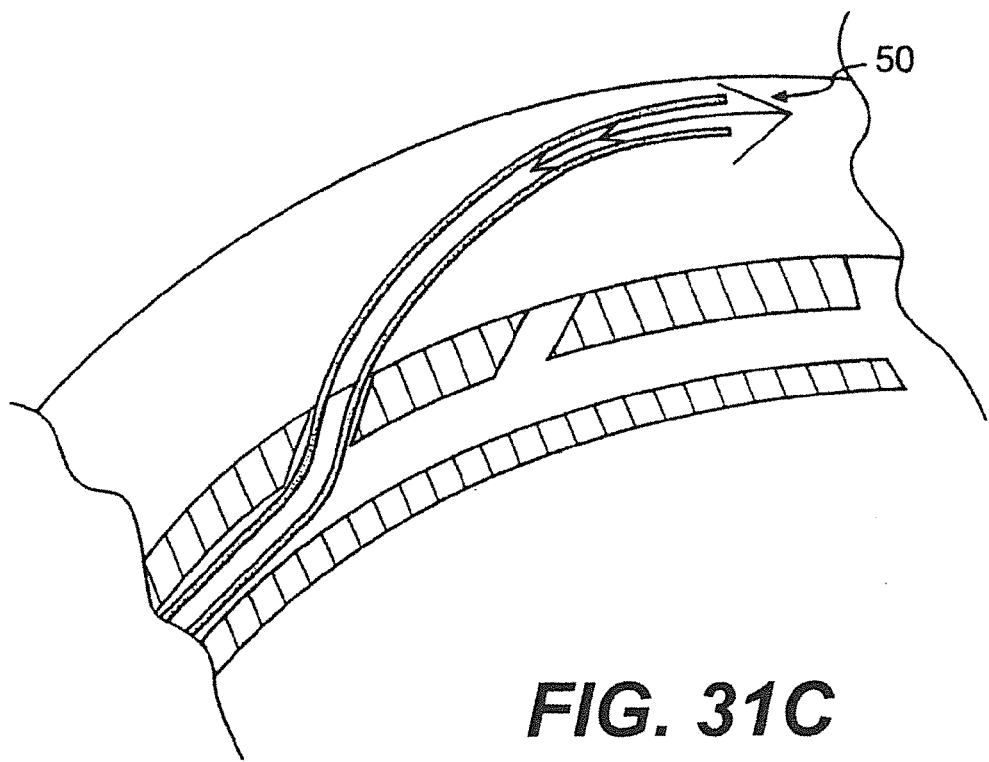
Figure 31D:
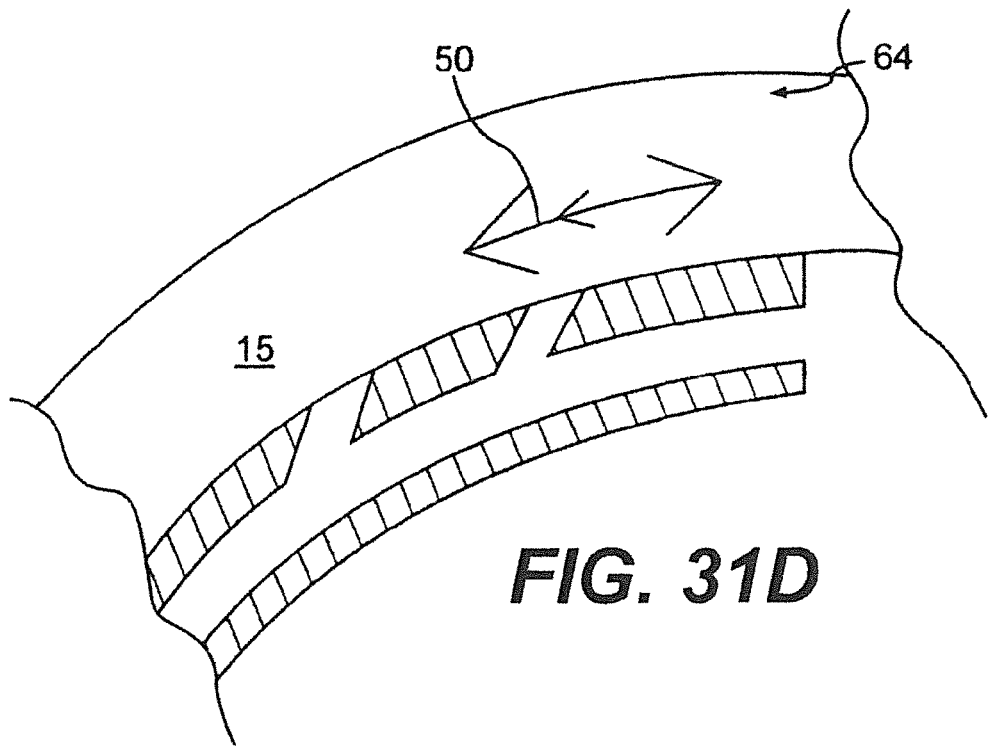

FIG. 30 shows a simple means to facilitate placement of devices within the myocardium. This figure shows a circular short-axis view of the left ventricle 12. From echo images, the curvature of the endocardial 1S" and epicardial surfaces 1S' can be determined prior to placing the devices. In this example, a steerable catheter is placed against the endocardial surface, as discussed above. A pre-shaped guidewire 61 having the same curvature as the endocardial surface 1S", is advanced into the myocardium 1S. By having this pre-shape, the guidewire 61 tends to stay near the middle of the myocardial wall 1S for a distance greater than a quarter of the total circumference.

The placement of devices can also be facilitated by using echocardiographic guidance. The echo images help to identify the regions of myocardial dysfunction. Additionally, the echo images can help with the positioning of guidewires or catheters within the myocardium. In real time, the echo images allow the exact positioning of these guidewires or catheters within the myocardium. This real time imaging makes placement of these devices easier. The depth of implant penetration can be monitored via a pressure port at the distal end of the catheter. Pressure sensed through the port is transmitted through the lumen and is detected by a pressure transducer. When in the left ventricular cavity, this pressure port measures dynamic left ventricular pressure. When the pressure port is submerged and covered by tissue, the pressure waveform becomes damped.

FIGS. 31*a* through 31*d* show a further exemplary arrangement to embed a restraining, constricting, or stiffening device 50 within the infarct tissue 21. The area of myocardial infarction is identified by one of the above approaches. Via an artery such as the femoral artery, the steerable bow-shaped catheter 60' such as described in U.S. Pat. No. 5,855,577 is positioned in the left ventricle against the endocardial surface 15" of the left ventricle 12. The outer arcuate sidewall of the distal end has at least one guide hole 68. This hole is at an acute angle to the endocardial surface 15". This allows the device 50 to be inserted into the left ventricular myocardium at an angle. This angle is further accentuated by using a pre-shaped guidewire 61 by described in U.S. Pat. No. 5,769,796. As described above, a pre-shaped guidewire 61 is pushed into the infarct tissue 21. Due to its curvature, the guidewire is positioned in the mid-wall and roughly parallel to the endocardial surface 15". Using echocardiography during placement further assists the positioning of the guidewire. The delivery catheter 64 is advanced over the guide-wire, which is withdrawn. A restraining device 50 is advanced through the delivery catheter and into the infarct tissue. Once in position, the delivery catheter 64 is withdrawn. The restraining device 50 is released as the delivery catheter 64 is withdrawn. The restraining device is now embedded in the infarct tissue 21. The device 50 is embedded in the infarct tissue 21, for example in a mid-wall position, parallel to the endocardial surface 15". A second or third device can be similarly embedded in the infarct tissue 21 through the other guide holes 68 in the catheter. The steerable catheter 60' is repositioned, if needed. to place additional devices. The device 50 can be positioned anywhere in the tissue and needn't be placed mid-wall as illustrated.

Figure 32A:
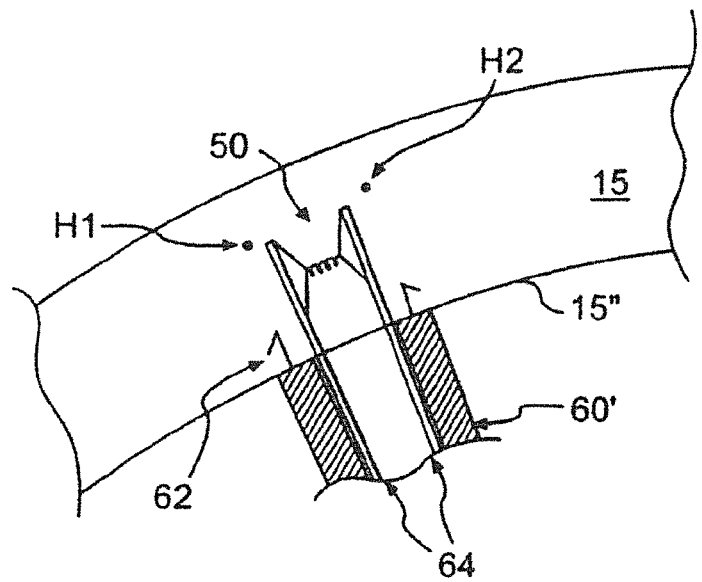
FIGS. 32A and 32B show a further exemplary embodiment of the present invention including a method for insertion.
Figure 32B:
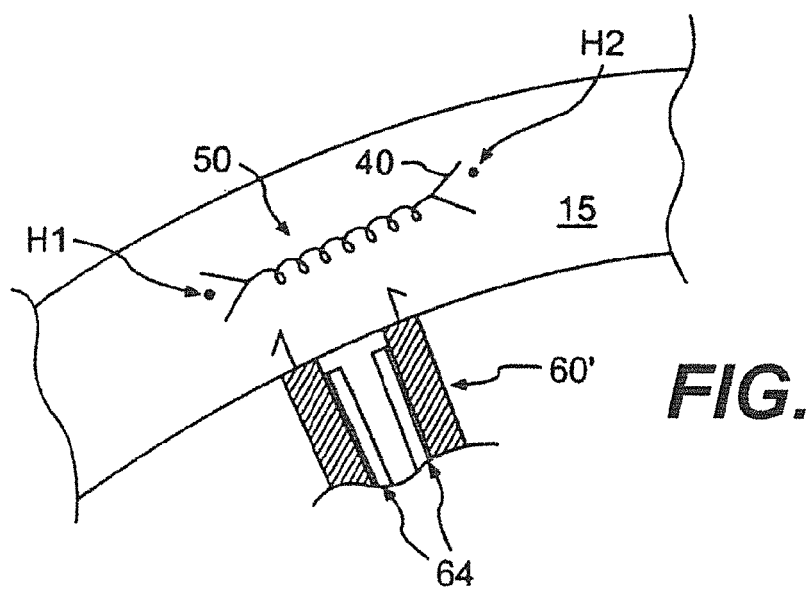

The above figures have described deployment of devices to restrain, constrain, or stiffen myocardial infarct tissue. Many of the same approached can be used to deploy devices that treat diastolic heart failure and mitral regurgitation. In diastolic heart failure, the systolic ventricular function is preserved. However, the decreased diastolic ventricular compliance prevents the left ventricle from filling in diastole. Using the approaches described above, FIGS. 32*a* and 32*b* show one embodiment for expanding the heart in diastole to treat diastolic heart failure. Via an artery such as the femoral artery, the steerable catheter 60' is positioned in the left ventricle. The tip of the catheter 60' is positioned against the endocardial surface 15", and anchors 62 hold the catheter tip against the endocardium. A delivery catheter 64 inside the steerable catheter 60' with, for illustrative purposes, a "expansion-spring" loaded device 50 in a compressed mode is advanced into the myocardial tissue 15. Once in position, the delivery catheter 64 is withdrawn. The expansion spring device 50 is released, pushing the device with its anchors 40 apart. The device 50 is now embedded in the myocardial tissue 15 and has expanded the myocardial tissue (points H1 and H2 in FIG. 32*b* are further apart). The effects of this device deployment are assessed at the time by measuring left ventricular pressure and dimensions or volume. The goal is to increase left ventricular end-diastolic volume, while maintaining or decreasing left ventricular end-diastolic pressure. If needed, the steerable catheter 60' is detached from the endocardium 15", and re-positioned to place another device. This repositioning can be facilitated by a steerable catheter 60' with a main anchor that allows the catheter to pivot around this anchor point as shown in U.S. Pat. No. 6,248,112, the contents of which are incorporated herein by reference. To further the expansion effect of these devices, the device can be placed while the left ventricular volume has been temporarily increased by different means such as intravenous fluids. Additionally, these devices can be placed in set directions for greater effect.

Figure 33A:
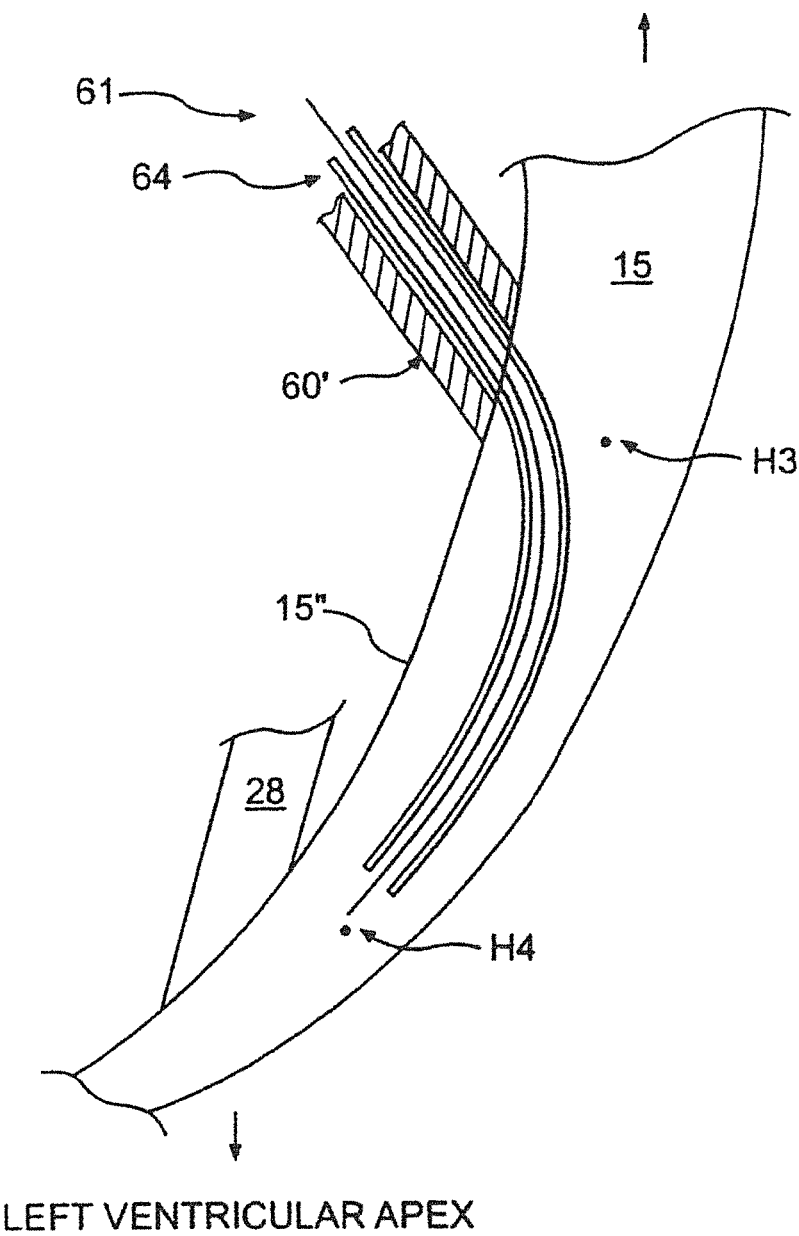
FIG. 33A shows a further exemplary embodiment of the present invention including a method for insertion involving a guidewire.

Mitral valvular regurgitation can occur due to enlargement of the orifice and an increased length from the valve plane to the base of the papillary muscle. This increased length places tension of the cordae tendinae, preventing the valve leaflets from closing properly. Decreasing the orifice size and/or decreasing the length from the valve plane to the base of the papillary muscle will decrease the mitral regurgitation. Using an approach similar to that illustrated in FIG. 33*a*, a device 50 to treat mitral regurgitation can be deployed. Via an artery such as the femoral artery, the steerable catheter 60' is positioned in the left ventricle against the endocardial surface 15' of the left ventricle. As shown in FIG. 33*a*, a pre-shaped guidewire 61 is pushed into the tissue 15. Due to its curvature, the guidewire 61 is positioned in the mid-wall and roughly parallel to the endocardial surface 15' in the base-toapex direction. Using echocardiography during placement further assists the positioning of the guidewire 61. The deployment catheter 64 is advanced over the guidewire 61, which is withdrawn. A restraining device 50 is advanced through the delivery catheter 64 and into the tissue. The distal anchors on the restraining device 50 is released and embedded in the surrounding tissue. As the deployment catheter is further withdrawn, friction or resistance within the deployment catheter 64 retards the release of the device 50. Thus, the distal anchor is pulled towards the deployment catheter 64; thereby bringing the surrounding tissue towards the deployment catheter 64. Echocardiography, preformed during this deployment, is used to assess mitral regurgitation. The amount of tension on the device 50 can by adjusted to reduce mitral regurgitation. The proximal anchor is finally released I shortening the tissue between the two anchors (illustrated by points H3 and H4 in the FIG. 33*a*). The distance from the mitral valve plane to the base of the papillary muscle is decreased, thereby reducing mitral regurgitation. A second or third device can be similarly embedded in the tissue, if needed to further pull the base of the papillary muscles towards the mitral valve plane. Using the same approach, devices can be placed to reduce the mitral valve orifice size.

Once in the myocardium, individual or multiple devices can be released. The system that deploy multiple devices generally have these devices in the catheter and use a difference approaches (friction, electrical) to detach one device at a time.

Some embodiments of the present invention can be configured to have a plurality of implants and configured to deliver the implants sequentially to a plurality of locations. To facilitate delivery of multiple implants, a delivery catheter can be constructed with an eccentrically located guidewire lumen on the catheter. After anchoring the guidewire on the endocardial surface, the steerable catheter can be advanced over the guidewire to become positioned against the endocardium. To facilitate delivery of multiple implants, the guidewire lumen of the delivery catheter may be eccentrically located on the catheter. The catheter can rotate around the anchored guidewire to encompass a broader delivery area with only a single guidewire placement.

Figure 34A:
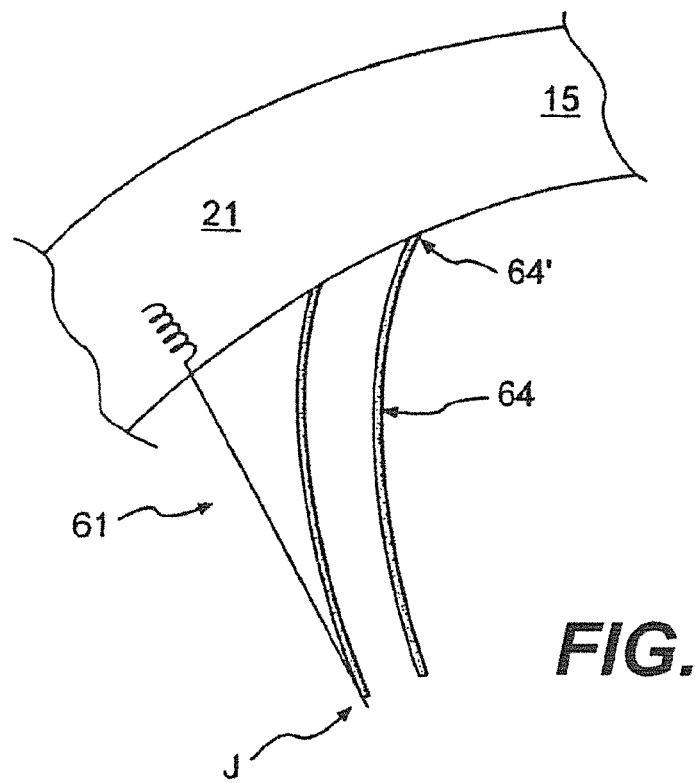
FIGS. 34A and 34B show a further exemplary embodiment of the present invention including a method for insertion involving a coil.
Figure 34B:
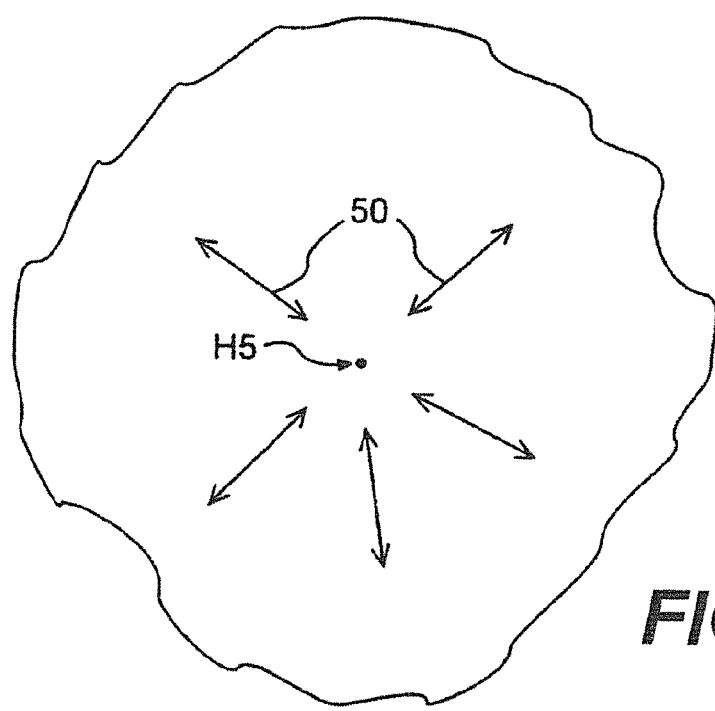

FIGS. 34a and 34b show a means to embed several restraining, constricting, or stiffening device 50 within the infarct tissue 21. The area of myocardial infarction is identified by one of the above approaches. Via an artery such as the femoral artery, a catheter is positioned in the left ventricle. A guidewire 61 with an anchor is positioned against the endocardial 15' surface. The guidewire 61 is anchored into the myocardium 15. The tip of the guidewire (the anchor itself) is used to measure local electrical activity to reconfirm that the anchor is in the desired type of tissue (i.e., electrical activity levels can discriminate infarcted, peri-infarct, and viable tissue). The catheter 60' is removed, and a steerable delivery catheter 64 is advanced over the guidewire. The guidewire lumen is eccentrically positioned within this delivery catheter as indicated-at arrow J. This eccentric position allows the delivery catheter to rotate around the anchor point, thus enabling multiple devices to be implants within a region. The delivery catheter is positioned against the endocardial surface 15'. A beveled tip 64' on this catheter allows the device 50 to be inserted into the left ventricular myocardium at an angle as shown in FIG. 34a. A restraining or constraining device 50 is advanced through the delivery catheter 64 and into the infarct tissue 21. Once in position, the delivery catheter is rotated around the anchored guidewire 61 and another device is implanted. Using this approach, multiple devices are implanted to encompass a broad area with only a single guidewire placement at point H5, as shown in FIG. 34b, looking from the endocardial surface into the myocardium.

FIGS. 35a and 35b show an illustrative arrangement to embed multiple devices into the myocardium and link these devices together. As shown in FIG. 35a, a catheter 64 is positioned in the left ventricle against the endocardial surface. A coil-like device 120 within the catheter is advanced into the myocardium 15. In the catheter, this coil-like device 120 is in a straightened shape. The coil-like device can be made from a shape memory material such as nitinol. Upon exiting the catheter 64, the coil-like device assumes its normal, coiled shape. By this approach, the distance across the coils is greater than the diameter of the delivery catheter. After placing the coil 120, the catheter is moved radially from the first coil to a distance less than the coil diameter. This radial motion is controlled by means of a linking mechanism, which can later be removed, if needed. The second coil-like device is advanced into the myocardium, and becomes intertwined with the first coil-like device. This process is repeated, leaving multiple linked coil-like devices within the myocardium 15, as shown in FIG. 35b.

FIGS. 35c and 35d show ways to facilitate the linking of devices 120. In FIG. 35b, the delivery catheter 64' has a plurality of off-set lumens. Through one lumen, the coil-like device 120 is advanced into the myocardium 15. Through another lumen, a rod like device 122 is advanced into the myocardium 15. The rod 122 is within the coils 120 of the device in situ. The catheter 64' is moved radially from the first coil, and another coil and rod are inserted into the myocardium as shown in FIG. 35d. The second coil-like device 120 engages the first rod 122, thus ensuring linkage between the devices. This procedure is repeated to place the desired number of devices.

Turning to FIG. 35e, the coil direction (left hand screw, right hand screw) of the coil 120 can be alternated (120, 120') left-right-left, etc., from coil to coil to promote linkage between the devices. Of course, the illustrative devices described in this specification may be employed to constrain tissue.

Figure 36A:
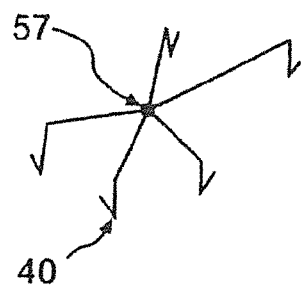
FIGS. 36A through 36D show a further exemplary embodiment of the present invention including a tightening arrangement.
Figure 36B:
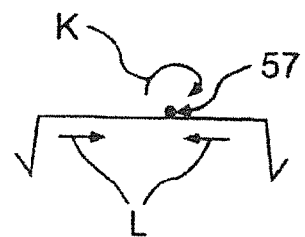
Figure 36C:
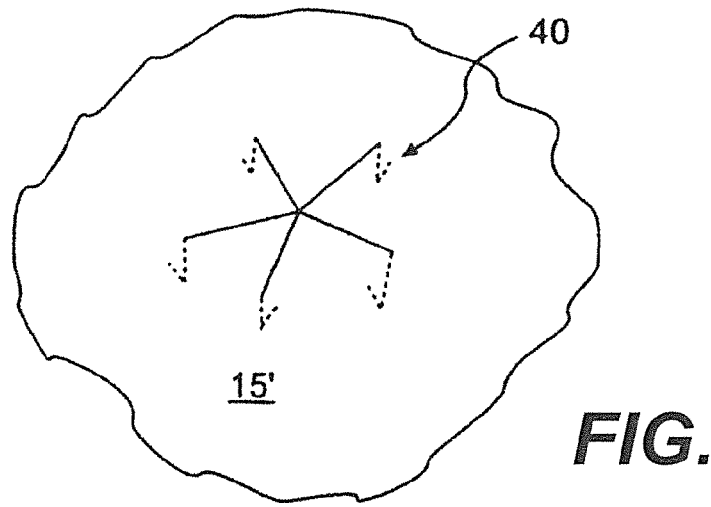
Figure 36D:
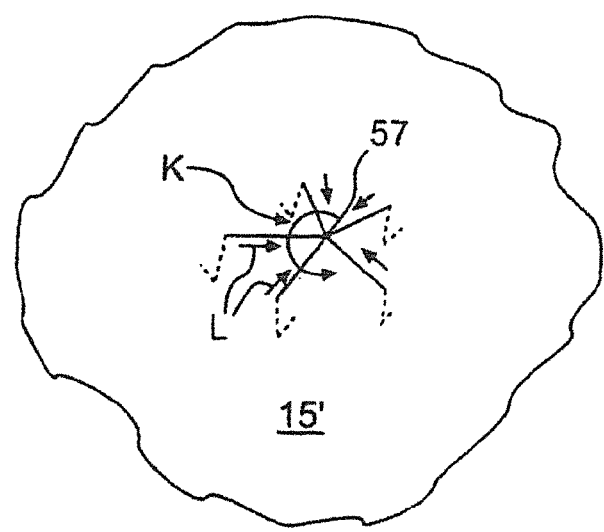

Turning now to FIG. 36a, a spider-like device 50 is depicted that has a central. tightening mechanism 57 and multiple arms with anchors 40 radiating out from the center. The arms can be restraining type devices, constraining devices, or a combination. As shown in FIG. 36b, as the central mechanism is tightened in the direction of arrow K for instance, and the arms are pulled towards the center in the direction of arrows L. FIG. 36c shows this device implanted within the myocardial tissue at the epicardial surface 15'. In FIG. 36d, tightening the device in the direction of arrow K for instance pulls the arms in the direction of arrows L and decreases the distance from the anchor points to the central tightening mechanism 57.

FIGS. 37a through 37d show a restraining device 50 with multiple anchor points 40 that are imbedded within the myocardium and body parts 52 between the anchor points 40. As shown in FIGS. 37b and 37c, this type device can be placed in various patterns to achieve the maximal desired effect on altering regional myocardial wall characteristics. FIG. 37d shows that this can also be a constraining device using spring like body portions 52', and of course combinations of body parts are also possible.

Devices can be made of shape memory polymers, such as polymorborene. This material can be elongated at a temperature above its critical temperature. The material remains elongated until heated again when it shortens to its original length and shape. The material can be inserted into the infarct tissue, and later heating of this region causes the material to shrink, thereby constricting the infarct tissue.

Figure 38:
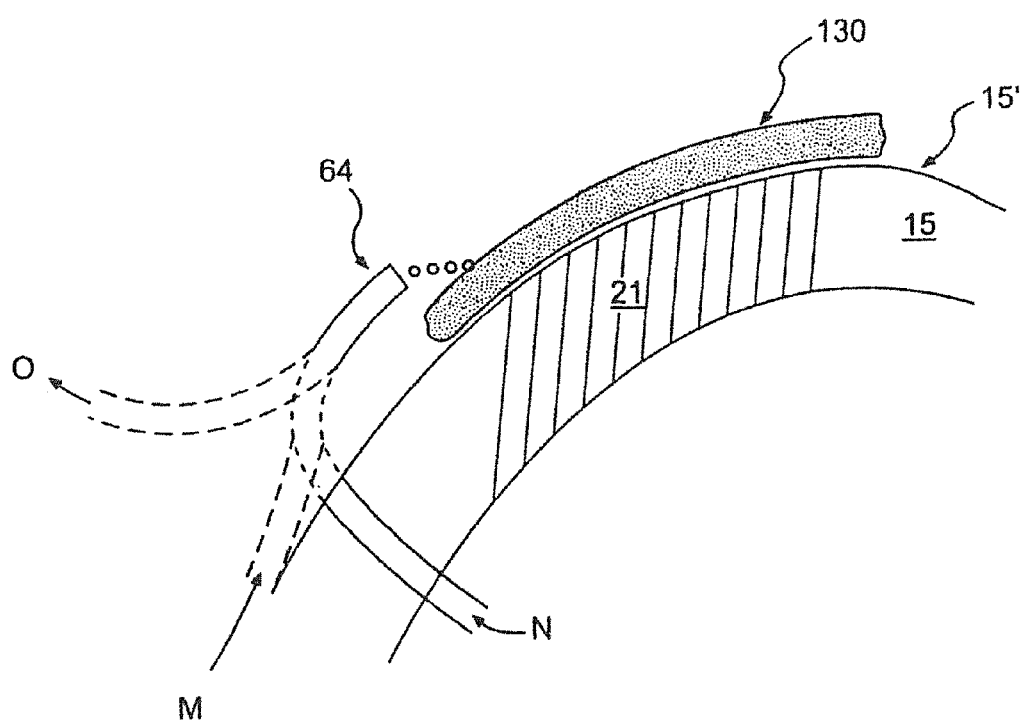
FIG. 38 shows a further exemplary embodiment of the present invention comprising a polymer or other material deposited on the surface of the myocardium.

As shown in FIG. 38, a device 130 comprising a fabric mesh made of a biocompatible material can be sutured onto the myocardium. Later heating again causes the material to shrink. The material can by its mechanical characteristics and by linking with the myocardium limit expansion of the myocardium by the infarct tissue. This method may be practiced through an open chest or mini-thoracotomy approach, where the catheter 64 would be placed from the direction of arrow 0, or a minimally-invasive approach using either a coronary vein (arrow M) or from a left ventricular artery (arrow N). Accordingly, during open chest surgery or through a minimally invasive approach, the material can be injected onto the endocardial surface. Via a percutaneous approach, a catheter 64 as shown is positioned in the left ventricle. The catheter is positioned against the endocardial surface by the myocardial infarction, and a guidewire is advanced through the myocardium and into the pericardial space. The delivery catheter is pushed over the guidewire into the pericardial space, as discussed above in related delivery methods. The guidewire is removed, and the material is injected through the delivery catheter onto the epicardial surface of the heart. A coronary venous approach can also be used. A guidewire is advanced through the coronary sinus and positioned in a coronary vein close to the infarcted tissue. The guidewire is then pushed transluminally through the venous wall and into the pericardial space. The delivery catheter is pushed over the guidewire into the pericardial space. The guidewire is removed, and the material is injected through the delivery catheter onto the epicardial surface of the heart. As the delivery catheter is pulled back into the coronary venous system, a small amount of material is injected to occlude the hole in the coronary vein.

Figure 41B:
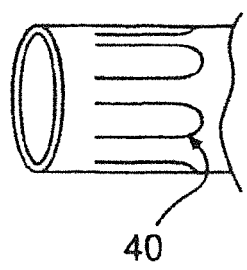
Figure 41C:
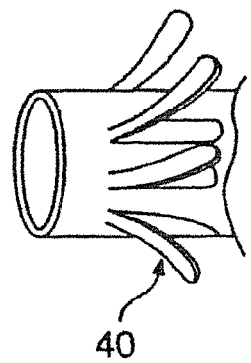
Figure 41D:
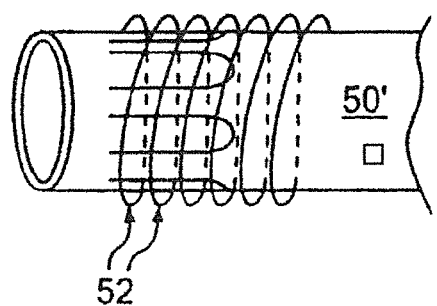
Figure 41E:
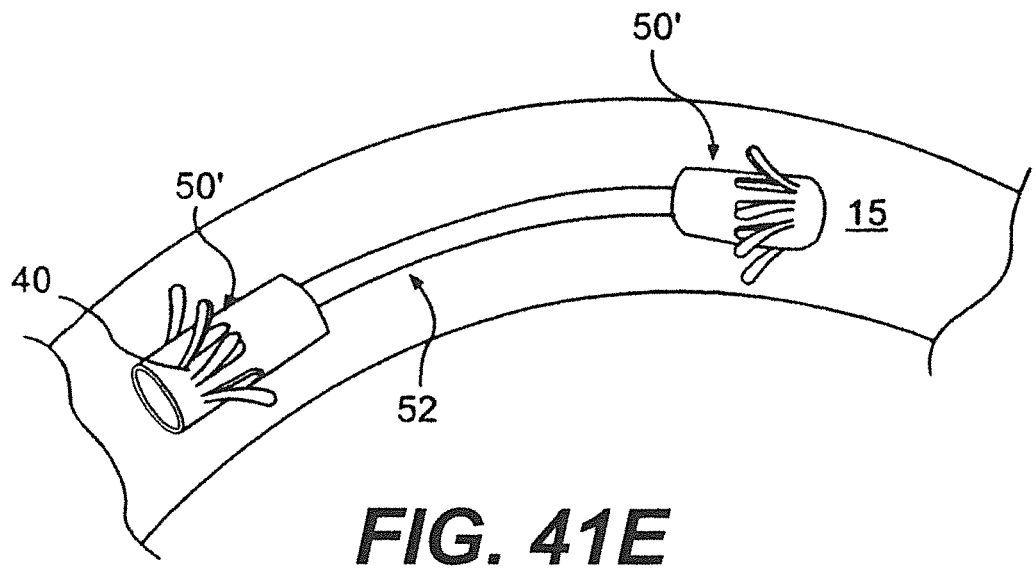
Figure 41F:
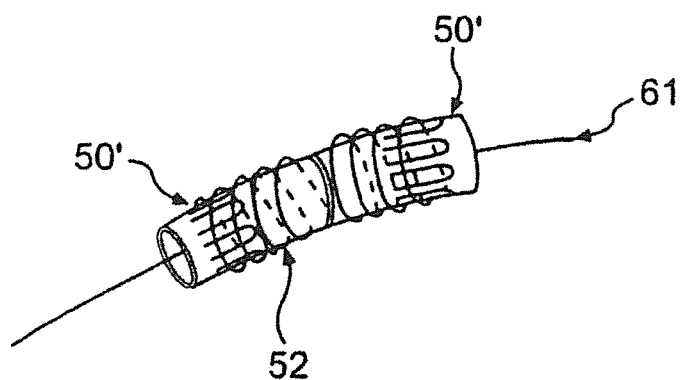

The present invention also includes devices that relate to the concept of reducing stresses in myocardial tissue by placing a device in the myocardial wall such that the device itself carries some of the loads usually carried by myocardial tissue alone. An illustrative device 50 suitable for placing in myocardial tissue is one with a generally tubular configuration as shown in FIG. 39. FIGS. 40a and 40b are a front view and a side view, respectively, of the device of FIG. 39. The device comprises a tubular body 52 with at least two expandable anchor features 40, at least one at each end. Anchor features 40 can be formed by cutting several circumferentially spaced lengthwise slots 41 through the wall of the tube along a portion of its length and then forming the material between the slots into section bulged configuration as shown in FIG. 40b. Alternatively barbs can be created in a similar fashion of slotting and forming. This configuration is shown in FIG. 41a. In addition to the anchor elements at each end of the tubular body it may be desirable to create several anchor elements along the length of the tubular body. FIG. 41b illustrates the anchors 40 in a collapsed configuration, and FIG. 41c shows the anchors 40 deployed. Delivery can be performed through catheter based methods, or other methods, described herein or as known in the art. FIG. 41d through 41f show a modification where the body 52 is comprised of a wire or suture material which tethers device ends 50' together. The body portion 52 can also serve to constrain the barbs 40 in a retracted position. Delivery of device ends 50' which can comprise a central lumen can be effectuated over a guidewire. When the device ends 50' are urged apart, the body part 52 slides from the barbs 40 allowing them to deploy. The body part 52 then serves to tether the device ends 50' together under tension. Another advantage of this telescoping tube design is that body parts that may be difficult to push through a catheter can now be easily pushed through a catheter. Of course. the body part 52 can be any mechanical means for constraining the barbs into a collapsed position, and needn't be a wire or suture as depicted. For instance, the telescoping embodiments could comprise bearing surfaces that overlie the anchors 40 to maintain them in a constrained position until the device is deployed.

Both the barb type and bulge type anchors are of such a configuration that they may be elastically deflected back into a tubular geometry. When deflected in this manner the device may. be placed into the lumen of a catheter not much larger in diameter than the device itself. Placement in such a catheter facilitates placement of the device in the myocardium as will be described below.

Figure 42:
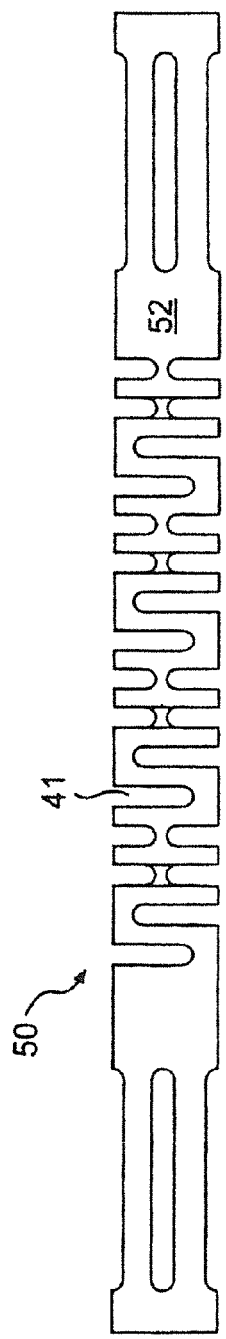
FIG. 42 shows a configuration for an alternative device similar to the embodiment depicted in FIG. 39.

The section of tube between the anchor elements may be rendered laterally flexible by cutting transverse slots in the tube material as shown in FIG. 42. Many other cutout geometries can be created in order to modify the lateral flexibility of the device and to adjust the longitudinal flexibility as well. Ideally the cut-out configuration will allow some amount of lateral shortening relative to the nominal length the device assumes when initially placed in the myocardium but, the cut-out configuration should be such that longitudinal lengthening beyond the devices nominal length will not occur or occur to only a limited degree. In this exemplary embodiment, the tube can be formed from nitinol, for example, with a 0.045" outside diameter and a 0.005" wall thickness. The slot width can be about 0.003" to about 0.005", with the resulting pattern formed from struts of about 0.012" to 0.015". Overall length can typically be from about 1.0 to about 2.0 inches.

Figure 43:
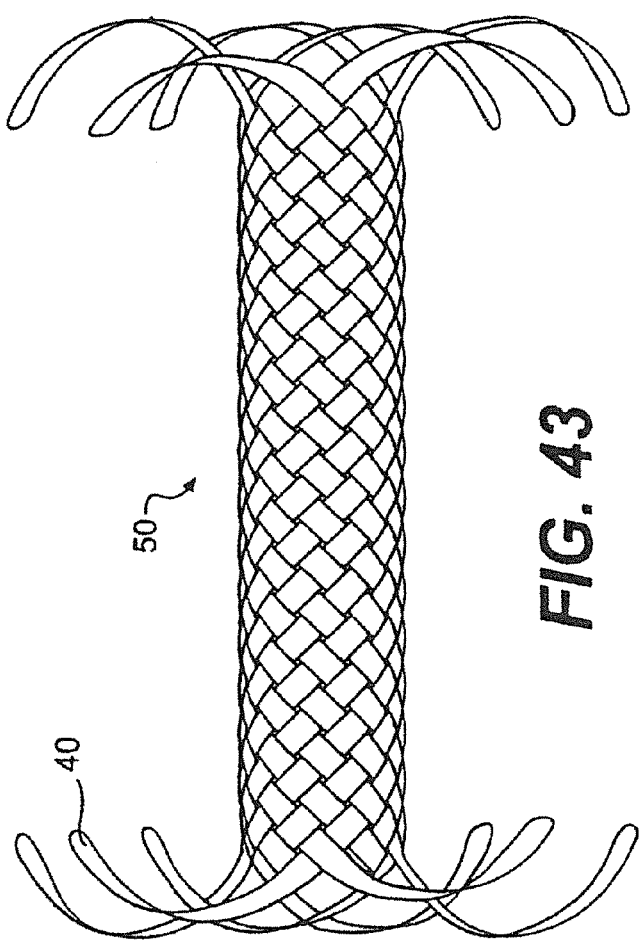
FIG. 43 shows a further embodiment of the present invention having a braided construction.
Figure 46A:
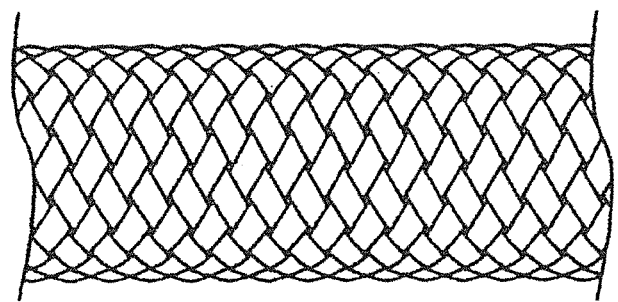
FIGS. 46A and 46B show the behavior of braided material during compression and tension on the top and bottom, respectively.
Figure 46B:
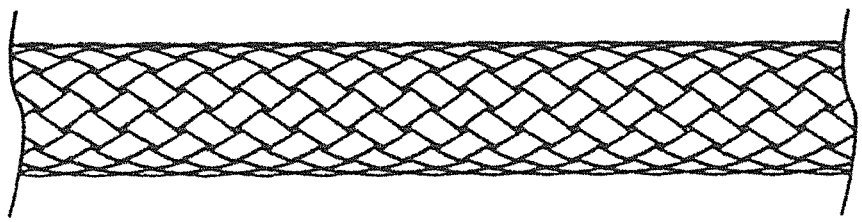

Another tubular configuration for inter-myocardial stress reducing devices is that of a tubular braid of material as shown in FIG. 43. The braid may be constructed of round or flat wire. End anchor elements 40 are created by unbraiding some portion of each end of the braid and turning the unbraided ends back over the body of the braid as shown. Additional anchors may be created by weaving in short length of material as shown in FIG. 44. Alternatively if the braid tube is made by braiding flat wire 140, an exemplary dimension of which might be 0.004'W×0.001'1, configured as shown in FIG. 45 then the braid tube will have a multitude of small anchor elements 142 along its entire length. Tubular braid has the desirable property of being able to shorten or lengthen in response to forces applied longitudinally to the ends of the braid. The geometric interactions of the wires which comprise the braid are such that once a maximum stretched length is established the force to cause further elongation increases dramatically. Likewise a dramatic increase in force is needed to cause shortening below a minimal length. The force to cause lengthening or shortening between these two extremes is very low. The inventors propose that the reason for these limits on lengthening and shortening is likely as follows. As the braid is lengthened its diameter decreases and the wires comprising the braid grow closer together circumferentially. When the diameter reaches a size such that there is no longer any circumferential distance between the wires then no further lengthening can occur. Likewise when the braid is shortened the longitudinal spacing between the braid wires decrease and eventually becomes negligible, thereby preventing any further shortening. These two states are shown schematically in FIGS. 46A and 46B. To employ this property of the braid to greatest effect in supporting myocardium the braid would be inserted into myocardium during diastole in the fully elongated state. Hence the braid may contract in systole and not impede normal contractile function.

Figure 47A:
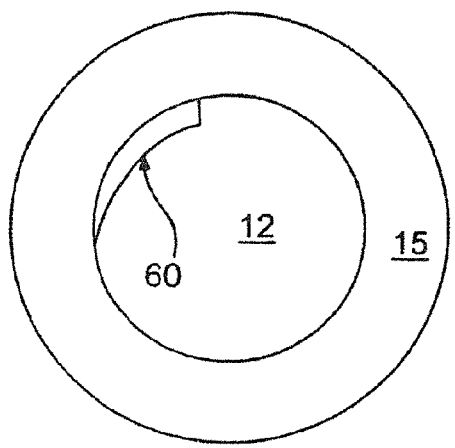
FIGS. 47A through 47D show an alternative embodiment of the present invention including a method of intracardiac delivery involving a guidewire.
Figure 47B:
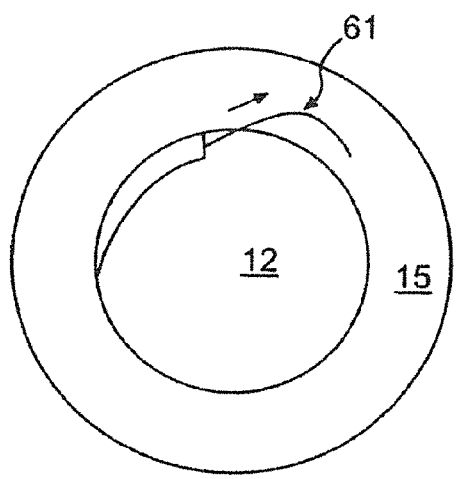
Figure 47C:
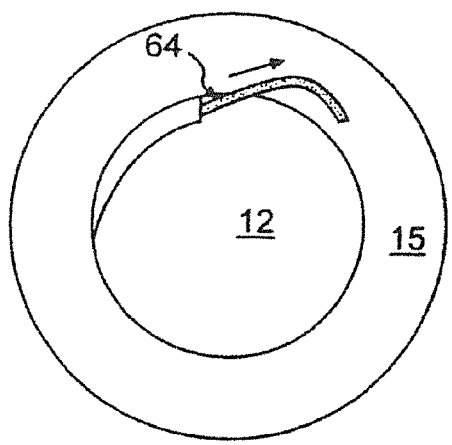
Figure 47D:
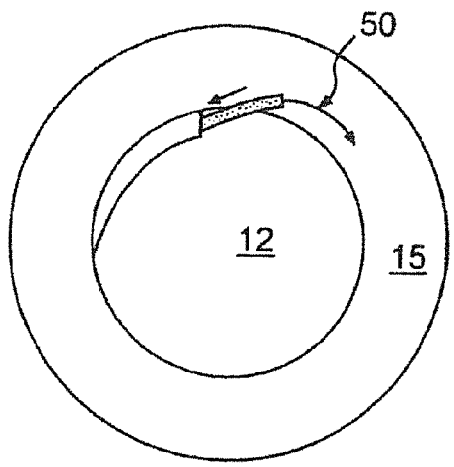

Insertion of these tubular devices into the myocardium may be accomplished as illustrated in FIGS. 47a through 47d. A guide catheter 60 is inserted into the left ventricle 12 and positioned proximal to the desired insertion point for the device as shown in FIG. 47a. A guidewire 61 is then inserted through the guide catheter and into the myocardium 15 following the path along which it is desired to insert the device, as shown in FIG. 47b. Navigation of the 64 guidewire 61 may be accomplished by using a wire so constructed as to allow deflection of the distal tip of the guidewire in any radial direction when a deflection means located at the proximal end of the guidewire is appropriately manipulated. Such wires are commercially available. Once the wire is in place, a deployment catheter 64 with the device 50 loaded in its distal end is inserter through the guide catheter and over the guidewire 61. as depicted in FIG. 47c. Next the guidewire is removed and a stylet can be inserted just up to the distal end of the device (which is still contained in the lumen of the deployment catheter). The stylet can be held fixed relative to the guide catheter 64 and the myocardium 15 while the deployment, catheter is pulled back, freeing the device and allowing its anchoring means to deploy and fasten to the myocardium, as depicted in FIG. 47d.

Figure 48:
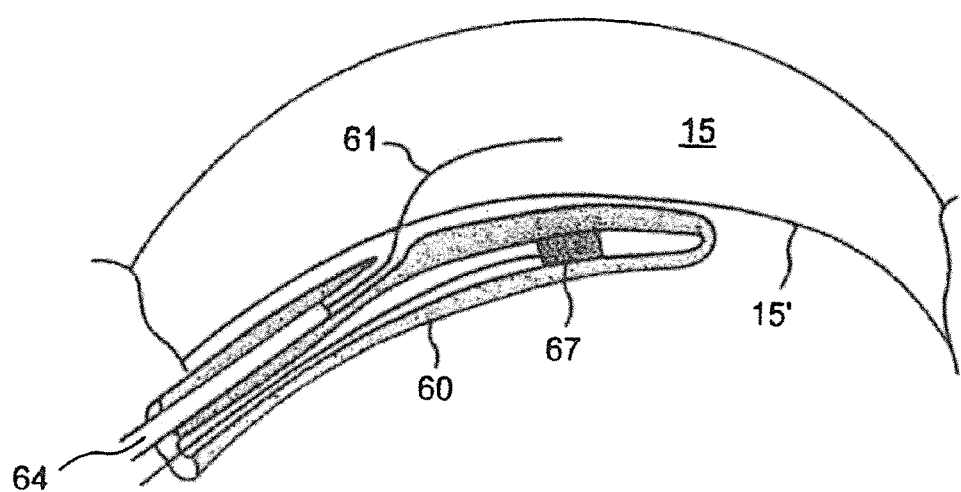
FIG. 48 shows a still further embodiment of the present invention including a method of intracardiac delivery involving a probe.

Navigation of the guidewire may be facilitated by using an alternative guide catheter configuration as shown in FIG. 48. This guide catheter 60 has two lumens. One lumen is used to deploy the guidewire 61 and deployment catheter 64 in a manner equivalent to that described above however the guidewire 61 or deployment catheter 64 exit the guide catheter 60 through a side hole at a point a few centimeters proximal to the guide catheter's distal tip. The second lumen contains a guidewire location sensor 67 assembly and the portion of the guide catheter from the side hole forward to the tip contains the actual guidewire location sensor. This portion of the catheter lies along the interior LV wall at a location proximate to the desired path of the device. The sensor assembly may move in its lumen relative to the guide catheter. This sensor is preferably an ultrasonic imaging array constructed in a manner similar to intravascular ultrasound (IVUS) sensors. Outside the patient at the proximal end of the guide catheter the deflectable guidewire and the sensor assembly are tied together so that the tip of the guidewire moves with the location sensor so that distance along the catheter to the guidewire tip is the same as the distance along the catheter to the sensor and the guidewire tip and sensor stay laterally adjacent to one another while the guidewire is advanced into the myocardium. In this manner the image created by the ultrasound sensor will always be the image of the tip. Now navigation of the guidewire is simply a matter of advancing the guidewire and sensor assembly, watching the ultrasound image and manipulating the guidewire deflection control so that the wire tip stays the desired distance from the LV inner and outer walls. Imaging of the wire may be enhanced by using a wire containing an ultrasound transmitter that is linked to the ultrasound imaging system. In such a system signals are sent from the wire to the imaging sensor that are much stronger than those created by the reflection of waves transmitted by the imaging sensor.

Methods other than ultrasound may also be used to locate the tip of the guidewire and these may be considered in order to reduce cost or complexity of the system. Some such methods include microwaves, fluoroscopy, intramyocardial pressure, electrical impedance, electrical resistance, and optical sensing.

Devices with varying lengths are also contemplated through the use of telescoping tubes. These devices, advantageously, do not inhibit contraction of the myocardial tissue but instead to limit over-expansion or distension.

Figure 49A:
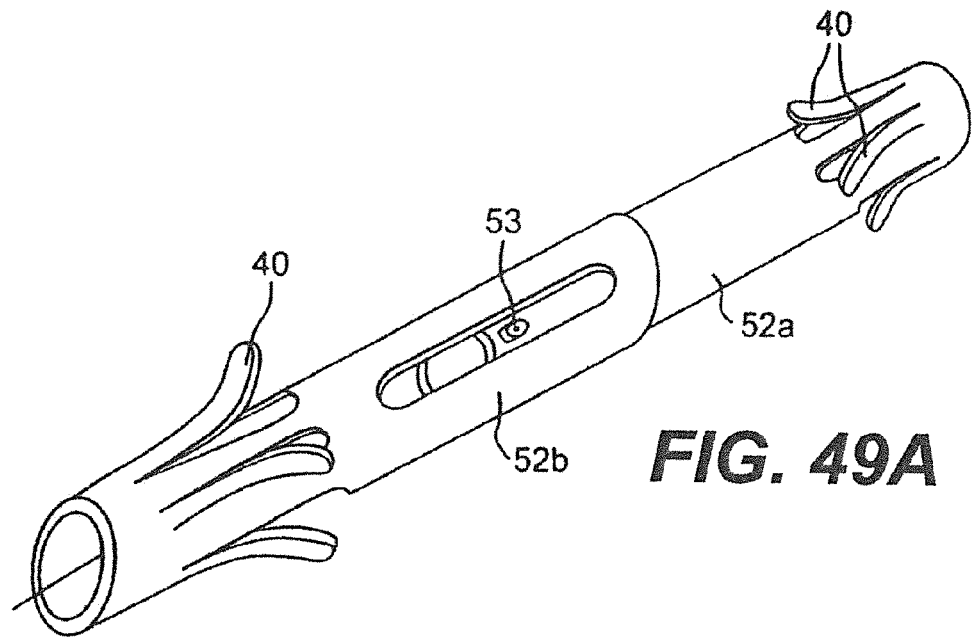
FIGS. 49A through 49C show an alternative embodiment of the present invention including a slidably disposed telescoping body.
Figure 49B:
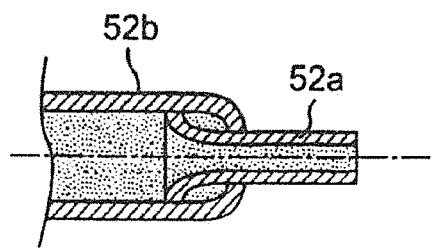
Figure 49C:
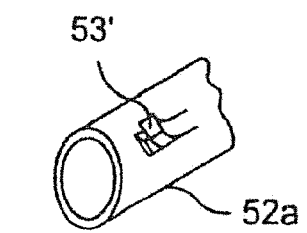

Referring to FIGS. 49a through 49c, the device consists of two concentric tubes which nest together in a telescoping manner. The tubes are preferably nitinol, titanium or high strength stainless steel. It may also be possible to use polymer and other materials. At least one stop 53 projects outward from the outer diameter of the inner tube 52a and engages a slot cut longitudinally through the wall of the outer tube 52b. The engagement of the stop in the slot limits the relative motion of the two tubes and therefore limits the maximum elongation of the overall device. Also shown are i) a stop created by cutting a U shaped slot through the wall of the inner tube 52a and creating a sharp outward bend in the tongue 53' of material created by such a slot such that the end of the tongue projects radially outward to engage the slot in the outer tube 52b, and ii) and alternative method to limit the elongation of the nested tube assembly wherein the rim of one end of the outer tube is deformed inwardly and the rim of one end of the inner tube is flared outwardly, as shown in FIG. 49b.

On one end of each tube there is created an anchor element 40. In the figure the anchor element shown is one created by cutting several elongated U-shaped slots through the wall of the tube end and deforming the tongue shaped tube wall material circumscribed by each U shaped slot into a outward projecting barb. A bulge type anchor may be created in a similar manner. Both type anchors can be deflected so that the overall device may by contained in a catheter with an inner diameter (10) close to that of the outer diameter (OD) of the device's outer tube.

This device may be placed and deployed over a guidewire whose OD is marginally smaller than the 10 of the inner tube.

The present invention also contemplates implanting microspheres into the myocardal tissue to accomplish stiffening, restraint or constraint of the tissue. Microspheres, as known in the art, may be applied through a variety of techniques, for example injection into blood stream or tissue, open surgical and minimally invasive implantation. Microspheres advantageously can be made from expandable and/or dissolvable material. They are proven able to be encapsulated, from diverse therapies using bulking agents, cyano, drug therapy, and peptides. Further, injectables can be a diverse range of materials such as metal, biologics, non-biologic polymer, chemical agents, or collagen, to name a few.

Perhaps the most widely utilized injectable agent is collagen, a safe material that appears inert and has minimal incidence of adverse effects. Collagen is used in many dermatological applications to smooth out wrinkles and in other cosmetic procedures such as lip augmentation.

Overall. collagen is an excellent alternative for an elderly patient with urethral sphincter weakness who may not be able to tolerate a surgical procedure. Collagen is also an excellent alternative in patients who have had multiple surgical procedures and still require some strengthening of the urethral musculature.

Injectable materials include collagen (naturally occurring protein found in skin, bone, and connective tissue), fat from the patient's body (autologous fat), and polytetrafluoroethylene {PTFE) and Durasphere™ (synthetic compounds).

Collagen is a natural substance that breaks down and is excreted over time. The Contigen® Bard® collagen implant uses a purified form of collagen derived from cowhide. Potential recipients have a skin test 28 days prior to treatment to determine whether or not they are sensitive to the material. Sensitivity is indicated by inflammation at the injection site.

A prefilled syringe is used to inject the collagen around the urethra. Some physicians conduct a series of treatments over a few weeks or months. Others instruct patients to return for additional treatment when leakage occurs. Results vary from patient to patient and from physician to physician. Some patients achieve continence for 12 to 18 months and others require more frequent treatment. Some remain dry for 3 to 5 years.

Autologous fat injections are used to treat intrinsic sphincter deficiency. Fat from the patient's body is gathered by liposuction from the abdominal wall and is injected around the urethra in a simple procedure performed under local anesthesia, long-term effectiveness of this procedure is not known.

Polytetrafluoroethylene (PTFE) is a synthetic compound, and is available in the form of a micropolymer paste that is injected into the upper urethra. The PTFE particles spur the growth of fibroblasts (fiber-making cells), which fix the material in the urethral tissue and assist in urethral closure. PTFE is not an approved treatment for incontinence in the United States because PTFE particles may migrate to other parts of the body, such as the lungs, brain, and lymph nodes.

Durasphere™ is a water-based gel that contains tiny, carbon-coated beads. Unlike PTFE, this material is not absorbed by the body. The procedure is usually performed under local anesthesia, although some patients may require general anesthesia.

By enclosing a therapeutic compound in a liposome, such a Gilead, scientists have discovered a new drug delivery system that offers Significant benefits over conventional delivery methods.

Liposomal technology has demonstrated improvements in the way a therapeutic is released throughout the body, as well as the amount of time it remains within the body. Liposomes may circulate in the bloodstream for extended periods, as compared to the same therapy in a non-liposomal form. This may result in an extended treatment effect and a simplified dosing regimen for both physicians and patients.

In some cases, liposomal therapies have been shown to accumulate at the site of a tumor or infection, delivering higher concentrations of that therapy to the disease target. The liposome carrier is believed to play a role in reducing the harmful effects of certain therapies on healthy tissues, thereby offering the potential for an improved safety profile for certain drugs.

Gliadel® Wafer is a unique form of treatment for brain tumors: wafers implanted into the tumor site at the time of surgery that slowly release a chemotherapy. They were approved by the FDA on Sep. 23, 1996 and no longer Considered experimental, the wafers were designed to deliver a chemotherapy drug directly to the area of the brain tumor, bypassing the blood brain barrier. They are implanted into the space formed by the removal of tumor at the time of the surgery, and left in. They "dissolve" by themselves eventually—they do not have to be removed. Further advantageously, they slowly release a drug called BCNU, over a period of about 2-3 weeks.

Also contemplated is a bisphere configuration: a layer or shell within a shell. The inner shell, formed from biodegradable biopolymers, provides physical structure and controls acoustic response, while the outer layer functions as the biological interface and provides a scaffold for site-specific targeting ligands. Each layer or shell can be independently modified to fulfill specific application requirements. The core or payload space can be filled with a gas such as nitrogen for ultrasound imaging such as a myocardial perfusion agent or with biotherapeutic agents for drug delivery applications.

The dual shelled microspheres designed to hold a variety of drugs or biotherapeutic agents. These are lyophilized and reconstituted prior to intravenous injection. The bispheres circulate through the blood stream and can be visualized using standard ultrasound diagnostic imaging instrumentation. The bispheres can be fractured by insonation with a special ultrasound "bursting" signal focused on a target site. The collapse of fracturing bispheres within the target site can be acoustically detected providing feedback as to the quantity of active drug being released at the site. The use of bispheres to transport agents to specific sites within the body can substantially increase local efficacy while decreasing systemic side effects or adverse reactions.

PolyMicrospheres and Advanced Nanotechnologies, Divisions of Vasmo, Inc., are leaders in developing Microparticle and Nanoparticle-based Drug Delivery Systems with embedded chemotherapeutics and other pharmaceutical compounds for the controlled-release delivery of drugs to affected tissues over an extended period.

Microsphere embodiments of the present invention advantageously allow for controlled-release (extended-release and time-release) delivery systems. and targeted and site-specific delivery systems. The therapy contemplated by the present invention can be practiced through employing microsphere/nanosphere-based medical devices, injectable microspheres and nanospheres, implantable microbeads, laminated/coated microsystems and nanosystems, microemulsions, hydrogels, microencapsulation and matrix technologies, parenteral and chemotherapeutic delivery systems to name a few.

Materials contemplated in the practice of the present invention include biodegradable polymers, polylactide (PLA), polyglycolide (PGA), lactide-glycolide copolymers (PLG), polycaprolactone, lactide-caprolactone copolymers, polyhydroxybutyrate, polyalkylcyanoacrylates, polyanhydrides, polyorthoesters, proteins such as albumin, collagen, gelatin, polysaccharides such as dextrans, starches, biocompatible polymers contemplated include acrylate polymers and copolymers; methyl methacrylate, methacrylic acid; hydroxyalkyl acrylates and methacrylates; methylene glycol dimethacrylate; acrylamide. bisacrylamide; cellulose-based polymers; ethylene glycol polymers and copolymers; oxyethylene and oxypropylene polymers; poly(vinyl alcohol) and polyvinyl acetate; polyvinylpyrrolidone and polyvinylpyridine.

Deflux is a sterile, injectable bulking agent composed of microspheres of crosslinked dextran ("dextranomer." 50 mg/ml) suspended in a carrier gel of non-animal, stabilized hyaluronic acid (17 mg/ml).

Deflux is injected submucosally in the urinary bladder in close proximity to the ureteral orifice. The injection of Deflux creates increased tissue bulk, thereby providing coaptation of the distal ureter during filling and contraction of the bladder. The dextranomer microspheres are gradually surrounded by body's own connective tissue, which provides the final bulking effect.

Liquid embolic is a cyanoacrylate material that polymerizes into a solid material upon contact with body fluids and can be used in the practice of the present invention.

The development of new biomaterials involves a complicated mix of materials science and cell biology. Current and future research promises to introduce not just a new crop of materials, but an entirely new way of treating illness. Intriguing work is being conducted in areas such as bioresorbables, collagen-based materials, fibrin sealants and glues, hyaluronic acid derivatives, engineered tissues, and other products for the cardiovascular, musculoskeletal, and surgical markets.

Silk elastin sponges are polymers being developed to provide a matrix for wound healing and drug delivery. Photos courtesy of Protein Polymer Technologies (San Diego).

One particularly dynamic area of research is controlled drug delivery. The demand for different delivery technologies has reached a critical point because many engineered drugs are large, high-molecular-weight proteins and enzymes that can't be administered orally. Also, without a targeted release mechanism, drug levels tend to fluctuate, which means that more of the drug must be administered, increasing the likelihood of side effects and raising health-care costs.

Noted researcher Robert Langer, Germeshausen professor of chemical and biomedical engineering at the Massachusetts Institute of Technology, is among those pursuing more precise and sustainable drug-delivery mechanisms. In the most common current approaches, the drug is encased in a reservoir, from which it gradually leaches out, or else it is compounded into a degradable polymer, from which it is gradually released as the polymer breaks down inside the body. This latter approach is the basic principle behind the Gliadel system for treating brain cancer, approved by FDA just last year, which Langer was instrumental in developing.

Another approach contemplated by the present invention involves the implantation of living cells encased in a protective medium that withstands implantation while allowing passage of the substances naturally produced by those cells. Such an approach has been investigated for insulin delivery. Islet Technology, Inc. (North Oaks, Minn.), employs a proprietary encapsulation technology that uses a purified alginate (seaweed-derived) material to coat insulin-producing islet cells. Others use carbon-based microspheres. Sol gene Therapeutics LLC (Westlake Village, Calif.), on the other hand, is working with a purely synthetic encapsulation matrix, silica gel.

The present invention may also be employed in various forms for bone repair, another important market for biomaterials.

The same basic polymer used for controlled drug release might also hold potential as a scaffolding material for supporting the growth of tissue—particularly when seeded with appropriate morphogenic compounds. The information gained from investigating the mechanisms of cell attachment and endothelialization, for example, might yield useful insights into the nature of non-thrombogenic coatings or tissue sealants.

For example, the vascular endothelium presents an adhesive collagen membrane on one side, but its other side is a nonstick surface that prevents adhesion of blood cells and platelets. Both membranes are composed of protein illustrating that proteins can change profile. Because attachment is an active process, and specifically, certain epitopes have evolved to look for specific triggers or cellular receptors that promote active association or adhesion. There are protein combinations that are essentially a nonstick surface. By placing into those designs recognition factors for cell attachment, the opposite can be created.

Tissue engineering is an interdisciplinary science that focuses on the development of biological substitutes that restore, maintain, or improve tissue function. The most common tissue engineering strategies involve the use of isolated cells or cell substitutes, tissue-inducing substances, and cells seeded on or within matrices. Such approaches practiced in these areas can be used in the practice of the present invention in its various forms.

While the descriptions above have focused on the long-term benefits of the therapy, these devices also acutely improve left ventricular systolic function. The above systems all decrease wall stress in the peri-infarct region. The above systems also decrease the size of the infarct tissue and/or increase the stiffness of the infarct tissue. Decreasing the infarct size decreases the overall size of the left ventricle, which decreases overall wall stress. Increased infarct stiffness eliminates or minimizes any expansion of the infarct region during systole, which increases the efficiency of the contract; i.e., more of the energy of the contracting myocytes is translated into ejecting blood from the left ventricle.

It is also to be appreciated that the devices and methods described hereinabove to constrain or shrink an infarct region can also be used to shrink the size of the heart in patients with dilated cardiomyopathy. By reducing the size of the heart, wall stress is reduced on the myocytes, resulting in improved left ventricular function.

Further, while the previous descriptions have focused on decreasing the size of the heart or infarcted tissue, some patients develop heart failure due to diastolic heart failure. Left ventricular systolic function in these patients is normal, but the left ventricular diastolic function is abnormal. This condition makes it difficult for the ventricle to fill during diastole. With inadequate filling, ejection fraction is depressed and the left ventricle cannot pump enough blood to meet the body's demand for oxygen. The above devices that are designed to shrink tissue can be applied in reverse to expand tissue. Here, the spring-like device is deployed with the spring compressed. Once deployed, the spring lengthens, thereby stretching the myocardium. Meshes that expand axially or radially may be employed in analogous fashion, as can materials that expand when injected, or shape memory alloys that lengthen. The mechanical characteristics of the devices are adjusted, so that the spring force of the device is greater than the wall stresses present in diastole, but less than the wall stresses present in systole. Thus, the devices help to expand the heart in diastole, partially resolving the filling problem. Yet, in systole, the devices have minimal effect on left ventricular contraction. The net effect is toward normal filling left ventricular filling and volumes and normal cardiac output.

Of course, to the extent that the left ventricle is used illustratively to describe the invention, all of the methods and devices described above are also applicable to the right ventricle.

EXAMPLES

The inventors have performed two theoretical analyses to predict the physiological effects of applying the devices and methods according to the present invention. The results demonstrate an improvement in global cardiac function.

The first study used an analysis recently developed at Columbia University (Artrip J H. Oz M C, Burkhoff O, "LV Volume Reduction Surgery For Heart Failure: A Physiologic Perspective," J Thorac Cardiovasc Surg 2001; 122:775-82). The hemodynamic effect of altering regional wall characteristics were predicted by using a composite model of the left ventricle in which 20% of the myocardium was given properties of non-contracting ischemic muscle. Myocardial infarction depressed ventricular function. Altering regional wall characteristics by stiffening, restraining, or constraining the infarct tissue shifted the endsystolic and end-diastolic pressure-volume relationships leftward. However. the leftward shift was greater for end-systolic than for end-diastolic pressure-volume relationships. Thus, the effect on overall pump function (the relationship between total ventricular mechanical work and end-diastolic pressure) was beneficial, recovering approximately 50% of the lost function.

Figure 50A:
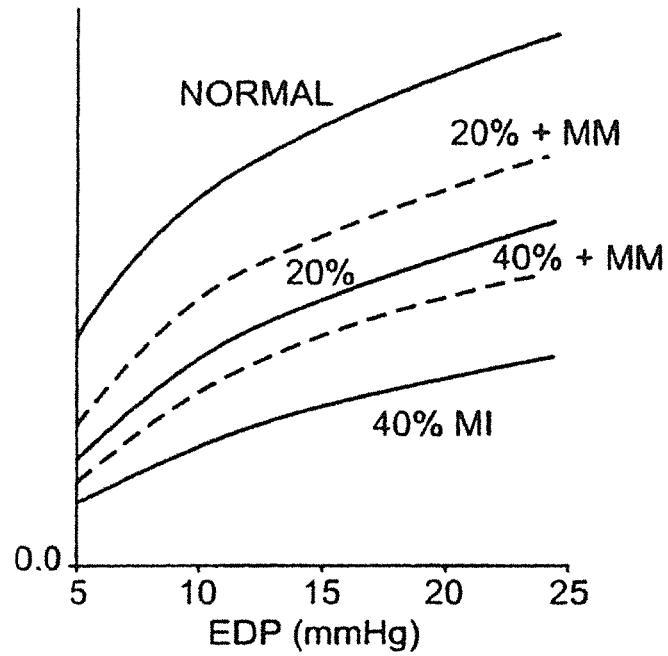
FIGS. 50A and 50B are graphical views of some aspects of the performance of the present invention.
Figure 50B:
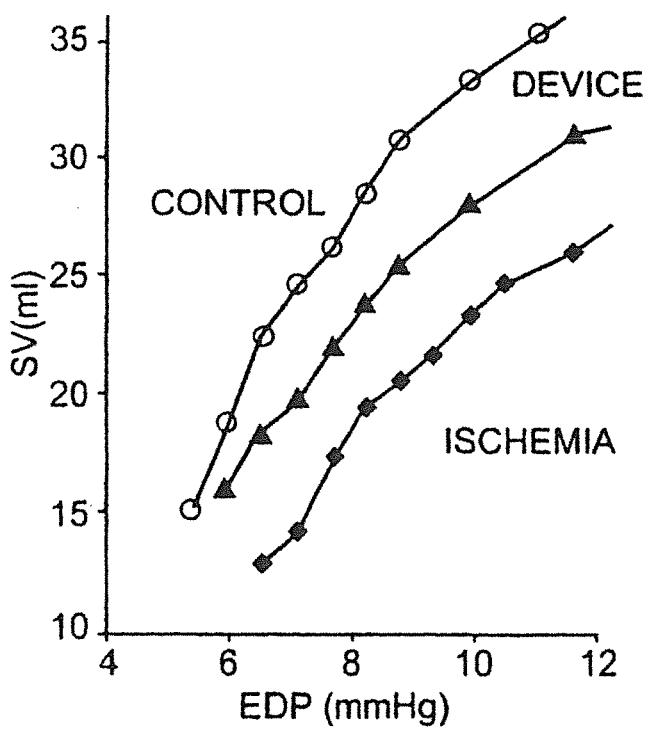

The second theoretical analysis employed a lump parameter model of the circulation (Bamea. O. Santamore, W P. "Intra-Operative and Post-Operative Monitoring of IMA Flow: What Does-It Mean?". Ann. Thorac. Surg. 1997; 63: S12-s17). This model predicts flow and pressures throughout the circulation as well as ventricular volumes. Myocardial infarctions effecting 20 and 40% of the LV were simulated. As shown in FIG. 50a. acute myocardial infarction depressed LV function; the cardiac output versus end-diastolic pressure relationship was depressed for a 20% MI and severely depressed for a 40% MI. Once again altering regional wall characteristics of the infarct tissue resulted in a physiologically important increase in this relationship.

Figure 51:
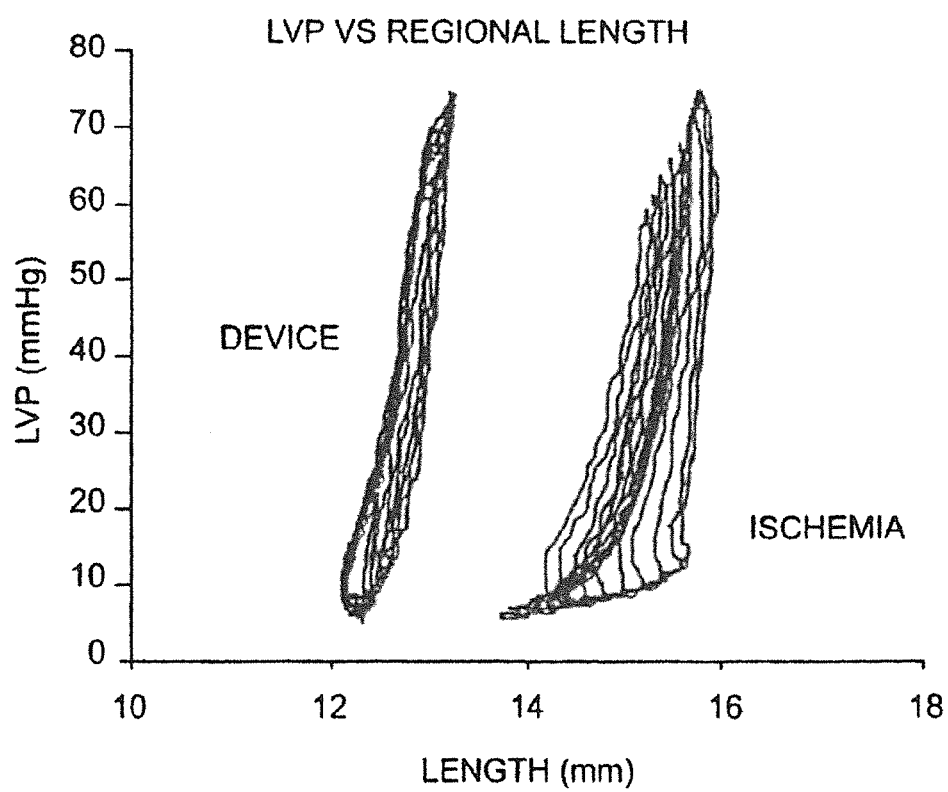
FIG. 51 is a graphical view of another aspect of the performance of the present invention.

The inventors have also performed initial in-vivo experiments in adult pigs designed to test various device concepts and their acute physiological effects. In pigs, LV pressure. aortic flow, LV volume (measured by sonocrystals), and regional wall motion (measured by sonocrystals) were measured. The devices according to the present invention were able to consistently alter regional wall characteristics. FIG. 51 further depicts model results of the device alongside ischemic myocardial tissue, plotting left ventricular pressure against tissue length over a cardiac cycle. The general inclination left to right of both curves show that there is some elongation in the regional length of the myocardial tissue as ventricular pressure increases. However, there is far less overall variation in the curve representing tissue treated according to the present invention. Further, in absolute terms, the treated tissue is more compact, as represented by the location of the curve representing the treated ischemic tissue residing entirely to the left of the curve representing the untreated ischemic tissue. This figure illustrates that the treated tissue exhibits greater stiffness than untreated ischemic tissue, which translates to less energy absorbed by myocardial tissue elasticity, and improved cardiac performance and function.

Without ischemia, the devices had no 'effect on global LV function. In the presence of myocardial ischemia, these experiments demonstrated the same improvement in global cardiac function that had been anticipated by the theoretical modeling: acute myocardial infarction depressed function, and the devices improved function.

It is also contemplated that the devices according to the present invention can, be made to be drug- or therapeutic agent-eluting. After a myocardial infarction, collagen can be degraded by extracellular matrix metalloproteases (enzymes that are normally present in latent form in the myocardium). The metalloproteases are activated by myocardial ischemia, and can contribute to the degradation of collagen. Inhibitors of matrix metalloproteases can be eluded from the device. This would advantageously slow down or prevent the degradation of the collagen. In many cases on wound healing it is desirable to control or minimize scar formation. However, after a myocardial infarction the converse may be better—to accentuate scar formation. Transforming growth factor beta 1, beta 2, and beta 3 together with collagen are known to modulate this healing process with scar formation and contraction. Eluding these factors 0 from the device will accentuate the scar formation and scar contraction, and thus improve the performance of the device.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for direct localized therapeutic treatment of myocardial tissue in a heart, the method comprising the steps of:
    identifying a target region comprising an infarct region of the myocardium of the heart to be treated;
    injecting particles, which bond to cells in the infarct region, in a viscous biocompatible gel matrix into the target region to stiffen at least the target region of the myocardium.

2. The method of claim 1, wherein the step of injecting particles comprises injecting particles which bond to dead cells in the infarct region.

3. The method of claim 1, wherein the step of injecting particles comprises injecting particles selected from the group consisting of metal particles, microspheres, metal microspheres and lyophilized particles.

4. The method of claim 1, wherein the step of injecting particles comprises injecting particles smaller than 25 μM in a viscous biocompatible gel matrix.

5. The method of claim 1, wherein the step of injecting particles comprises injecting particles which become encapsulated in the myocardium.

6. The method of claim 1, wherein the step of injecting particles comprises injecting a material containing peptides.

7. The method of claim 1, further comprising the step of accessing the heart to inject the particles through an approach selected from the group consisting of an open chest approach, a mini-thoracotomy approach and a percutaneous approach.

8. The method of claim 1, wherein the step of injecting particles further comprises injecting a luminescent, radiopaque or other contrast agent to enhance visualization.

9. The method of claim 1, wherein the step of injecting particles comprises intravenously injecting particles such that the particles travel through the circulation to the target region to stiffen at least the target region.

10. A method for direct localized therapeutic treatment of myocardial tissue in a heart, the method comprising the steps of:
    identifying a target region of the myocardium of the heart to be treated; and
    injecting a material into the target region to stiffen at least the target region of the myocardium, wherein the target region is an infarct region and the material bonds to cells or proteins associated with cells in the infarct region.

11. The method of claim 10 wherein the step of injecting material comprises intravenously injecting the material into the patient such that the material travels through the circulation to the infarcted tissue to stiffen the infarcted tissue.

12. The method of claim 11, wherein the step of intravenously injecting a material comprises intravenously injecting a material including a luminescent, radiopaque or other contrast agent to enhance visualization.

13. The method of claim 10, wherein the step of injecting a material comprises injecting a material which bonds to proteins associated with cell necrosis.

14. The method of claim 10, wherein the step of injecting a material comprises injecting a material which bonds to myocytes.

15. The method of claim 10, wherein the step of injecting a material comprises injecting a material which bonds to proteins associated with infarct tissue.

16. The method of claim 10, wherein the step of injecting a material comprises injecting a material containing peptides.

17. The method of claim 10, further comprising the step of accessing the heart to inject the material through an approach selected from the group consisting of an open chest approach, a mini-thoracotomy approach and a percutaneous approach.

18. The method of claim 10, wherein the step of injecting a material comprise injecting a biologic material.

* * * * *